United States Patent
Hahn et al.

(10) Patent No.: US 9,291,621 B2
(45) Date of Patent: Mar. 22, 2016

(54) AGER-PEPTIDES AND USE THEREOF

(75) Inventors: Alfred Hahn, Mannheim (DE); Ralf Loebbert, Speyer (DE); Nicole Teusch, Wülfrath (DE); Achim Möller, Grunstadt (DE); Ulrich Ebert, Ludwigshafen (DE); Martin Schmidt, Benshelm (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 1940 days.

(21) Appl. No.: 11/795,282

(22) PCT Filed: Jan. 18, 2006

(86) PCT No.: PCT/EP2006/000420
§ 371 (c)(1),
(2), (4) Date: Mar. 16, 2010

(87) PCT Pub. No.: WO2006/077101
PCT Pub. Date: Jul. 27, 2006

(65) Prior Publication Data
US 2010/0226915 A1    Sep. 9, 2010

Related U.S. Application Data

(60) Provisional application No. 60/645,211, filed on Jan. 18, 2005, provisional application No. 60/668,704, filed on Apr. 5, 2005, provisional application No. 60/681,211, filed on May 13, 2005.

(30) Foreign Application Priority Data

Jan. 18, 2005 (DE) .......................... 10 2005 002 353
Apr. 6, 2005 (DE) .......................... 10 2005 015 832
May 13, 2005 (DE) .......................... 10 2005 022 285

(51) Int. Cl.
A61K 39/00        (2006.01)
G01N 33/564    (2006.01)
C07K 16/28       (2006.01)

(52) U.S. Cl.
CPC .......... *G01N 33/564* (2013.01); *C07K 16/2803* (2013.01); *G01N 2500/00* (2013.01)

(58) Field of Classification Search
CPC .......... C07K 16/2803; G01N 2500/00; G01N 33/564
USPC ................ 424/133.1, 134.1, 178.1; 435/69.6; 530/387.1, 387.3
See application file for complete search history.

(56) References Cited

U.S. PATENT DOCUMENTS

2003/0087302 A1    5/2003    Schmidt et al.

FOREIGN PATENT DOCUMENTS

| JP | 2003-230382 | 8/2003 |
| JP | 2004-236791 | 8/2004 |
| WO | WO 97/39121 | 10/1997 |
| WO | WO 97/39125 | 10/1997 |
| WO | WO 99/18987 | 4/1999 |
| WO | WO 9918987 A1 * | 4/1999 |
| WO | WO 99/54485 | 10/1999 |
| WO | WO 01/92892 | 12/2001 |
| WO | WO 2004/016229 | 2/2004 |

OTHER PUBLICATIONS

Bucciarelli et al., CMLS Cellular and Molecular Life Sciences, "RAGE is a Multiligand Receptor of the Immunoglobulin Superfamily: Implications for Homeostasis and Chronic Disease", 59 (2002) pp. 1117-1128.
Hofmann et al., American Journal of Respiratory and Critical Care Medicine, "Discrimination of Human Lung Neoplasm from Normal Lung by Two Target Genes", vol. 170 (2004), pp. 516-519.
Jerums et al., Archives of Biochemistry and Biophysics, "Evolving Concepts in Advanced Glycation, Diabetic Nephropathy, and Diabetic Vascular Disease", 419 (2003) pp. 53-62.
Lotze al., Current Opinion in Investigational Drugs, "Dealing with Death: HMGB1 as a Novel Target for Cancer Therapy", vol. 4, No. 12, (2003), pp. 1405-1409.

* cited by examiner

*Primary Examiner* — Gregory S Emch
(74) *Attorney, Agent, or Firm* — Lisa V. Mueller; Michael Best & Friedrich LLP

(57) ABSTRACT

The present invention relates to the identification, functionality and use of domains from the N terminus of the receptor for Advanced Glycation End Products (AGER). These domains, called receptor multimerization epitope (RME), are highly conserved in all AGER protein sequences. They represent the mediators for AGER self-association and heteromerization with other proteins. The invention likewise relates to the identification, functionality and use of peptides derived from the C domain of AGER (AGER-CDP). The AGER RMEs and AGER-CDPs of the invention are suitable as target for identifying AGER ligands which modulate the natural ligand interaction; as immunogen for active or passive immunization of individuals, as diagnostic means for identifying immunogenic reactions, and as peptide ligands for modulating protein-protein interactions involving AGER.

9 Claims, 19 Drawing Sheets

RAGE sequence comparison:

```
                     |++++++++++++++++++++++++++|
Human    MAAGTAVGAWVLVLSLWGAVVGAQNITARIGEPLVLKCKGAPKKPPQRLEWKLNTGRTEA
Mouse    MPAGTAARAWVLVLALWGAVAGGQNITARIGEPLVLSCKGAPKKPPQQLEWKLNTGRTEA
Rat      MPTGTVARAWVLVLALWGAVAGGQNITARIGEPLMLSCKGAPKKPTQKLEWKLNTGRTEA
Bovine   MAAGAVVGAWMLVLSLGGTVTGDQNITARIGKPLVLNCKGAPKKPPQQLEWKLNTGRTEA
         *  :*:.. **:***:* *:*.* ********:**:* ******* *:*:**********

Human    WKVLSPQGGGPWDSVARVLPNGSLFLPAVGIQDEGIFRCQAMNRNGKETKSNYRVRVYQI
Mouse    WKVLSPQGG-PWDSVAQILPNGSLLLPATGIVDEGTFRCRATNRRGKEVKSNYRVRVYQI
Rat      WKVLSPQGD-PWDSVARILPNGSLLLPAIGIVDEGTFRCRATNRLGKEVKSNYRVRVYQI
Bovine   WKVLSPQGD-PWDSVARVLPNGSLLLPAVGIQDEGTFRCRATSRSGKETKSNYRVRVYQI
         ********. ******::******:*** ** *** ***:*  * *** **********

Human    PGKPEIVDSASELTAGVPNKVGTCVSEGSYPAGTLSWHLDGKPLVPNEKGVSVKEQTRRH
Mouse    PGKPEIVDPASELTASVPNKVGTCVSEGSYPAGTLSWHLDGKLLIPDGKETLVKEETRRH
Rat      PGKPEIVNPASELTANVPNKVGTCVSEGSYPAGTLSWHLDGKPLIPDGKGTVVKEETRRH
Bovine   PGKPEIVDPASELMAGVPNKVGTCVSEGGYPAGTLNWLLDGKTLIPDGKGVSVKEETKRH
         *******:.**** *.************.******.* **** *:*:  *  ***:*:**

Human    PETGLFTLQSELMVTPARGGDPRPTFSCSFSPGLPRHRALRTAPIQPRVW----------
Mouse    PETGLFTLRSELTVIPTQGGTTHPTFSCSFSLGLPRRRPLNTAPIQLRVR----------
Rat      PETGLFTLRSELTVTPAQGGTT-PTYSCSFSLGLPRRRPLNTAPIQPRVR----------
Bovine   PKTGLFTLHSELMVTPARGGALHPTFSCSFTPGLPRRRALHTAPIQLRVWSEHRGGEGPN
         *:*******:*** * *::**   **:****: ****:*.*:.***** **

Human    -EPVPLEEVQLVVEPEGGAVAPGGTVTLTCEVPAQPSPQIHWMKDGVPLPLPPSPVLILP
Mouse    -EPGPPEGIQLLVEPEGGIVAPGGTVTLTCAISAQPPPQVHWIKDGAPLPLAPSPVLLLP
Rat      -EPLPPEGIQLLVEPEGGTVAPGGTVTLTCAISAQPPPQIHWIKDGTPLPLAPSPVLLLP
Bovine   VDAVPLKEVQLVVEPEGGAVAPGGTVTLTCEAPAQPPPQIHWIKDGRPLPLPPGPMLLLP
         :.  *  :  :**:****** ***********   .***.**:**:*** ****.*.*:*:**

Human    EIGPQDQGTYSCVATHSSHGPQESRAVSISIIEPGEEGPTAGSVGGSGLGTLALALGILG
Mouse    EVGHADEGTYSCVATHPSHGPQESPPVSIRVTETGDEGPAEGSVGESGLGTLALALGILG
Rat      EVGHEDEGIYSCVATHPSHGPQESPPVNIRVTETGDEGQAAGSVDGSGLGTLALALGILG
Bovine   EVGPEDQGTYSCVATHPSHGPQESRAVSVTIIETGEEGTTAGSVEGPGLETLALTLGILG
         *:*  *:* ******* *******  .*.:  : *.:** : ***   ** ****:*****

Human    GLGTAALLIGVILWQRR-QRRGEERKAPENQEEEEE-RAELNQSEEPEAGESSTGGP
Mouse    GLGVVALLVGAILWRKR-QPRREERKAPESQEDEEE-RAELNQSEEAEMPENGAGGP
Rat      GLGIAALLIGAILWRKR-QPRLEERKAPESQEDEEE-RAELNQSEEAEMPENGAGGP
Bovine   GLGTVALLIGVIVWHRRRQRKGQERKVPENQEEEEEERAELNQPEEPEAAESSTGGP
         ***  .***:*.*:*::* *  :  :***.**.**.***:****** **. *  .:***
```

ClustAll W alignment of the protein sequences:
Ref.Seq Ids:
NP_001127 human
NP_031451 mouse
NP_445788 rat
NP_776407 Bovine Ig-like V-type
Ig-like C2-type 1
Ig-like C2-type 2

Fig. 1

Anti p75         Anti NgR
HEK293
HEK293 triple transfectant
4
8
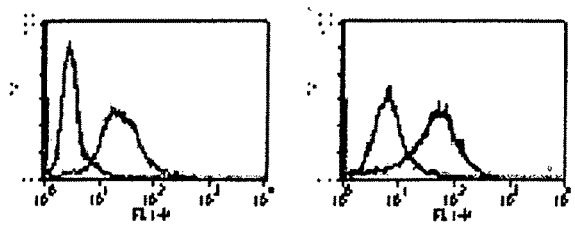
Fig. 4b A)
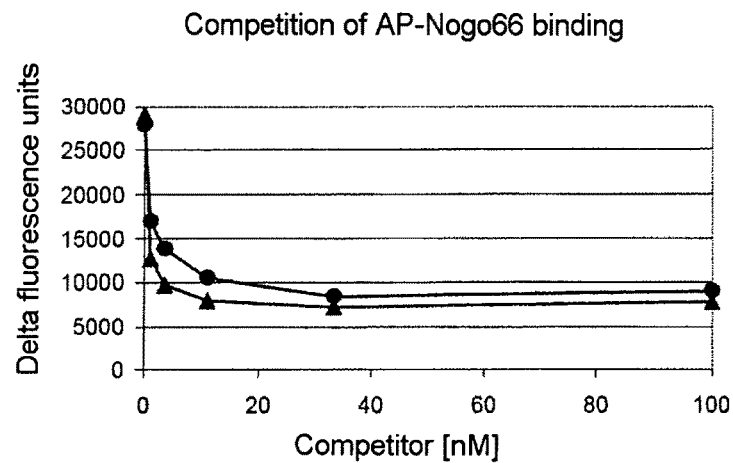
B)
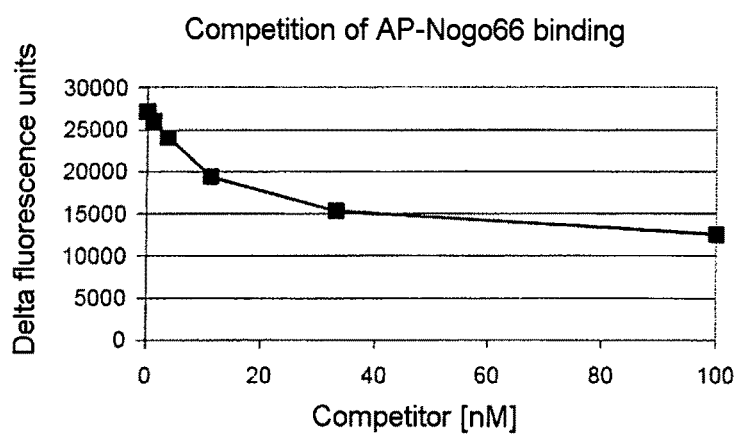
Fig. 10

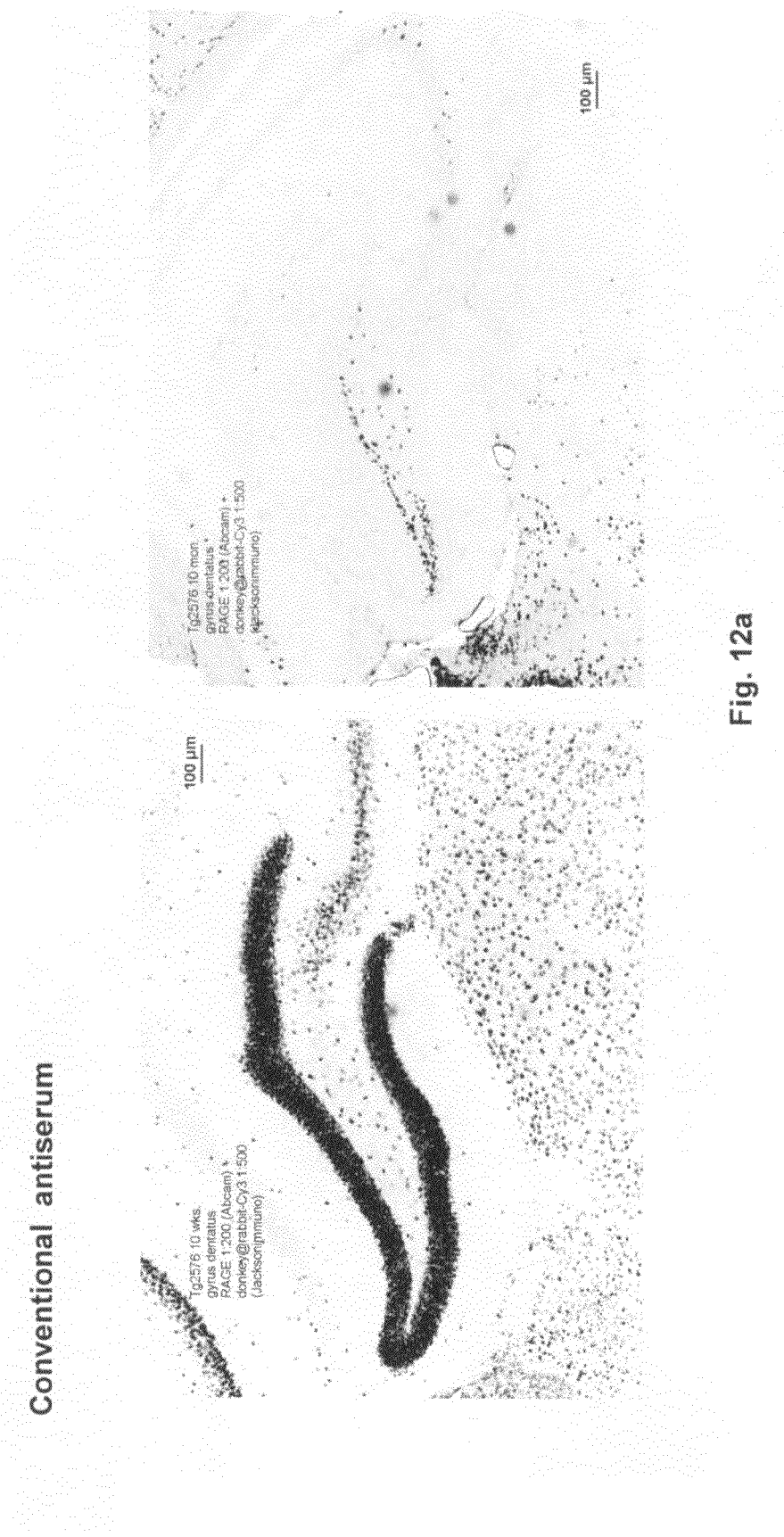

SEQUENCE LISTING

<160> NUMBER OF SEQ ID NOS: 37

<210> SEQ ID NO 1
<211> LENGTH: 13
<212> TYPE: PRT
<213> ORGANISM: Artificial Sequence
<220> FEATURE:
<223> OTHER INFORMATION: AGER-RME Sequence
<220> FEATURE:
<221> NAME/KEY: MISC_FEATURE
<222> LOCATION: (2)..(2)
<223> OTHER INFORMATION: Xaa is Lys or Arg
<220> FEATURE:
<221> NAME/KEY: MISC_FEATURE
<222> LOCATION: (9)..(9)
<223> OTHER INFORMATION: Xaa is Pro or Thr
<220> FEATURE:
<221> NAME/KEY: MISC_FEATURE
<222> LOCATION: (11)..(11)
<223> OTHER INFORMATION: Xaa is Gln, Lys or Arg

<400> SEQUENCE: 1

Cys Xaa Gly Ala Pro Lys Lys Pro Xaa Gln Xaa Leu Glu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Nterm13-1

<400> SEQUENCE: 2

Cys Arg Gly Ala Pro Lys Lys Pro Pro Gln Gln Leu Glu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Nterm13

<400> SEQUENCE: 3

Cys Lys Gly Ala Pro Lys Lys Pro Pro Gln Arg Leu Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Nterm13-2

<400> SEQUENCE: 4

Cys Lys Gly Ala Pro Lys Lys Pro Thr Gln Lys Leu Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Partial AGER-RME sequence
<220> FEATURE:
<221> NAME/KEY: MISC_FEATURE
<222> LOCATION: (8)..(8)
<223> OTHER INFORMATION: Xaa is Lys or Glu
<220> FEATURE:
<221> NAME/KEY: MISC_FEATURE

```
<222> LOCATION: (11)..(11)
<223> OTHER INFORMATION: Xaa is Val or Met
<220> FEATURE:
<221> NAME/KEY: MISC_FEATURE
<222> LOCATION: (13)..(13)
<223> OTHER INFORMATION: Xaa is Asn, Ser or Lys

<400> SEQUENCE: 5

Asn Ile Thr Ala Arg Ile Gly Xaa Pro Leu Xaa Leu Xaa
1               5                   10

<210> SEQ ID NO 6
<211> LENGTH: 31
<212> TYPE: PRT
<213> ORGANISM: Artificial Sequence
<220> FEATURE:
<223> OTHER INFORMATION: Nterm31

<400> SEQUENCE: 6

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: ScraNterm31

<400> SEQUENCE: 7

Ala Pro Leu Ala Cys Pro Arg Glu Leu Ile Lys Gly Lys Trp Glu Val
1               5                   10                  15

Lys Pro Lys Arg Asn Pro Lys Asn Gln Leu Thr Ile Gly Gln Leu
            20                  25                  30

<210> SEQ ID NO 8
<211> LENGTH: 13
<212> TYPE: PRT
<213> ORGANISM: Artificial Sequence
<220> FEATURE:
<223> OTHER INFORMATION: ScraNterm13

<400> SEQUENCE: 8

Gly Lys Pro Arg Ala Pro Lys Cys Leu Lys Pro Glu Gln
1               5                   10

<210> SEQ ID NO 9
<211> LENGTH: 31
<212> TYPE: DNA
<213> ORGANISM: Artificial Sequence
<220> FEATURE:
<223> OTHER INFORMATION: PCR primer mez402

<400> SEQUENCE: 9
gccaccatga ggatatacaa gggtgtgatc c                               31

<210> SEQ ID NO 10
<211> LENGTH: 24
<212> TYPE: DNA
<213> ORGANISM: Artificial Sequence
<220> FEATURE:
<223> OTHER INFORMATION: PCR primer mez404

<400> SEQUENCE: 10
```
cttcagagaa tcaactaaat catc                                              24

<210> SEQ ID NO 11
<211> LENGTH: 6850
<212> TYPE: DNA
<213> ORGANISM: Artificial Sequence
<220> FEATURE:
<223> OTHER INFORMATION: Plasmid pP-tag5APnogo66

<400> SEQUENCE: 11

| | | | | | |
|---|---|---|---|---|---|
| aattgcatga | agaatctgct | tagggttagg | cgttttgcgc | tgcttcgcga | tgtacgggcc      60 |
| agatatacgc | gttgacattg | attattgact | agttattaat | agtaatcaat | tacgggtca     120 |
| ttagttcata | gcccatatat | ggagttccgc | gttacataac | ttacggtaaa | tggcccgcct    180 |
| ggctgaccgc | ccaacgaccc | ccgcccattg | acgtcaataa | tgacgtatgt | tcccatagta    240 |
| acgccaatag | ggactttcca | ttgacgtcaa | tgggtggact | atttacggta | aactgcccac    300 |
| ttggcagtac | atcaagtgta | tcatatgcca | agtacgcccc | ctattgacgt | caatgacggt    360 |
| aaatggcccg | cctggcatta | tgcccagtac | atgaccttat | gggactttcc | tacttggcag    420 |
| tacatctacg | tattagtcat | cgctattacc | atggtgatgc | ggttttggca | gtacatcaat    480 |
| gggcgtggat | agcggtttga | ctcacgggga | tttccaagtc | tccaccccat | tgacgtcaat    540 |
| gggagtttgt | tttggcacca | aaatcaacgg | gactttccaa | aatgtcgtaa | caactccgcc    600 |
| ccattgacgc | aaatgggcgg | taggcgtgta | cggtgggagg | tctatataag | cagagctctc    660 |
| tggctaacta | gagaacccac | tgcttactgg | cttatcgaaa | ttaatacgac | tcactatagg    720 |
| gagacccaag | ctggctagcc | accatggaga | cagacacact | cctgctatgg | gtactgctgc    780 |
| tctgggttcc | aggttccact | ggtgacgcgg | cccagccggc | caggcgcgcg | cgccgtacgt    840 |
| acgaagctta | cgtaagatct | tccggaatca | tcccagttga | ggaggagaac | ccggacttct    900 |
| ggaaccgcga | ggcagccgag | gccctgggtg | ccgccaagaa | gctgcagcct | gcacagacag    960 |
| ccgccaagaa | cctcatcatc | ttcctgggcg | atgggatggg | ggtgtctacg | gtgacagctg   1020 |
| ccaggatcct | aaaagggcag | aagaaggaca | aactggggcc | tgagatacc  | ctggccatgg   1080 |
| accgcttccc | atatgtggct | ctgtccaaga | catacaatgt | agacaaacat | gtgccagaca   1140 |
| gtggagccac | agccacggcc | tacctgtgcg | ggtcaaggg  | caacttccag | accattggct   1200 |
| tgagtgcagc | cgcccgcttt | aaccagtgca | acacgacacg | cggcaacgag | gtcatctccg   1260 |
| tgatgaatcg | ggccaagaaa | gcagggaagt | cagtgggagt | ggtaaccacc | acacgagtgc   1320 |
| agcacgcctc | gccagccggc | acctacgccc | acacggtgaa | ccgcaactgg | tactcggacg   1380 |
| ccgacgtgcc | tgcctcggcc | cgccaggagg | ggtgccagga | catcgctacg | cagctcatct   1440 |
| ccaacatgga | cattgacgtg | atcctaggtg | gaggccgaaa | gtacatgttt | cccatgggaa   1500 |
| ccccagaccc | tgagtaccca | gatgactaca | gccaaggtgg | gaccaggctg | gacgggaaga   1560 |
| atctggtgca | ggaatggctg | gcgaagcgcc | agggtgcccg | gtatgtgtgg | aaccgcactg   1620 |
| agctcatgca | ggcttccctg | gacccgtctg | tgacccatct | catgggtctc | tttgagcctg   1680 |
| gagacatgaa | atacgagatc | caccgagact | ccacactgga | ccctccctg  | atggagatga   1740 |
| cagaggctgc | cctgcgcctg | ctgagcagga | accccgcgg  | cttcttcctc | ttcgtggagg   1800 |
| gtggtcgcat | cgaccatggt | catcatgaaa | gcagggctta | ccgggcactg | actgagacga   1860 |
| tcatgttcga | cgacgccatt | gagagggcg  | ccagctcac  | cagcgaggag | gacacgctga   1920 |
| gcctcgtcac | tgccgaccac | tcccacgtct | tctccttcgg | aggctacccc | ctgcgaggga   1980 |
| gctccatctt | cgggctggcc | cctggcaagg | cccgggacag | gaaggcctac | acggtcctcc   2040 |

```
tatacggaaa cggtccaggc tatgtgctca aggacggcgc ccggccggat gttaccgaga    2100
gcgagagcgg gagccccgag tatcggcagc agtcagcagt gccctggac gaagagaccc    2160 acgcaggcga ggacgtggcg gtgttcgcgc gcggcccgca ggcgcacctg gttcacggcg    2220
tgcaggagca gaccttcata gcgcacgtca tggccttcgc cgcctgcctg gagccctaca    2280
ccgcctgcga cctggcgccc cccgccggca ccaccgacgc cgcgcacccg ggttatctcg    2340
aggaagcgct ctctctagat ctggaagttc tgttccaggg gccctggga tctaggatat     2400 acaagggtgt gatccaagct atccagaaat cagatgaagg ccacccattc agggcatatc    2460
tggaatctga agttgctata tctgaggagt tggttcagaa gtacagtaat tctgctcttg    2520
gtcatgtgaa ctgcacgata aaggaactca ggcgcctctt cttagttgat gatttagttg    2580
attctctgaa gtagtctaga agggcccgaa caaaaactca tctcagaaga ggatctgaat    2640
agcgccgtcg accatcatca tcatcatcat tgagtttaaa cccgctgatc agcctcgact    2700
gtgccttcta gttgccagcc atctgttgtt tgccccctcc ccgtgccttc cttgaccctg    2760
gaaggtgcca ctcccactgt cctttcctaa taaaatgagg aaattgcatc gcattgtctg    2820
agtaggtgtc attctattct ggggggtggg gtggggcagg acagcaaggg ggaggattgg    2880
gaagacaata gcaggcatgc tggggatgcg gtgggctcta tggcttctga ggcggaaaga    2940
accagctggg gctctagggg gtatccccac gcgccctgta gcggcgcatt aagcgcggcg    3000
ggtgtggtgg ttacgcgcag cgtgaccgct acacttgcca gcgccctagc gcccgctcct    3060
ttcgctttct tcccttcctt tctcgccacg ttcgccggct ttccccgtca agctctaaat    3120
cggggcatcc ctttagggtt ccgatttagt gctttacggc acctcgaccc caaaaaactt    3180
gattagggtg atggttcacg tagtgggcca tcgccctgat agacggtttt tcgccctttg    3240
acgttggagt ccacgttctt taatagtgga ctcttgttcc aaactggaac aacactcaac    3300
cctatctcgg tctattcttt tgatttataa gggattttgg ggatttcggc ctattggtta    3360
aaaaatgagc tgatttaaca aaaatttaac gcgaattaat tctgtggaat gtgtgtcagt    3420
tagggtgtgg aaagtcccca ggctccccag caggcagaag tatgcaaagc atgcatctca    3480
attagtcagc aaccaggtgt ggaaagtccc caggctcccc agcaggcaga agtatgcaaa    3540
gcatgcatct caattagtca gcaaccatag tcccgcccct aactccgccc atcccgcccc    3600
taactccgcc cagttccgcc cattctccgc cccatggctg actaattttt tttatttatg    3660
cagaggccga ggccgcctct gcctctgagc tattccagaa gtagtgagga ggcttttttg    3720
gaggcctagg cttttgcaaa aagctcccgg gagcttgtat atccattttc ggatctgatc    3780
agcacgtgtt gacaattaat catcggcata gtatatcggc atagtataat acgacaaggt    3840
gaggaactaa accatggcca agttgaccag tgccgttccg gtgctcaccg cgcgcgacgt    3900
cgccggagcg gtcgagttct ggaccgaccg gctcgggttc tcccgggact cgtggagga    3960 cgacttcgcc ggtgtggtcc gggacgacgt gaccctgttc atcagcgcgg tccaggacca    4020
ggtggtgccg gacaacaccc tggcctgggt gtgggtgcgc ggcctggacg agctgtacgc    4080
cgagtggtcg gaggtcgtgt ccacgaactt ccgggacgcc tccggccggg ccatgaccga    4140
gatcggcgag cagccgtggg gcggggagtt cgccctgcgc gacccggccg gcaactgcgt    4200
gcacttcgtg gccgaggagc aggactgaca cgtgctacga gatttcgatt ccaccgccgc    4260
cttctatgaa aggttgggct tcggaatcgt tttccgggac gccggctgga tgatcctcca    4320
gcgcggggat ctcatgctgg agttcttcgc ccaccccaac ttgtttattg cagcttataa    4380
```

```
tggttacaaa taaagcaata gcatcacaaa tttcacaaat aaagcatttt tttcactgca      4440
ttctagttgt ggtttgtcca aactcatcaa tgtatcttat catgtctgta taccgtcgac      4500
ctctagctag agcttggcgt aatcatggtc atagctgttt cctgtgtgaa attgttatcc      4560
gctcacaatt ccacacaaca tacgagccgg aagcataaag tgtaaagcct ggggtgccta      4620
atgagtgagc taactcacat taattgcgtt gcgctcactg cccgctttcc agtcgggaaa      4680
cctgtcgtgc cagctgcatt aatgaatcgg ccaacgcgcg gggagaggcg gtttgcgtat      4740
tgggcgctct tccgcttcct cgctcactga ctcgctgcgc tcggtcgttc ggctgcggcg      4800
agcggtatca gctcactcaa aggcggtaat acggttatcc acagaatcag gggataacgc      4860
aggaaagaac atgtgagcaa aaggccagca aaaggccagg aaccgtaaaa aggccgcgtt      4920
gctggcgttt ttccataggc tccgcccccc tgacgagcat cacaaaaatc gacgctcaag      4980
tcagaggtgg cgaaacccga caggactata agataccagg cgtttcccc ctggaagctc      5040 cctcgtgcgc tctcctgttc cgaccctgcc gcttaccgga tacctgtccg cctttctccc      5100
ttcgggaagc gtggcgcttt ctcaatgctc acgctgtagg tatctcagtt cggtgtaggt      5160
cgttcgctcc aagctgggct gtgtgcacga accccccgtt cagcccgacc gctgcgcctt      5220
atccggtaac tatcgtcttg agtccaaccc ggtaagacac gacttatcgc cactggcagc      5280
agccactggt aacaggatta gcagagcgag gtatgtaggc ggtgctacag agttcttgaa      5340
gtggtggcct aactacggct acactagaag gacagtattt ggtatctgcg ctctgctgaa      5400
gccagttacc ttcggaaaaa gagttggtag ctcttgatcc ggcaaacaaa ccaccgctgg      5460
tagcggtggt ttttttgttt gcaagcagca gattacgcgc agaaaaaaag gatctcaaga      5520
agatcctttg atcttttcta cggggtctga cgctcagtgg aacgaaaact cacgttaagg      5580
gattttggtc atgagattat caaaaaggat cttcacctag atccttttaa attaaaaatg      5640
aagttttaaa tcaatctaaa gtatatatga gtaaacttgg tctgacagtt accaatgctt      5700
aatcagtgag gcacctatct cagcgatctg tctatttcgt tcatccatag ttgcctgact      5760
ccccgtcgtg tagataacta cgatacggga gggcttacca tctggcccca gtgctgcaat      5820
gataccgcga gacccacgct caccggctcc agatttatca gcaataaacc agccagccgg      5880
aagggccgag cgcagaagtg gtcctgcaac tttatccgcc tccatccagt ctattaattg      5940
ttgccgggaa gctagagtaa gtagttcgcc agttaatagt ttgcgcaacg ttgttgccat      6000
tgctacaggc atcgtggtgt cacgctcgtc gtttggtatg gcttcattca gctccggttc      6060
ccaacgatca aggcgagtta catgatcccc catgttgtgc aaaaaagcgg ttagctcctt      6120
cggtcctccg atcgttgtca gaagtaagtt ggccgcagtg ttatcactca tggttatggc      6180
agcactgcat aattctctta ctgtcatgcc atccgtaaga tgcttttctg tgactggtga      6240
gtactcaacc aagtcattct gagaatagtg tatgcggcga ccgagttgct cttgcccggc      6300
gtcaatacgg gataataccg cgccacatag cagaacttta aaagtgctca tcattggaaa      6360
acgttcttcg gggcgaaaac tctcaaggat cttaccgctg ttgagatcca gttcgatgta      6420
acccactcgt gcacccaact gatcttcagc atcttttact ttcaccagcg tttctgggtg      6480
agcaaaaaca ggaaggcaaa atgccgcaaa aaagggaata agggcgacac ggaaatgttg      6540
aatactcata ctcttccttt ttcaatatta ttgaagcatt tatcagggtt attgtctcat      6600
gagcggatac atatttgaat gtatttagaa aaataaacaa ataggggttc cgcgcacatt      6660
tccccgaaaa gtgccacctg acgtcgacgg atcgggagat cgatctcccg atcccctatg      6720
gtcgactctc agtacaatct gctctgatgc cgcatagtta agccagtatc tgctccctgc      6780
```

```
ttgtgtgttg gaggtcgctg agtagtgcgc gagcaaaatt taagctacaa caaggcaagg    6840
cttgaccgac                                                            6850

<210> SEQ ID NO 12
<211> LENGTH: 20
<212> TYPE: DNA
<213> ORGANISM: Artificial Sequence
<220> FEATURE:
<223> OTHER INFORMATION: PCR primer mey35

<400> SEQUENCE: 12
tcacactggg gatgtggcag                                                 20

<210> SEQ ID NO 13
<211> LENGTH: 24
<212> TYPE: DNA
<213> ORGANISM: Artificial Sequence
<220> FEATURE:
<223> OTHER INFORMATION: PCR Primer mey 36

<400> SEQUENCE: 13
gccaccatgg gggcaggtgc cacc                                            24

<210> SEQ ID NO 14
<211> LENGTH: 18
<212> TYPE: DNA
<213> ORGANISM: Artificial Sequence
<220> FEATURE:
<223> OTHER INFORMATION: PCR primer mey71

<400> SEQUENCE: 14
gcagccccat cagtccgc                                                   18

<210> SEQ ID NO 15
<211> LENGTH: 5523
<212> TYPE: DNA
<213> ORGANISM: Artificial Sequence
<220> FEATURE:
<223> OTHER INFORMATION: Plasmid pcDNA3.1V5-His TOPO

<400> SEQUENCE: 15
gacggatcgg gagatctccc gatccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
```

```
ctgcttactg gcttatcgaa attaatacga ctcactatag ggagacccaa gctggctagt    900
taagcttggt accgagctcg gatccactag tccagtgtgg tggaattgcc cttaagggca    960
attctgcaga tatccagcac agtggcggcc gctcgagtct agagggcccg cggttcgaag   1020
gtaagcctat ccctaaccct ctcctcggtc tcgattctac gcgtaccggt catcatcacc   1080
atcaccattg agtttaaacc cgctgatcag cctcgactgt gccttctagt tgccagccat   1140
ctgttgtttg cccctccccc gtgccttcct tgaccctgga aggtgccact cccactgtcc   1200
tttcctaata aaatgaggaa attgcatcgc attgtctgag taggtgtcat tctattctgg   1260
ggggtggggt ggggcaggac agcaaggggg aggattggga agacaatagc aggcatgctg   1320
gggatgcggt gggctctatg gcttctgagg cggaaagaac cagctggggc tctagggggt   1380
atccccacgc gccctgtagc ggcgcattaa gcgcggcggg tgtggtggtt acgcgcagcg   1440
tgaccgctac acttgccagc gccctagcgc ccgctccttt cgctttcttc ccttcctttc   1500
tcgccacgtt cgccggcttt ccccgtcaag ctctaaatcg ggcatccct ttagggttcc    1560
gatttagtgc tttacggcac ctcgacccca aaaaacttga ttagggtgat ggttcacgta   1620
gtgggccatc gccctgatag acggtttttc gccctttgac gttggagtcc acgttcttta   1680
atagtggact cttgttccaa actggaacaa cactcaaccc tatctcggtc tattcttttg   1740
atttataagg gattttgggg atttcggcct attggttaaa aaatgagctg atttaacaaa   1800
aatttaacgc gaattaattc tgtggaatgt gtgtcagtta gggtgtggaa agtccccagg   1860
ctccccaggc aggcagaagt atgcaaagca tgcatctcaa ttagtcagca accaggtgtg   1920
gaaagtcccc aggctcccca gcaggcagaa gtatgcaaag catgcatctc aattagtcag   1980
caaccatagt cccgccccta actccgccca tcccgcccct aactccgccc agttccgccc   2040
attctccgcc ccatggctga ctaatttttt ttatttatgc agaggccgag gccgcctctg   2100
cctctgagct attccagaag tagtgaggag gcttttttgg aggcctaggc ttttgcaaaa   2160
agctcccggg agcttgtata tccatttttcg gatctgatca agagacagga tgaggatcgt   2220
ttcgcatgat tgaacaagat ggattgcacg caggttctcc ggccgcttgg gtggagaggc   2280
tattcggcta tgactgggca caacagacaa tcggctgctc tgatgccgcc gtgttccggc   2340
tgtcagcgca ggggcgcccg gttctttttg tcaagaccga cctgtccggt gccctgaatg   2400
aactgcagga cgaggcagcg cggctatcgt ggctggccac gacgggcgtt ccttgcgcag   2460
ctgtgctcga cgttgtcact gaagcgggaa gggactggct gctattgggc gaagtgccgg   2520
ggcaggatct cctgtcatct caccttgctc ctgccgagaa agtatccatc atggctgatg   2580
caatgcggcg gctgcatacg cttgatccgg ctacctgccc attcgaccac caagcgaaac   2640
atcgcatcga gcgagcacgt actcggatgg aagccggtct tgtcgatcag gatgatctgg   2700
acgaagagca tcagggctc gcgccagccg aactgttcgc caggctcaag gcgcgcatgc   2760
ccgacggcga ggatctcgtc gtgacccatg gcgatgcctg cttgccgaat atcatggtgg   2820
aaaatggccg cttttctgga ttcatcgact gtggccggct gggtgtggcg gaccgctatc   2880
aggacatagc gttggctacc cgtgatattg ctgaagagct tggcggcgaa tgggctgacc   2940
gcttcctcgt gctttacggt atcgccgctc ccgattcgca gcgcatcgcc ttctatcgcc   3000
ttcttgacga gttcttctga gcgggactct ggggttcgcg aaatgaccga ccaagcgacg   3060
cccaacctgc catcacgaga tttcgattcc accgccgcct tctatgaaag gttgggcttc   3120
ggaatcgttt tccgggacgc cggctggatg atcctccagc gcggggatct catgctggag   3180
ttcttcgccc accccaactt gtttattgca gcttataatg gttacaaata aagcaatagc   3240
```

```
atcacaaatt tcacaaataa agcattttt tcactgcatt ctagttgtgg tttgtccaaa    3300
ctcatcaatg tatcttatca tgtctgtata ccgtcgacct ctagctagag cttggcgtaa    3360
tcatggtcat agctgtttcc tgtgtgaaat tgttatccgc tcacaattcc acacaacata    3420
cgagccggaa gcataaagtg taaagcctgg ggtgcctaat gagtgagcta actcacatta    3480
attgcgttgc gctcactgcc cgctttccag tcgggaaacc tgtcgtgcca gctgcattaa    3540
tgaatcggcc aacgcgcggg gagaggcggt ttgcgtattg ggcgctcttc cgcttcctcg    3600
ctcactgact cgctgcgctc ggtcgttcgg ctgcggcgag cggtatcagc tcactcaaag    3660
gcggtaatac ggttatccac agaatcaggg gataacgcag gaaagaacat gtgagcaaaa    3720
ggccagcaaa aggccaggaa ccgtaaaaag gccgcgttgc tggcgttttt ccataggctc    3780
cgcccccctg acgagcatca caaaaatcga cgctcaagtc agaggtggcg aaacccgaca    3840
ggactataaa gataccaggc gtttccccct ggaagctccc tcgtgcgctc tcctgttccg    3900
accctgccgc ttaccggata cctgtccgcc tttctccctt cgggaagcgt ggcgctttct    3960
caatgctcac gctgtaggta tctcagttcg gtgtaggtcg ttcgctccaa gctgggctgt    4020
gtgcacgaac cccccgttca gcccgaccgc tgcgccttat ccggtaacta tcgtcttgag    4080
tccaacccgg taagacacga cttatcgcca ctggcagcag ccactggtaa caggattagc    4140
agagcgaggt atgtaggcgg tgctacagag ttcttgaagt ggtggcctaa ctacggctac    4200
actagaagga cagtatttgg tatctgcgct ctgctgaagc cagttacctt cggaaaaaga    4260
gttggtagct cttgatccgg caaacaaacc accgctggta gcggtggttt ttttgtttgc    4320
aagcagcaga ttacgcgcag aaaaaaagga tctcaagaag atcctttgat cttttctacg    4380
gggtctgacg ctcagtggaa cgaaaactca cgttaaggga ttttggtcat gagattatca    4440
aaaaggatct tcacctagat ccttttaaat taaaaatgaa gttttaaatc aatctaaagt    4500
atatatgagt aaacttggtc tgacagttac caatgcttaa tcagtgaggc acctatctca    4560
gcgatctgtc tatttcgttc atccatagtt gcctgactcc ccgtcgtgta gataactacg    4620
atacgggagg gcttaccatc tggccccagt gctgcaatga taccgcgaga cccacgctca    4680
ccggctccag atttatcagc aataaaccag ccagccggaa gggccgagcg cagaagtggt    4740
cctgcaactt tatccgcctc catccagtct attaattgtt gccgggaagc tagagtaagt    4800
agttcgccag ttaatagttt gcgcaacgtt gttgccattg ctacaggcat cgtggtgtca    4860
cgctcgtcgt ttggtatggc ttcattcagc tccggttccc aacgatcaag gcgagttaca    4920
tgatccccca tgttgtgcaa aaaagcggtt agctccttcg gtcctccgat cgttgtcaga    4980
agtaagttgg ccgcagtgtt atcactcatg gttatggcag cactgcataa ttctcttact    5040
gtcatgccat ccgtaagatg cttttctgtg actggtgagt actcaaccaa gtcattctga    5100
gaatagtgta tgcggcgacc gagttgctct tgcccggcgt caatacggga taataccgcg    5160
ccacatagca gaactttaaa agtgctcatc attggaaaac gttcttcggg gcgaaaactc    5220
tcaaggatct taccgctgtt gagatccagt tcgatgtaac ccactcgtgc acccaactga    5280
tcttcagcat cttttacttt caccagcgtt tctgggtgag caaaaacagg aaggcaaaat    5340
gccgcaaaaa agggaataag ggcgacacgg aaatgttgaa tactcatact cttcctttt    5400 caatattatt gaagcattta tcagggttat tgtctcatga gcggatacat atttgaatgt    5460
atttagaaaa ataaacaaat aggggttccg cgcacatttc cccgaaaagt gccacctgac    5520
gtc                                                                  5523
```

```
<210> SEQ ID NO 16
<211> LENGTH: 13612
<212> TYPE: DNA
<213> ORGANISM: Artificial Sequence
<220> FEATURE:
<223> OTHER INFORMATION: Plasmid pcDNA3.1 hp75 Nr.16
<220> FEATURE:
<221> NAME/KEY: CDS
<222> LOCATION: (40)..(1320)
<223> OTHER INFORMATION: human p75 sequence

<400> SEQUENCE: 16
```

| | | | | | | | | | | | | | | | | |
|---|---|---|---|---|---|---|---|---|---|---|---|---|---|---|---|---|
| gatccactag | tccagtgtgg | tggaattgcc | cttgccacc | atg | ggg | gca | ggt | gcc | | | | | | | | 54 |
| | | | | Met | Gly | Ala | Gly | Ala | | | | | | | | |
| | | | | 1 | | | | 5 | | | | | | | | |
| acc | ggc | cgc | gcc | atg | gac | ggg | ccg | cgc | ctg | ctg | ctg | ttg | ctg | ctt | ctg | 102 |
| Thr | Gly | Arg | Ala | Met | Asp | Gly | Pro | Arg | Leu | Leu | Leu | Leu | Leu | Leu | Leu | |
| | | | | 10 | | | | 15 | | | | 20 | | | | |
| ggg | gtg | tcc | ctt | gga | ggt | gcc | aag | gag | gca | tgc | ccc | aca | ggc | ctg | tac | 150 |
| Gly | Val | Ser | Leu | Gly | Gly | Ala | Lys | Glu | Ala | Cys | Pro | Thr | Gly | Leu | Tyr | |
| | | 25 | | | | 30 | | | | 35 | | | | | | |
| acg | cac | agc | ggt | gag | tgc | tgc | aaa | gcc | tgc | aac | ctg | ggc | gag | ggt | gtg | 198 |
| Thr | His | Ser | Gly | Glu | Cys | Cys | Lys | Ala | Cys | Asn | Leu | Gly | Glu | Gly | Val | |
| | 40 | | | | | 45 | | | | | 50 | | | | | |
| gcc | cag | cct | tgt | gga | gcc | aac | cag | acc | gtg | tgt | gag | ccc | tgc | ctg | gac | 246 |
| Ala | Gln | Pro | Cys | Gly | Ala | Asn | Gln | Thr | Val | Cys | Glu | Pro | Cys | Leu | Asp | |
| 55 | | | | | 60 | | | | | 65 | | | | | | |
| agc | gtg | acg | ttc | tcc | gac | gtg | gtg | agc | gcg | acc | gag | ccg | tgc | aag | ccg | 294 |
| Ser | Val | Thr | Phe | Ser | Asp | Val | Val | Ser | Ala | Thr | Glu | Pro | Cys | Lys | Pro | |
| 70 | | | | 75 | | | | | 80 | | | | | 85 | | |
| tgc | acc | gag | tgc | gtg | ggg | ctc | cag | agc | atg | tcg | gcg | ccg | tgc | gtg | gag | 342 |
| Cys | Thr | Glu | Cys | Val | Gly | Leu | Gln | Ser | Met | Ser | Ala | Pro | Cys | Val | Glu | |
| | | | 90 | | | | | 95 | | | | 100 | | | | |
| gcc | gac | gac | gcc | gtg | tgc | cgc | tgc | gcc | tac | ggc | tac | tac | cag | gat | gag | 390 |
| Ala | Asp | Asp | Ala | Val | Cys | Arg | Cys | Ala | Tyr | Gly | Tyr | Tyr | Gln | Asp | Glu | |
| | | 105 | | | | 110 | | | | | 115 | | | | | |
| acg | act | ggg | cgc | tgc | gag | gcg | tgc | cgc | gtg | tgc | gag | gcg | ggc | tcg | ggc | 438 |
| Thr | Thr | Gly | Arg | Cys | Glu | Ala | Cys | Arg | Val | Cys | Glu | Ala | Gly | Ser | Gly | |
| | 120 | | | | | 125 | | | | | 130 | | | | | |
| ctc | gtg | ttc | tcc | tgc | cag | gac | aag | cag | aac | acc | gtg | tgc | gag | gag | tgc | 486 |
| Leu | Val | Phe | Ser | Cys | Gln | Asp | Lys | Gln | Asn | Thr | Val | Cys | Glu | Glu | Cys | |
| 135 | | | | | 140 | | | | | 145 | | | | | | |
| ccc | gac | ggc | acg | tat | tcc | gac | gag | gcc | aac | cac | gtg | gac | ccg | tgc | ctg | 534 |
| Pro | Asp | Gly | Thr | Tyr | Ser | Asp | Glu | Ala | Asn | His | Val | Asp | Pro | Cys | Leu | |
| 150 | | | | 155 | | | | | 160 | | | | | 165 | | |
| ccc | tgc | acc | gtg | tgc | gag | gac | acc | gag | cgc | cag | ctc | cgc | gag | tgc | aca | 582 |
| Pro | Cys | Thr | Val | Cys | Glu | Asp | Thr | Glu | Arg | Gln | Leu | Arg | Glu | Cys | Thr | |
| | | | 170 | | | | | 175 | | | | 180 | | | | |
| cgc | tgg | gcc | gac | gcc | gag | tgc | gag | gag | atc | cct | ggc | cgt | tgg | att | aca | 630 |
| Arg | Trp | Ala | Asp | Ala | Glu | Cys | Glu | Glu | Ile | Pro | Gly | Arg | Trp | Ile | Thr | |
| | | 185 | | | | 190 | | | | | 195 | | | | | |
| cgg | tcc | aca | ccc | cca | gag | ggc | tcg | gac | agc | aca | gcc | ccc | agc | acc | cag | 678 |
| Arg | Ser | Thr | Pro | Pro | Glu | Gly | Ser | Asp | Ser | Thr | Ala | Pro | Ser | Thr | Gln | |
| | 200 | | | | | 205 | | | | | 210 | | | | | |
| gag | cct | gag | gca | cct | cca | gaa | caa | gac | ctc | ata | gcc | agc | acg | gtg | gca | 726 |
| Glu | Pro | Glu | Ala | Pro | Pro | Glu | Gln | Asp | Leu | Ile | Ala | Ser | Thr | Val | Ala | |
| 215 | | | | | 220 | | | | | 225 | | | | | | |
| ggt | gtg | gtg | acc | aca | gtg | atg | ggc | agc | tcc | cag | ccc | gtg | gtg | acc | cga | 774 |
| Gly | Val | Val | Thr | Thr | Val | Met | Gly | Ser | Ser | Gln | Pro | Val | Val | Thr | Arg | |
| 230 | | | | 235 | | | | | 240 | | | | | 245 | | |
| ggc | acc | acc | gac | aac | ctc | atc | cct | gtc | tat | tgc | tcc | atc | ctg | gct | gct | 822 |

-continued

```
                Gly Thr Thr Asp Asn Leu Ile Pro Val Tyr Cys Ser Ile Leu Ala Ala
                                250                 255                 260 gtg gtt gtg ggt ctt gtg gcc tac ata gcc ttc aag agg tgg aac agc           870
Val Val Val Gly Leu Val Ala Tyr Ile Ala Phe Lys Arg Trp Asn Ser
            265                 270                 275 tgc aag cag aac aag caa gga gcc aac agc cgg cca gtg aac cag acg           918
Cys Lys Gln Asn Lys Gln Gly Ala Asn Ser Arg Pro Val Asn Gln Thr
        280                 285                 290 ccc cca cca gag gga gaa aaa ctc cac agc gac agt ggc atc tcc gtg           966
Pro Pro Pro Glu Gly Glu Lys Leu His Ser Asp Ser Gly Ile Ser Val
    295                 300                 305 gac agc cag agc ctg cat gac cag cag ccc cac acg cag aca gcc tcg          1014
Asp Ser Gln Ser Leu His Asp Gln Gln Pro His Thr Gln Thr Ala Ser
310                 315                 320                 325 ggc cag gcc ctc aag ggt gac gga ggc ctc tac agc agc ctg ccc cca          1062
Gly Gln Ala Leu Lys Gly Asp Gly Gly Leu Tyr Ser Ser Leu Pro Pro
                330                 335                 340 gcc aag cgg gag gag gtg gag aag ctt ctc aac ggc tct gcg ggg gac          1110
Ala Lys Arg Glu Glu Val Glu Lys Leu Leu Asn Gly Ser Ala Gly Asp
            345                 350                 355 acc tgg cgg cac ctg gcg ggc gag ctg ggc tac cag ccc gag cac ata          1158
Thr Trp Arg His Leu Ala Gly Glu Leu Gly Tyr Gln Pro Glu His Ile
        360                 365                 370 gac tcc ttt acc cat gag gcc tgc ccc gtt cgc gcc ctg ctt gca agc          1206
Asp Ser Phe Thr His Glu Ala Cys Pro Val Arg Ala Leu Leu Ala Ser
    375                 380                 385 tgg gcc acc cag gac agc gcc aca ctg gac gcc ctc ctg gcc gcc ctg          1254
Trp Ala Thr Gln Asp Ser Ala Thr Leu Asp Ala Leu Leu Ala Ala Leu
390                 395                 400                 405 cgc cgc atc cag cga gcc gac ctc gtg gag agt ctg tgc agt gag tcc          1302
Arg Arg Ile Gln Arg Ala Asp Leu Val Glu Ser Leu Cys Ser Glu Ser
                410                 415                 420 act gcc aca tcc cca gtg tgaaagggca attctgcaga tatccagcac                 1350
Thr Ala Thr Ser Pro Val
            425 agtggcggcc gctcgagtct agagggcccg cggttcgaag gtaagcctat ccctaaccct        1410 ctcctcggtc tcgattctac gcgtaccggt catcatcacc atcaccattg agtttaaacc        1470 cgctgatcag cctcgactgt gccttctagt tgccagccat ctgttgtttg cccctccccc        1530 gtgccttcct tgaccctgga aggtgccact cccactgtcc tttcctaata aaatgaggaa        1590 attgcatcgc attgtctgag taggtgtcat tctattctgg ggggtggggt gggcaggac         1650 agcaagggg aggattggga agacaatagc aggcatgctg gggatgcggt gggctctatg         1710 gcttctgagg cggaaagaac cagctggggc tctaggggt atccccacgc gccctgtagc         1770 ggcgcattaa gcgcggcggg tgtggtggtt acgcgcagcg tgaccgctac acttgccagc        1830 gccctagcgc ccgctccttt cgctttcttc ccttcctttc tcgccacgtt cgccggcttt        1890 ccccgtcaag ctctaaatcg ggcatccct ttagggttcc gatttagtgc tttacggcac        1950 ctcgacccca aaaaacttga ttagggtgat ggttcacgta gtgggccatc gccctgatag        2010 acggttttc gccctttgac gttggagtcc acgttcttta atagtggact cttgttccaa        2070 actggaacaa cactcaaccc tatctcggtc tattcttttg atttataagg gattttgggg        2130 atttcggcct attggttaaa aaatgagctg atttaacaaa aatttaacgc gaattaattc        2190 tgtggaatgt gtgtcagtta gggtgtggaa agtccccagg ctccccaggc aggcagaagt        2250 atgcaaagca tgcatctcaa ttagtcagca accaggtgtg gaaagtcccc aggctcccca       2310
```

```
gcaggcagaa gtatgcaaag catgcatctc aattagtcag caaccatagt cccgcccta    2370 actccgccca tcccgcccct aactccgccc agttccgccc attctccgcc ccatggctga    2430 ctaattttt ttatttatgc agaggccgag gccgcctctg cctctgagct attccagaag    2490
tagtgaggag ctttttttgg aggcctaggc ttttgcaaaa agctcccggg agcttgtata    2550
tccattttcg gatctgatca agagacagga tgaggatcgt ttcgcatgat tgaacaagat    2610
ggattgcacg caggttctcc ggccgcttgg gtggagaggc tattcggcta tgactgggca    2670
caacagacaa tcggctgctc tgatgccgcc gtgttccggc tgtcagcgca ggggcgcccg    2730 gttcttttg tcaagaccga cctgtccggt gccctgaatg aactgcagga cgaggcagcg    2790
cggctatcgt ggctggccac gacgggcgtt ccttgcgcag ctgtgctcga cgttgtcact    2850
gaagcgggaa gggactggct gctattgggc gaagtgccgg ggcaggatct cctgtcatct    2910
caccttgctc ctgccgagaa agtatccatc atggctgatg caatgcggcg gctgcatacg    2970
cttgatccgg ctacctgccc attcgaccac caagcgaaac atcgcatcga gcgagcacgt    3030
actcggatgg aagccggtct tgtcgatcag gatgatctgg acgaagagca tcaggggctc    3090
gcgccagccg aactgttcgc caggctcaag gcgcgcatgc ccgacggcga ggatctcgtc    3150
gtgacccatg gcgatgcctg cttgccgaat atcatggtgg aaaatggccg cttttctgga    3210
ttcatcgact gtggccggct gggtgtggcg gaccgctatc aggacatagc gttggctacc    3270
cgtgatattg ctgaagagct tggcggcgaa tgggctgacc gcttcctcgt gctttacggt    3330
atcgccgctc ccgattcgca gcgcatcgcc ttctatcgcc ttcttgacga gttcttctga    3390
gcgggactct ggggttcgcg aaatgaccga ccaagcgacg cccaacctgc catcacgaga    3450
tttcgattcc accgccgcct tctatgaaag gttgggcttc ggaatcgttt tccgggacgc    3510
cggctggatg atcctccagc gcggggatct catgctggag ttcttcgccc accccaactt    3570
gtttattgca gcttataatg gttacaaata agcaatagc atcacaaatt cacaaataa     3630 agcatttttt tcactgcatt ctagttgtgg tttgtccaaa ctcatcaatg tatcttatca    3690
tgtctgtata ccgtcgacct ctagctagag cttggcgtaa tcatggtcat agctgtttcc    3750
tgtgtgaaat tgttatccgc tcacaattcc acacaacata cgagccggaa gcataaagtg    3810
taaagcctgg ggtgcctaat gagtgagcta actcacatta attgcgttgc gctcactgcc    3870
cgctttccag tcgggaaacc tgtcgtgcca gctgcattaa tgaatcggcc aacgcgcggg    3930
gagaggcggt ttgcgtattg ggcgctcttc cgcttcctcg ctcactgact cgctgcgctc    3990
ggtcgttcgg ctgcggcgag cggtatcagc tcactcaaag gcggtaatac ggttatccac    4050
agaatcaggg gataacgcag gaaagaacat gtgagcaaaa ggccagcaaa aggccaggaa    4110
ccgtaaaaag gccgcgttgc tggcgttttt ccataggctc cgcccccctg acgagcatca    4170
caaaaatcga cgctcaagtc agaggtggcg aaacccgaca ggactataaa gataccaggc    4230
gtttccccct ggaagctccc tcgtgcgctc tcctgttccg accctgccgc ttaccggata    4290
cctgtccgcc tttctccctt cgggaagcgt ggcgctttct caatgctcac gctgtaggta    4350
tctcagttcg gtgtaggtcg ttcgctccaa gctgggctgt gtgcacgaac cccccgttca    4410
gcccgaccgc tgcgccttat ccggtaacta tcgtcttgag tccaacccgg taagacacga    4470
cttatcgcca ctggcagcag ccactggtaa caggattagc agagcgaggt atgtaggcgg    4530
tgctacagag ttcttgaagt ggtggcctaa ctacggctac actagaagga cagtatttgg    4590
tatctgcgct ctgctgaagc cagttacctt cggaaaaaga gttggtagct cttgatccgg    4650
caaacaaacc accgctggta gcggtggttt ttttgtttgc aagcagcaga ttacgcgcag    4710
```

```
aaaaaaagga tctcaagaag atcctttgat cttttctacg gggtctgacg ctcagtggaa    4770
cgaaaactca cgttaaggga ttttggtcat gagattatca aaaaggatct tcacctagat    4830
ccttttaaat taaaaatgaa gttttaaatc aatctaaagt atatatgagt aaacttggtc    4890
tgacagttac caatgcttaa tcagtgaggc acctatctca gcgatctgtc tatttcgttc    4950
atccatagtt gcctgactcc ccgtcgtgta gataactacg atacgggagg gcttaccatc    5010
tggcccagt gctgcaatga taccgcgaga cccacgctca ccggctccag atttatcagc     5070
aataaaccag ccagccggaa gggccgagcg cagaagtggt cctgcaactt tatccgcctc    5130
catccagtct attaattgtt gccgggaagc tagagtaagt agttcgccag ttaatagttt    5190
gcgcaacgtt gttgccattg ctacaggcat cgtggtgtca cgctcgtcgt ttggtatggc    5250
ttcattcagc tccggttccc aacgatcaag gcgagttaca tgatccccca tgttgtgcaa    5310
aaaagcggtt agctccttcg gtcctccgat cgttgtcaga agtaagttgg ccgcagtgtt    5370
atcactcatg gttatggcag cactgcataa ttctcttact gtcatgccat ccgtaagatg    5430
cttttctgtg actggtgagt actcaaccaa gtcattctga atagtgta tgcggcgacc      5490
gagttgctct tgcccggcgt caatacggga taataccgcg ccacatagca gaactttaaa    5550
agtgctcatc attggaaaac gttcttcggg gcgaaaactc tcaaggatct taccgctgtt    5610
gagatccagt tcgatgtaac ccactcgtgc acccaactga tcttcagcat cttttacttt    5670
caccagcgtt tctgggtgag caaaaacagg aaggcaaaat gccgcaaaaa agggaataag    5730
ggcgacacgg aaatgttgaa tactcatact cttcctttt caatattatt gaagcattta     5790
tcagggttat tgtctcatga gcggatacat atttgaatgt atttagaaaa ataaacaaat    5850
aggggttccg cgcacatttc cccgaaaagt gccacctgac gtcgggagga tctcccgatc    5910
ccctatggtc gactctcagt acaatctgct ctgatgccgc atagttaagc cagtatctgc    5970
tccctgcttg tgtgttggag gtcgctgagt agtgcgcgag caaaatttaa gctacaacaa    6030
ggcaaggctt gaccgacaat tgcatgaaga atctgcttag ggttaggcgt tttgcgctgc    6090
ttcgcgatgt acgggccaga tatacgcgtt gacattgatt attgactagt tattaatagt    6150
aatcaattac ggggtcatta gttcatagcc catatatgga gttccgcgtt acataactta    6210
cggtaaatgg cccgcctggc tgaccgccca acgacccccg cccattgacg tcaataatga    6270
cgtatgttcc catagtaacg ccaatagga ctttccattg acgtcaatgg gtggactatt     6330
tacggtaaac tgcccacttg gcagtacatc aagtgtatca tatgccaagt acgcccccta    6390
ttgacgtcaa tgacggtaaa tggcccgcct ggcattatgc ccagtacatg accttatggg    6450
actttcctac ttggcagtac atctacgtat tagtcatcgc tattaccatg gtgatgcggt    6510
tttggcagta catcaatggg cgtggatagc ggtttgactc acggggattt ccaagtctcc    6570
accccattga cgtcaatggg agtttgtttt ggcaccaaaa tcaacgggac tttccaaaat    6630
gtcgtaacaa ctccgcccca ttgacgcaaa tgggcggtag gcgtgtacgg tgggaggtct    6690
atataagcag agctctctgg ctaactagag aacccactgc ttactggctt atcgaaatta    6750
atacgactca ctatagggag acccaagctg gctagttaag cttggtaccg agctcggatc    6810
cactagtcca gtgtggtgga attgcccttg ccaccatggg ggcaggtgcc accggccgcg    6870
ccatggacgg gccgcgcctg ctgctgttgc tgcttctggg ggtgtccctt ggaggtgcca    6930
aggaggcatg cccacaggc ctgtacacgc acagcggtga gtgctgcaaa gcctgcaacc     6990
tgggcgaggg tgtggcccag ccttgtggag ccaaccagac cgtgtgtgag ccctgcctgg    7050
```

```
acagcgtgac gttctccgac gtggtgagcg cgaccgagcc gtgcaagccg tgcaccgagt     7110
gcgtggggct ccagagcatg tcggcgccgt gcgtggaggc cgacgacgcc gtgtgccgct     7170
gcgcctacgg ctactaccag gatgagacga ctgggcgctg cgaggcgtgc cgcgtgtgcg     7230
aggcgggctc gggcctcgtg ttctcctgcc aggacaagca gaacaccgtg tgcgaggagt     7290
gccccgacgg cacgtattcc gacgaggcca accacgtgga cccgtgcctg ccctgcaccg     7350
tgtgcgagga caccgagcgc cagctccgcg agtgcacacg ctgggccgac gccgagtgcg     7410
aggagatccc tggccgttgg attacacggt ccacaccccc agagggctcg acagcacag     7470 cccccagcac ccaggagcct gaggcacctc cagaacaaga cctcatagcc agcacggtgg     7530
caggtgtggt gaccacagtg atgggcagct cccagcccgt ggtgacccga ggcaccaccg     7590
acaacctcat ccctgtctat tgctccatcc tggctgctgt ggttgtgggt cttgtggcct     7650
acatagcctt caagaggtgg aacagctgca agcagaacaa gcaaggagcc aacagccggc     7710
cagtgaacca gacgccccca ccagagggag aaaaactcca cagcgacagt ggcatctccg     7770
tggacagcca gagcctgcat gaccagcagc cccacacgcg acagcctcg ggccaggccc     7830 tcaagggtga cggaggcctc tacagcagcc tgccccagc caagcgggag gaggtggaga     7890
agcttctcaa cggctctgcg ggggacacct ggcggcacct ggcgggcgag ctgggctacc     7950
agcccgagca catagactcc tttacccatg aggcctgccc cgttcgcgcc ctgcttgcaa     8010
gctgggccac ccaggacagc gccacactgg acgccctcct ggccgccctg cgccgcatcc     8070
agcgagccga cctcgtggag agtctgtgca gtgagtccac tgccacatcc ccagtgtgaa     8130
agggcaattc tgcagatatc cagcacagtg gcggccgctc gagtctagag ggcccgcggt     8190
tcgaaggtaa gcctatccct aaccctctcc tcggtctcga ttctacgcgt accggtcatc     8250
atcaccatca ccattgagtt taaaaccgct gatcagcctc gactgtgcct tctagttgcc     8310
agccatctgt tgtttgcccc tcccccgtgc cttccttgac cctggaaggt gccactccca     8370
ctgtcctttc ctaataaaat gaggaaattg catcgcattg tctgagtagg tgtcattcta     8430
ttctgggggg tggggtgggg caggacagca agggggagga ttgggaagac aatagcaggc     8490
atgctgggga tgcggtgggc tctatggctt ctgaggcgga agaaccagc tggggctcta     8550 gggggtatcc ccacgcgccc tgtagcggcg cattaagcgc ggcgggtgtg tggttacgc     8610 gcagcgtgac cgctacactt gccagcgccc tagcgcccgc tccttcgct tcttcccctt     8670 cctttctcgc cacgttcgcc ggctttcccc gtcaagctct aaatcggggc atccctttag     8730
ggttccgatt tagtgcttta cggcacctcg accccaaaaa acttgattag ggtgatggtt     8790
cacgtagtgg gccatcgccc tgatagacgg ttttttcgcc tttgacgttg gagtccacgt     8850
tctttaatag tggactcttg ttccaaactg gaacaacact caaccctatc tcggtctatt     8910
cttttgattt ataagggatt tgggggattt cggcctattg gttaaaaaat gagctgattt     8970
aacaaaaatt taacgcgaat taattctgtg gaatgtgtgt cagttagggt gtggaaagtc     9030
cccaggctcc ccaggcaggc agaagtatgc aaagcatgca tctcaattag tcagcaacca     9090
ggtgtggaaa gtccccaggc tccccagcag gcagaagtat gcaaagcatg catctcaatt     9150
agtcagcaac catagtcccg cccctaactc cgcccatccc gcccctaact ccgcccagtt     9210
ccgcccattc tccgccccat ggctgactaa tttttttat ttatgcagag gccgaggccg     9270
cctctgcctc tgagctattc cagaagtagt gaggaggctt ttttggaggc ctaggctttt     9330
gcaaaaagct cccgggagct tgtatatcca ttttcggatc tgatcaagag acaggatgag     9390
gatcgtttcg catgattgaa caagatggat tgcacgcagg ttctccggcc gcttgggtgg     9450
```

```
agaggctatt cggctatgac tgggcacaac agacaatcgg ctgctctgat gccgccgtgt   9510
tccggctgtc agcgcagggg cgcccggttc tttttgtcaa gaccgacctg tccggtgccc   9570
tgaatgaact gcaggacgag gcagcgcggc tatcgtggct ggccacgacg ggcgttcctt   9630
gcgcagctgt gctcgacgtt gtcactgaag cgggaaggga ctggctgcta ttgggcgaag   9690
tgccggggca ggatctcctg tcatctcacc ttgctcctgc cgagaaagta tccatcatgg   9750
ctgatgcaat gcggcggctg catacgcttg atccggctac ctgcccattc gaccaccaag   9810
cgaaacatcg catcgagcga gcacgtactc ggatggaagc cggtcttgtc gatcaggatg   9870
atctggacga gagcatcag gggctcgcgc cagccgaact gttcgccagg ctcaaggcgc   9930
gcatgcccga cggcgaggat ctcgtcgtga cccatggcga tgcctgcttg ccgaatatca   9990
tggtggaaaa tggccgcttt tctggattca tcgactgtgg ccggctgggt gtggcggacc  10050
gctatcagga catagcgttg gctacccgtg atattgctga agagcttggc ggcgaatggg  10110
ctgaccgctt cctcgtgctt tacggtatcg ccgctcccga ttcgcagcgc atcgccttct  10170
atcgccttct tgacgagttc ttctgagcgg gactctgggg ttcgcgaaat gaccgaccaa  10230
gcgacgccca acctgccatc acgagatttc gattccaccg ccgccttcta tgaaaggttg  10290
ggcttcggaa tcgttttccg ggacgccggc tggatgatcc tccagcgcgg ggatctcatg  10350
ctggagttct tcgcccaccc caacttgttt attgcagctt ataatggtta caaataaagc  10410
aatagcatca caaatttcac aaataaagca tttttttcac tgcattctag ttgtggtttg  10470
tccaaactca tcaatgtatc ttatcatgtc tgtataccgt cgacctctag ctagagcttg  10530
gcgtaatcat ggtcatagct gtttcctgtg tgaaattgtt atccgctcac aattccacac  10590
aacatacgag ccggaagcat aaagtgtaaa gcctggggtg cctaatgagt gagctaactc  10650
acattaattg cgttgcgctc actgcccgct ttccagtcgg gaaacctgtc gtgccagctg  10710
cattaatgaa tcggccaacg cgcggggaga ggcggtttgc gtattgggcg ctcttccgct  10770
tcctcgctca ctgactcgct gcgctcggtc gttcggctgc ggcgagcggt atcagctcac  10830
tcaaaggcgg taatacggtt atccacagaa tcaggggata acgcaggaaa gaacatgtga  10890
gcaaaaggcc agcaaaaggc caggaaccgt aaaaaggccg cgttgctggc gttttttcat  10950
aggctccgcc cccctgacga gcatcacaaa aatcgacgct caagtcagag gtggcgaaac  11010
ccgacaggac tataaagata ccaggcgttt ccccctggaa gctccctcgt gcgctctcct  11070
gttccgaccc tgccgcttac cggatacctg tccgcctttc tcccttcggg aagcgtggcg  11130
ctttctcaat gctcacgctg taggtatctc agttcggtgt aggtcgttcg ctccaagctg  11190
ggctgtgtgc acgaaccccc cgttcagccc gaccgctgcg ccttatccgg taactatcgt  11250
cttgagtcca acccggtaag acacgactta tcgccactgg cagcagccac tggtaacagg  11310
attagcagag cgaggtatgt aggcggtgct acagagttct tgaagtggtg gcctaactac  11370
ggctacacta aaggacagt atttggtatc tgcgctctgc tgaagccagt taccttcgga  11430
aaaagagttg gtagctcttg atccggcaaa caaaccaccg ctggtagcgg tggtttttt   11490
gtttgcaagc agcagattac gcgcagaaaa aaaggatctc aagaagatcc tttgatcttt  11550
tctacggggt ctgacgctca gtggaacgaa aactcacgtt aagggatttt ggtcatgaga  11610
ttatcaaaaa ggatcttcac ctagatcctt ttaaattaaa aatgaagttt taaatcaatc  11670
taaagtatat atgagtaaac ttggtctgac agttaccaat gcttaatcag tgaggcacct  11730
atctcagcga tctgtctatt tcgttcatcc atagttgcct gactccccgt cgtgtagata  11790
```

```
actacgatac gggagggctt accatctggc cccagtgctg caatgatacc gcgagaccca    11850
cgctcaccgg ctccagattt atcagcaata accagccag ccggaagggc cgagcgcaga     11910
agtggtcctg caactttatc cgcctccatc cagtctatta attgttgccg ggaagctaga    11970
gtaagtagtt cgccagttaa tagtttgcgc aacgttgttg ccattgctac aggcatcgtg    12030
gtgtcacgct cgtcgtttgg tatggcttca ttcagctccg gttcccaacg atcaaggcga    12090
gttacatgat cccccatgtt gtgcaaaaaa gcggttagct ccttcggtcc tccgatcgtt    12150
gtcagaagta agttggccgc agtgttatca ctcatggtta tggcagcact gcataattct    12210
cttactgtca tgccatccgt aagatgcttt tctgtgactg gtgagtactc aaccaagtca    12270
ttctgagaat agtgtatgcg gcgaccgagt tgctcttgcc cggcgtcaat acgggataat    12330
accgcgccac atagcagaac tttaaaagtg ctcatcattg gaaaacgttc ttcggggcga    12390
aaactctcaa ggatcttacc gctgttgaga tccagttcga tgtaacccac tcgtgcaccc    12450
aactgatctt cagcatcttt tactttcacc agcgtttctg ggtgagcaaa aacaggaagg    12510
caaaatgccg caaaaaaggg aataagggcg acacggaaat gttgaatact catactcttc    12570
cttttcaat attattgaag catttatcag ggttattgtc tcatgagcgg atacatattt      12630
gaatgtattt agaaaaataa acaaataggg gttccgcgca catttccccg aaaagtgcca    12690
cctgacgtcc gggagatctc ccgatcccct atggtcgact ctcagtacaa tctgctctga    12750
tgccgcatag ttaagccagt atctgctccc tgcttgtgtg ttggaggtcg ctgagtagtg    12810
cgcgagcaaa atttaagcta caacaaggca aggcttgacc gacaattgca tgaagaatct    12870
gcttagggtt aggcgttttg cgctgcttcg cgatgtacgg gccagatata cgcgttgaca    12930
ttgattattg actagttatt aatagtaatc aattacgggg tcattagttc atagcccata    12990
tatggagttc cgcgttacat aacttacggt aaatggcccg cctggctgac cgcccaacga    13050
cccccgccca ttgacgtcaa taatgacgta tgttcccata gtaacgccaa tagggacttt    13110
ccattgacgt caatgggtgg actatttacg gtaaactgcc cacttggcag tacatcaagt    13170
gtatcatatg ccaagtacgc cccctattga cgtcaatgac ggtaaatggc cgcctggca     13230
ttatgcccag tacatgacct tatgggactt tcctacttgg cagtacatct acgtattagt    13290
catcgctatt accatggtga tgcggttttg gcagtacatc aatgggcgtg gatagcggtt    13350
tgactcacgg ggatttccaa gtctccaccc cattgacgtc aatgggagtt tgttttggca    13410
ccaaaatcaa cgggactttc caaaatgtcg taacaactcc gccccattga cgcaaatggg    13470
cggtaggcgt gtacggtggg aggtctatat aagcagagct ctctggctaa ctagagaacc    13530
cactgcttac tggcttatcg aaattaatac gactcactat agggagaccc aagctggcta    13590
gttaagcttg gtaccgagct cg                                              13612
```

<210> SEQ ID NO 17
<211> LENGTH: 427
<212> TYPE: PRT
<213> ORGANISM: Artificial Sequence
<220> FEATURE:
<223> OTHER INFORMATION: Plasmid pcDNA3.1 hp75 Nr.16

<400> SEQUENCE: 17

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn

```
            35                  40                  45
Leu Gly Glu Gly Val Ala Gln Pro Cys Gly Ala Asn Gln Thr Val Cys
 50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
                 85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
                115                 120                 125

Glu Ala Gly Ser Gly Leu Val Phe Ser Cys Gln Asp Lys Gln Asn Thr
                130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
                195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
                260                 265                 270

Lys Arg Trp Asn Ser Cys Lys Gln Asn Lys Gln Gly Ala Asn Ser Arg
                275                 280                 285

Pro Val Asn Gln Thr Pro Pro Glu Gly Glu Lys Leu His Ser Asp
                290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350

Gly Ser Ala Gly Asp Thr Trp Arg His Leu Ala Gly Glu Leu Gly Tyr
                355                 360                 365

Gln Pro Glu His Ile Asp Ser Phe Thr His Glu Ala Cys Pro Val Arg
                370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 18
<211> LENGTH: 8846
<212> TYPE: DNA
<213> ORGANISM: Artificial Sequence
```

```
<220> FEATURE:
<223> OTHER INFORMATION: Plasmid pIRES hNgR hp75
<220> FEATURE:
<221> NAME/KEY: CDS
<222> LOCATION: (1202)..(2620)
<223> OTHER INFORMATION: human NogoR sequence
<220> FEATURE:
<221> NAME/KEY: CDS
<222> LOCATION: (3294)..(4574)
<223> OTHER INFORMATION: human p75 sequence

<400> SEQUENCE: 18
gtgatgctcg tcagggggc ggagcctatg gaaaaacgcc agcaacgcgg ccttttttacg    60 gttcctggcc ttttgctggc cttttgctca catggctcga cagatcttca atattggcca   120
ttagccatat tattcattgg ttatatagca taaatcaata ttggctattg ccattgcat    180 acgttgtatc tatatcataa tatgtacatt tatattggct catgtccaat atgaccgcca   240
tgttggcatt gattattgac tagttattaa tagtaatcaa ttacggggtc attagttcat   300
agcccatata tggagttccg cgttacataa cttacggtaa atggcccgcc tggctgaccg   360
cccaacgacc cccgcccatt gacgtcaata atgacgtatg ttcccatagt aacgccaata   420
gggactttcc attgacgtca atgggtggag tatttacggt aaactgccca cttggcagta   480
catcaagtgt atcatatgcc aagtccgccc cctattgacg tcaatgacgg taaatggccc   540
gcctggcatt atgcccagta catgacctta cgggactttc ctacttggca gtacatctac   600
gtattagtca tcgctattac catggtgatg cggttttggc agtacaccaa tgggcgtgga   660
tagcggtttg actcacgggg atttccaagt ctccacccca ttgacgtcaa tgggagtttg   720
ttttggcacc aaaatcaacg ggactttcca aatgtcgta acaactgcga tcgcccgccc   780
cgttgacgca aatgggcggt aggcgtgtac ggtgggaggt ctatataagc agagctcgtt   840
tagtgaaccg tcagatcact agaagcttta ttgcggtagt ttatcacagt taaattgcta   900
acgcagtcag tgcttctgac acaacagtct cgaacttaag ctgcagtgac tctcttaagg   960
tagccttgca gaagttggtc gtgaggcact gggcaggtaa gtatcaaggt tacaagacag  1020
gtttaaggag accaatagaa actgggcttg tcgagacaga aagactctt gcgtttctga  1080 taggcaccta ttggtcttac tgacatccac tttgcctttc tctccacagg tgtccactcc  1140
cagttcaatt acagctctta aggctagagt acttaatacg actcactata ggctagagct  1200 t atg aag agg gcg tcc gct gga ggg agc cgg ctg ctg gca tgg gtg ctg  1249
  Met Lys Arg Ala Ser Ala Gly Gly Ser Arg Leu Leu Ala Trp Val Leu
  1               5                  10                  15 tgg ctg cag gcc tgg cag gtg gca gcc cca tgc cca ggt gcc tgc gta    1297
Trp Leu Gln Ala Trp Gln Val Ala Ala Pro Cys Pro Gly Ala Cys Val
            20                  25                  30 tgc tac aat gag ccc aag gtg acg aca agc tgc ccc cag cag ggc ctg    1345
Cys Tyr Asn Glu Pro Lys Val Thr Thr Ser Cys Pro Gln Gln Gly Leu
        35                  40                  45 cag gct gtg ccc gtg ggc atc cct gct gcc agc cag cgc atc ttc ctg    1393
Gln Ala Val Pro Val Gly Ile Pro Ala Ala Ser Gln Arg Ile Phe Leu
    50                  55                  60 cac ggc aac cgc atc tcg cat gtg cca gct gcc agc ttc cgt gcc tgc    1441
His Gly Asn Arg Ile Ser His Val Pro Ala Ala Ser Phe Arg Ala Cys
65                  70                  75                  80 cgc aac ctc acc atc ctg tgg ctg cac tcg aat gtg ctg gcc cga att    1489
Arg Asn Leu Thr Ile Leu Trp Leu His Ser Asn Val Leu Ala Arg Ile
                85                  90                  95 gat gcg gct gcc ttc act ggc ctg gcc ctc ctg gag cag ctg gac ctc    1537
Asp Ala Ala Ala Phe Thr Gly Leu Ala Leu Leu Glu Gln Leu Asp Leu
```

-continued

```
              100                 105                 110
agc gat aat gca cag ctc cgg tct gtg gac cct gcc aca ttc cac ggc      1585
Ser Asp Asn Ala Gln Leu Arg Ser Val Asp Pro Ala Thr Phe His Gly
        115                 120                 125 ctg ggc cgc cta cac acg ctg cac ctg gac cgc tgc ggc ctg cag gag      1633
Leu Gly Arg Leu His Thr Leu His Leu Asp Arg Cys Gly Leu Gln Glu
130                 135                 140 ctg ggc ccg ggg ctg ttc cgc ggc ctg gct gcc ctg cag tac ctc tac      1681
Leu Gly Pro Gly Leu Phe Arg Gly Leu Ala Ala Leu Gln Tyr Leu Tyr
145                 150                 155                 160 ctg cag gac aac gcg ctg cag gca ctg cct gat gac acc ttc cgc gac      1729
Leu Gln Asp Asn Ala Leu Gln Ala Leu Pro Asp Asp Thr Phe Arg Asp
        165                 170                 175 ctg ggc aac ctc aca cac ctc ttc ctg cac ggc aac cgc atc tcc agc      1777
Leu Gly Asn Leu Thr His Leu Phe Leu His Gly Asn Arg Ile Ser Ser
        180                 185                 190 gtg ccc gag cgc gcc ttc cgt ggg ctg cac agc ctc gac cgt ctc cta      1825
Val Pro Glu Arg Ala Phe Arg Gly Leu His Ser Leu Asp Arg Leu Leu
        195                 200                 205 ctg cac cag aac cgc gtg gcc cat gtg cac ccg cat gcc ttc gt gac      1873
Leu His Gln Asn Arg Val Ala His Val His Pro His Ala Phe Arg Asp
        210                 215                 220 ctt ggc cgc ctc atg aca ctc tat ctg ttt gcc aac aat cta tca gcg      1921
Leu Gly Arg Leu Met Thr Leu Tyr Leu Phe Ala Asn Asn Leu Ser Ala
225                 230                 235                 240 ctg ccc act gag gcc ctg gcc ccc ctg cgt gcc ctg cag tac ctg agg      1969
Leu Pro Thr Glu Ala Leu Ala Pro Leu Arg Ala Leu Gln Tyr Leu Arg
        245                 250                 255 ctc aac gac aac ccc tgg gtg tgt gac tgc cgg gca cgc cca ctc tgg      2017
Leu Asn Asp Asn Pro Trp Val Cys Asp Cys Arg Ala Arg Pro Leu Trp
        260                 265                 270 gcc tgg ctg cag aag ttc cgc ggc tcc tcc tcc gag gtg ccc tgc agc      2065
Ala Trp Leu Gln Lys Phe Arg Gly Ser Ser Ser Glu Val Pro Cys Ser
        275                 280                 285 ctc ccg caa cgc ctg gct ggc cgt gac ctc aaa cgc cta gct gcc aat      2113
Leu Pro Gln Arg Leu Ala Gly Arg Asp Leu Lys Arg Leu Ala Ala Asn
        290                 295                 300 gac ctg cag ggc tgc gct gtg gcc acc ggc cct tac cat ccc atc tgg      2161
Asp Leu Gln Gly Cys Ala Val Ala Thr Gly Pro Tyr His Pro Ile Trp
305                 310                 315                 320 acc ggc agg gcc acc gat gag gag ccg ctg ggg ctt ccc aag tgc tgc      2209
Thr Gly Arg Ala Thr Asp Glu Glu Pro Leu Gly Leu Pro Lys Cys Cys
                325                 330                 335 cag cca gat gcc gct gac aag gcc tca gta ctg gag cct gga aga cca      2257
Gln Pro Asp Ala Ala Asp Lys Ala Ser Val Leu Glu Pro Gly Arg Pro
        340                 345                 350 gct tcg gca ggc aat gcg ctg aag gga cgc gtg ccg ccc ggt gac agc      2305
Ala Ser Ala Gly Asn Ala Leu Lys Gly Arg Val Pro Pro Gly Asp Ser
        355                 360                 365 ccg ccg ggc aac ggc tct ggc cca cgg cac atc aat gac tca ccc ttt      2353
Pro Pro Gly Asn Gly Ser Gly Pro Arg His Ile Asn Asp Ser Pro Phe
        370                 375                 380 ggg act ctg cct ggc tct gct gag ccc ccg ctc act gca gtg cgg ccc      2401
Gly Thr Leu Pro Gly Ser Ala Glu Pro Pro Leu Thr Ala Val Arg Pro
385                 390                 395                 400 gag ggc tcc gag cca cca ggg ttc ccc acc tcg ggc cct cgc cgg agg      2449
Glu Gly Ser Glu Pro Pro Gly Phe Pro Thr Ser Gly Pro Arg Arg Arg
                405                 410                 415 cca ggc tgt tca cgc aag aac cgc acc cgc agc cac tgc cgt ctg ggc      2497
```

```
                Pro Gly Cys Ser Arg Lys Asn Arg Thr Arg Ser His Cys Arg Leu Gly
                                420                 425                 430 cag gca ggc agc ggg ggt ggc ggg act ggt gac tca gaa ggc tca ggt         2545
Gln Ala Gly Ser Gly Gly Gly Gly Thr Gly Asp Ser Glu Gly Ser Gly
            435                 440                 445 gcc cta ccc agc ctc acc tgc agc ctc acc ccc ctg ggc ctg gcg ctg         2593
Ala Leu Pro Ser Leu Thr Cys Ser Leu Thr Pro Leu Gly Leu Ala Leu
        450                 455                 460 gtg ctg tgg aca gtg ctt ggg ccc tgc tgagaattca cgcgtcgagc               2640
Val Leu Trp Thr Val Leu Gly Pro Cys
465                 470 atgcatctag gcggccaat tccgccctc tccctcccc ccccctaacg ttactggccg          2700
aagccgcttg aataaggcc ggtgtgcgtt tgtctatatg tgattttcca ccatattgcc        2760
gtcttttggc aatgtgaggg cccggaaacc tggccctgtc ttcttgacga gcattcctag       2820
gggtctttcc cctctcgcca aggaatgca aggtctgttg aatgtcgtga aggaagcagt        2880
tcctctggaa gcttcttgaa gacaaacaac gtctgtagcg acctttgca ggcagcggaa       2940 ccccccacct ggcgacaggt gcctctgcgg ccaaaagcca cgtgtataag atacacctgc      3000
aaaggcggca caaccccagt gccacgttgt gagttggata gttgtggaaa gagtcaaatg       3060
gctctcctca agcgtattca caaggggct gaaggatgcc cagaaggtac cccattgtat        3120
gggatctgat ctggggcctc ggtgcacatg ctttacatgt gtttagtcga ggttaaaaaa       3180
acgtctaggc ccccgaacc acgggacgt ggttttcctt tgaaaacac gatgataagc         3240 ttgccacaac ccgggatcct ctagtccagt gtggtggaat gcccttgcc acc atg          3296
                                                              Met ggg gca ggt gcc acc ggc cgc gcc atg gac ggg ccg cgc ctg ctg ctg         3344
Gly Ala Gly Ala Thr Gly Arg Ala Met Asp Gly Pro Arg Leu Leu Leu
475                 480                 485                 490 ttg ctg ctt ctg ggg gtg tcc ctt gga ggt gcc aag gag gca tgc ccc         3392
Leu Leu Leu Leu Gly Val Ser Leu Gly Gly Ala Lys Glu Ala Cys Pro
                495                 500                 505 aca ggc ctg tac acg cac agc ggt gag tgc tgc aaa gcc tgc aac ctg         3440
Thr Gly Leu Tyr Thr His Ser Gly Glu Cys Cys Lys Ala Cys Asn Leu
            510                 515                 520 ggc gag ggt gtg gcc cag cct tgt gga gcc aac cag acc gtg tgt gag         3488
Gly Glu Gly Val Ala Gln Pro Cys Gly Ala Asn Gln Thr Val Cys Glu
        525                 530                 535 ccc tgc ctg gac agc gtg acg ttc tcc gac gtg gtg agc gcg acc gag         3536
Pro Cys Leu Asp Ser Val Thr Phe Ser Asp Val Val Ser Ala Thr Glu
        540                 545                 550 ccg tgc aag ccg tgc acc gag tgc gtg ggg ctc cag agc atg tcg gcg         3584
Pro Cys Lys Pro Cys Thr Glu Cys Val Gly Leu Gln Ser Met Ser Ala
555                 560                 565                 570 ccg tgc gtg gag gcc gac gac gcc gtg tgc cgc tgc gcc tac ggc tac         3632
Pro Cys Val Glu Ala Asp Asp Ala Val Cys Arg Cys Ala Tyr Gly Tyr
                575                 580                 585 tac cag gat gag acg act ggg cgc tgc gag gcg tgc cgc gtg tgc gag         3680
Tyr Gln Asp Glu Thr Thr Gly Arg Cys Glu Ala Cys Arg Val Cys Glu
            590                 595                 600 gcg ggc tcg ggc ctc gtg ttc tcc tgc cag gac aag cag aac acc gtg         3728
Ala Gly Ser Gly Leu Val Phe Ser Cys Gln Asp Lys Gln Asn Thr Val
        605                 610                 615 tgc gag gag tgc ccc gac ggc acg tat tcc gac gag gcc aac cac gtg         3776
Cys Glu Glu Cys Pro Asp Gly Thr Tyr Ser Asp Glu Ala Asn His Val
        620                 625                 630 gac ccg tgc ctg ccc tgc acc gtg tgc gag gac acc gag cgc cag ctc         3824
```

```
                Asp Pro Cys Leu Pro Cys Thr Val Cys Glu Asp Thr Glu Arg Gln Leu
                635                 640                 645                 650 cgc gag tgc aca cgc tgg gcc gac gcc gag tgc gag gag atc cct ggc                 3872
Arg Glu Cys Thr Arg Trp Ala Asp Ala Glu Cys Glu Glu Ile Pro Gly
                655                 660                 665 cgt tgg att aca cgg tcc aca ccc cca gag ggc tcg gac agc aca gcc                 3920
Arg Trp Ile Thr Arg Ser Thr Pro Pro Glu Gly Ser Asp Ser Thr Ala
            670                 675                 680 ccc agc acc cag gag cct gag gca cct cca gaa caa gac ctc ata gcc                 3968
Pro Ser Thr Gln Glu Pro Glu Ala Pro Pro Glu Gln Asp Leu Ile Ala
        685                 690                 695 agc acg gtg gca ggt gtg gtg acc aca gtg atg ggc agc tcc cag ccc                 4016
Ser Thr Val Ala Gly Val Val Thr Thr Val Met Gly Ser Ser Gln Pro
    700                 705                 710 gtg gtg acc cga ggc acc acc gac aac ctc atc cct gtc tat tgc tcc                 4064
Val Val Thr Arg Gly Thr Thr Asp Asn Leu Ile Pro Val Tyr Cys Ser
715                 720                 725                 730 atc ctg gct gct gtg gtt gtg ggt ctt gtg gcc tac ata gcc ttc aag                 4112
Ile Leu Ala Ala Val Val Val Gly Leu Val Ala Tyr Ile Ala Phe Lys
                735                 740                 745 agg tgg aac agc tgc aag cag aac aag caa gga gcc aac agc cgg cca                 4160
Arg Trp Asn Ser Cys Lys Gln Asn Lys Gln Gly Ala Asn Ser Arg Pro
            750                 755                 760 gtg aac cag acg ccc cca cca gag gga gaa aaa ctc cac agc gac agt                 4208
Val Asn Gln Thr Pro Pro Pro Glu Gly Glu Lys Leu His Ser Asp Ser
        765                 770                 775 ggc atc tcc gtg gac agc cag agc ctg cat gac cag cag ccc cac acg                 4256
Gly Ile Ser Val Asp Ser Gln Ser Leu His Asp Gln Gln Pro His Thr
    780                 785                 790 cag aca gcc tcg ggc cag gcc ctc aag ggt gac gga ggc ctc tac agc                 4304
Gln Thr Ala Ser Gly Gln Ala Leu Lys Gly Asp Gly Gly Leu Tyr Ser
795                 800                 805                 810 agc ctg ccc cca gcc aag cgg gag gag gtg gag aag ctt ctc aac ggc                 4352
Ser Leu Pro Pro Ala Lys Arg Glu Glu Val Glu Lys Leu Leu Asn Gly
                815                 820                 825 tct gcg ggg gac acc tgg cgg cac ctg gcg ggc gag ctg ggc tac cag                 4400
Ser Ala Gly Asp Thr Trp Arg His Leu Ala Gly Glu Leu Gly Tyr Gln
            830                 835                 840 ccc gag cac ata gac tcc ttt acc cat gag gcc tgc ccc gtt cgc gcc                 4448
Pro Glu His Ile Asp Ser Phe Thr His Glu Ala Cys Pro Val Arg Ala
        845                 850                 855 ctg ctt gca agc tgg gcc acc cag gac agc gcc aca ctg gac gcc ctc                 4496
Leu Leu Ala Ser Trp Ala Thr Gln Asp Ser Ala Thr Leu Asp Ala Leu
    860                 865                 870 ctg gcc gcc ctg cgc cgc atc cag cga gcc gac ctc gtg gag agt ctg                 4544
Leu Ala Ala Leu Arg Arg Ile Gln Arg Ala Asp Leu Val Glu Ser Leu
875                 880                 885                 890 tgc agt gag tcc act gcc aca tcc cca gtg tgaaagggca attctgcaga                   4594
Cys Ser Glu Ser Thr Ala Thr Ser Pro Val
                895                 900 tatccagcac agtggcggcc gcttcccttt agtgagggtt aatgcttcga gcagacatga              4654
taagatacat tgatgagttt ggacaaacca caactagaat gcagtgaaaa aaatgcttta              4714
tttgtgaaat ttgtgatgct attgctttat ttgtaaccat tataagctgc aataaacaag              4774
ttaacaacaa caattgcatt catttatgt ttcaggttca gggggagatg tgggaggttt               4834
tttaaagcaa gtaaacctc tacaaatgtg gtaaatccg ataaggatcg atccgggctg                4894
gcgtaatagc gaagaggccc gcaccgatcg cccttcccaa cagttgcgca gcctgaatgg              4954
```

```
cgaatggacg cgccctgtag cggcgcatta agcgcggcgg gtgtggtggt tacgcgcagc   5014
gtgaccgcta cacttgccag cgccctagcg cccgctcctt tcgctttctt cccttccttt   5074
ctcgccacgt tcgccggctt tccccgtcaa gctctaaatc gggggctccc tttagggttc   5134
cgatttagag ctttacggca cctcgaccgc aaaaaacttg atttgggtga tggttcacgt   5194
agtgggccat cgccctgata gacggttttt cgcccttgca cgttggagtc cacgttcttt   5254
aatagtggac tcttgttcca aactggaaca acactcaacc ctatctcggt ctattctttt   5314
gatttataag ggattttgcc gatttcggcc tattggttaa aaaatgagct gatttaacaa   5374
atatttaacg cgaattttaa caaaatatta cgtttacaa tttcgcctga tgcgtatttt    5434
tctccttacg catctgtgcg gtatttcaca ccgcatacgc ggatctgcgc agcaccatgg   5494
cctgaaataa cctctgaaag aggaacttgg ttaggtacct tctgaggcgg aaagaaccag   5554
ctgtggaatg tgtgtcagtt agggtgtgga aagtccccag gctcccagc aggcagaagt    5614
atgcaaagca tgcatctcaa ttagtcagca accaggtgtg gaaagtcccc aggctcccca   5674
gcaggcagaa gtatgcaaag catgcatctc aattagtcag caaccatagt cccgccccta   5734
actccgccca tcccgcccct aactccgccc agttccgccc attctccgcc ccatggctga   5794
ctaatttttt ttatttatgc agaggccgag gccgcctcgg cctctgagct attccagaag   5854
tagtgaggag ctttttttgg aggcctaggc ttttgcaaaa agcttgattc ttctgacaca   5914
acagtctcga acttaaggct agagccacca tgattgaaca agatggattg cacgcaggtt   5974
ctccggccgc ttgggtggag aggctattcg gctatgactg ggcacaacag acaatcggct   6034
gctctgatgc cgccgtgttc cggctgtcag cgcaggggcg cccggttctt tttgtcaaga   6094
ccgacctgtc cggtgccctg aatgaactgc aggacgaggc agcgcggcta tcgtggctgg   6154
ccacgacggg cgttccttgc gcagctgtgc tcgacgttgt cactgaagcg ggaagggact   6214
ggctgctatt gggcgaagtg ccggggcagg atctcctgtc atctcacctt gctcctgccg   6274
agaaagtatc catcatggct gatgcaatgc ggcggctgca tacgcttgat ccggctacct   6334
gcccattcga ccaccaagcg aaacatcgca tcgagcgagc acgtactcgg atggaagccg   6394
gtcttgtcga tcaggatgat ctggacgaag agcatcaggg gctcgcgcca gccgaactgt   6454
tcgccaggct caaggcgcgc atgcccgacg gcgaggatct cgtcgtgacc catggcgatg   6514
cctgcttgcc gaatatcatg gtggaaaatg gccgcttttc tggattcatc gactgtggcc   6574
ggctgggtgt ggcggaccgc tatcaggaca tagcgttggc tacccgtgat attgctgaag   6634
agcttggcgg cgaatgggct gaccgcttcc tcgtgcttta cggtatcgcc gctcccgatt   6694
cgcagcgcat cgccttctat cgccttcttg acgagttctt ctgagcggga ctctgggtt    6754
cgaaatgacc gaccaagcga cgcccaacct gccatcacga tggccgcaat aaaatatctt   6814
tattttcatt acatctgtgt gttggttttt tgtgtgaatc gatagcgata aggatccgcg   6874
tatggtgcac tctcagtaca atctgctctg atgccgcata gttaagccag ccccgacacc   6934
cgccaacacc cgctgacgcg ccctgacggg cttgtctgct cccggcatcc gcttacagac   6994
aagctgtgac cgtctccggg agctgcatgt gtcagaggtt ttcaccgtca tcaccgaaac   7054
gcgcgagacg aaagggcctc gtgatacgcc tatttttata ggttaatgtc atgataataa   7114
tggtttctta gacgtcaggt ggcacttttc ggggaaatgt gcgcggaacc cctatttgtt   7174
tatttttcta aatacattca aatatgtatc cgctcatgag acaataaccc tgataaatgc   7234
ttcaataata ttgaaaaagg aagagtatga gtattcaaca tttccgtgtc gcccttattc   7294
cctttttgc ggcattttgc cttcctgttt ttgctcaccc agaaacgctg gtgaaagtaa    7354
```

```
aagatgctga agatcagttg ggtgcacgag tgggttacat cgaactggat ctcaacagcg    7414
gtaagatcct tgagagtttt cgccccgaag aacgttttcc aatgatgagc acttttaaag    7474
ttctgctatg tggcgcggta ttatcccgta ttgacgccgg gcaagagcaa ctcggtcgcc    7534
gcatacacta ttctcagaat gacttggttg agtactcacc agtcacagaa aagcatctta    7594
cggatggcat gacagtaaga gaattatgca gtgctgccat aaccatgagt gataacactg    7654
cggccaactt acttctgaca acgatcggag gaccgaagga gctaaccgct tttttgcaca    7714
acatggggga tcatgtaact cgccttgatc gttgggaacc ggagctgaat gaagccatac    7774
caaacgacga gcgtgacacc acgatgcctg tagcaatggc aacaacgttg cgcaaactat    7834
taactggcga actacttact ctagcttccc ggcaacaatt aatagactgg atggaggcgg    7894
ataaagttgc aggaccactt ctgcgctcgg cccttccggc tggctggttt attgctgata    7954
aatctggagc cggtgagcgt gggtctcgcg gtatcattgc agcactgggg ccagatggta    8014
agccctcccg tatcgtagtt atctacacga cggggagtca ggcaactatg gatgaacgaa    8074
atagacagat cgctgagata ggtgcctcac tgattaagca ttggtaactg tcagaccaag    8134
tttactcata tactttag attgatttaa aacttcattt ttaatttaaa aggatctagg       8194
tgaagatcct ttttgataat ctcatgacca aaatcccttta acgtgagttt tcgttccact    8254
gagcgtcaga ccccgtagaa aagatcaaag gatcttcttg agatcctttt tttctgcgcg    8314
taatctgctg cttgcaaaca aaaaaaccac cgctaccagc ggtggtttgt ttgccggatc    8374
aagagctacc aactctttt ccgaaggtaa ctggcttcag cagagcgcag ataccaaata     8434
ctgtccttct agtgtagccg tagttaggcc accacttcaa gaactctgta gcaccgccta    8494
catacctcgc tctgctaatc ctgttaccag tggctgctgc cagtggcgat aagtcgtgtc    8554
ttaccgggtt ggactcaaga cgatagttac cggataaggc gcagcggtcg ggctgaacgg    8614
ggggttcgtg cacacagccc agcttggagc gaacgaccta caccgaactg agatacctac    8674
agcgtgagct atgagaaagc gccacgcttc ccgaagggag aaaggcggac aggtatccgg    8734
taagcggcag ggtcggaaca ggagagcgca cgagggagct tccaggggga aacgcctggt    8794
atctttatag tcctgtcggg tttcgccacc tctgacttga gcgtcgattt tt             8846
```

<210> SEQ ID NO 19
<211> LENGTH: 473
<212> TYPE: PRT
<213> ORGANISM: Artificial Sequence
<220> FEATURE:
<223> OTHER INFORMATION: Plasmid pIRES hNgR hp75

<400> SEQUENCE: 19

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

```
Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 20
<211> LENGTH: 427
<212> TYPE: PRT
<213> ORGANISM: Artificial Sequence
<220> FEATURE:
<223> OTHER INFORMATION: Plasmid pIRES hNgR hp75
```

<400> SEQUENCE: 20

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Ala Lys Glu Ala Cys
            20                  25                  30

Pro Thr Gly Leu Tyr Thr His Ser Gly Glu Cys Cys Lys Ala Cys
            35                  40                  45

Leu Gly Glu Gly Val Ala Gln Pro Cys Gly Ala Asn Gln Thr Val Cys
50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
            275                 280                 285

Pro Val Asn Gln Thr Pro Pro Glu Gly Glu Lys Leu His Ser Asp
            290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
            370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
```

405                 410                 415
Leu Cys Ser Glu Ser Thr Ala Thr Ser Pro Val
                420                 425

<210> SEQ ID NO 21
<211> LENGTH: 6482
<212> TYPE: DNA
<213> ORGANISM: Artificial Sequence
<220> FEATURE:
<223> OTHER INFORMATION: plasmid pcDNA4(mycHis)A hRhoA wt
<220> FEATURE:
<221> NAME/KEY: CDS
<222> LOCATION: (1058)..(1636)
<223> OTHER INFORMATION: human RhoA sequence

<400> SEQUENCE: 21

| | |
|---|---:|
| gatctcccga tccctatgg tcgactctca gtacaatctg ctctgatgcc gcatagttaa | 60 |
| gccagtatct gctccctgct tgtgtgttgg aggtcgctga gtagtgcgcg agcaaaattt | 120 |
| aagctacaac aaggcaaggc ttgaccgaca attgcatgaa gaatctgctt agggttaggc | 180 |
| gttttgcgct gcttcgcgat gtacgggcca gatatacgcg ttgacattga ttattgacta | 240 |
| gttattaata gtaatcaatt acggggtcat tagttcatag cccatatatg gagttccgcg | 300 |
| ttacataact tacggtaaat ggcccgcctg gctgaccgcc caacgacccc cgcccattga | 360 |
| cgtcaataat gacgtatgtt cccatagtaa cgccaatagg gactttccat tgacgtcaat | 420 |
| gggtggacta tttacggtaa actgcccact tggcagtaca tcaagtgtat catatgccaa | 480 |
| gtacgccccc tattgacgtc aatgacggta aatggcccgc ctggcattat gcccagtaca | 540 |
| tgaccttatg ggactttcct acttggcagt acatctacgt attagtcatc gctattacca | 600 |
| tggtgatgcg gttttggcag tacatcaatg ggcgtggata gcggtttgac tcacggggat | 660 |
| ttccaagtct ccaccccatt gacgtcaatg ggagtttgtt ttggcaccaa aatcaacggg | 720 |
| actttccaaa atgtcgtaac aactccgccc cattgacgca aatgggcggt aggcgtgtac | 780 |
| ggtgggaggt ctatataagc agagctctct ggctaactag agaacccact gcttactggc | 840 |
| ttatcgaaat taatacgact cactataggg agacccaagc tggctagtta agcttggtac | 900 |
| cgagctcgga tccactagtc cagtgtggtg gaattcggca cgaggctcgt tagtccacgg | 960 |
| tctggtcttc agctacccgc cttcgtctcc gagtttgcga ctcgcggacc ggcgtccccg | 1020 |
| gcgcgaagag gctggactcg gattcgttgc ctgagca atg gct gcc atc cgg aag | 1075 |

Met Ala Ala Ile Arg Lys
                                  1               5

| | |
|---|---:|
| aaa ctg gtg att gtt ggt gat gga gcc tgt gga aag aca tgc ttg ctc | 1123 |
Lys Leu Val Ile Val Gly Asp Gly Ala Cys Gly Lys Thr Cys Leu Leu
         10                  15                  20

| | |
|---|---:|
| ata gtc ttc agc aag gac cag ttc cca gag gtg tat gtg ccc aca gtg | 1171 |
Ile Val Phe Ser Lys Asp Gln Phe Pro Glu Val Tyr Val Pro Thr Val
     25                  30                  35

| | |
|---|---:|
| ttt gag aac tat gtg gca gat atc gag gtg gat gga aag cag gta gag | 1219 |
Phe Glu Asn Tyr Val Ala Asp Ile Glu Val Asp Gly Lys Gln Val Glu
 40                  45                  50

| | |
|---|---:|
| ttg gct ttg tgg gac aca gct ggg cag gaa gat tat gat cgc ctg agg | 1267 |
Leu Ala Leu Trp Asp Thr Ala Gly Gln Glu Asp Tyr Asp Arg Leu Arg
55                  60                  65                  70

| | |
|---|---:|
| ccc ctc tcc tac cca gat acc gat gtt ata ctg atg tgt ttt tcc atc | 1315 |
Pro Leu Ser Tyr Pro Asp Thr Asp Val Ile Leu Met Cys Phe Ser Ile
                 75                  80                  85

| | |
|---|---:|
| gac agc cct gat agt tta gaa aac atc cca gaa aag tgg acc cca gaa | 1363 |
Asp Ser Pro Asp Ser Leu Glu Asn Ile Pro Glu Lys Trp Thr Pro Glu

|  |  |
|---|---:|
| gtc aag cat ttc tgt ccc aac gtg ccc atc atc ctg gtt ggg aat aag<br>Val Lys His Phe Cys Pro Asn Val Pro Ile Ile Leu Val Gly Asn Lys<br>     105                       110                     115 | 1411 |
| aag gat ctt cgg aat gat gag cac aca agg cgg gag cta gcc aag atg<br>Lys Asp Leu Arg Asn Asp Glu His Thr Arg Arg Glu Leu Ala Lys Met<br>120                       125                     130 | 1459 |
| aag cag gag ccg gtg aaa cct gaa gaa ggc aga gat atg gca aac agg<br>Lys Gln Glu Pro Val Lys Pro Glu Glu Gly Arg Asp Met Ala Asn Arg<br>135                     140                     145                     150 | 1507 |
| att ggc gct ttt ggg tac atg gag tgt tca gca aag acc aaa gat gga<br>Ile Gly Ala Phe Gly Tyr Met Glu Cys Ser Ala Lys Thr Lys Asp Gly<br>                155                     160                     165 | 1555 |
| gtg aga gag gtt ttt gaa atg gct acg aga gct gct ctg caa gct aga<br>Val Arg Glu Val Phe Glu Met Ala Thr Arg Ala Ala Leu Gln Ala Arg<br>     170                       175                     180 | 1603 |
| cgt ggg aag aaa aaa tct ggg tgc ctt gtc ttg tgaaaccttg ctgcaagcac<br>Arg Gly Lys Lys Lys Ser Gly Cys Leu Val Leu<br>         185                     190 | 1656 |
| agcccttatg cggttaattt tgaagtgctg tttattaatc ttagtgtatg attactggcc | 1716 |
| tttttcattt atctataatt tacctaagat tacaaatcag aagtcatctt gctaccagta | 1776 |
| tttagaagcc aactatgatt attaacgatg tccaacccgt ctggcccacc agggtccttt | 1836 |
| tgacactgct ctaacagccc tcctctgcac tcccacctga cacaccaggc gctaattcaa | 1896 |
| ggaatttctt aacttcttgc ttctttctag aaagagaaac agttggtaac ttttgtgaat | 1956 |
| taggctgtaa ctactttata actaacatgt cctgcctatt atctgtcagc tgcaaggtac | 2016 |
| tctggtgagt caccacttca gggctttact ccgtaacaga ttttgttggc atagctctgg | 2076 |
| ggtgggcagt ttttgaaaa tgggctcaac cagaaaagcc caagttcatg cagctgtggc | 2136 |
| agagttacag ttctgtggtt tcatgttagt taccttatag ttactgtgta attagtgcca | 2196 |
| cttaatgtat gttaccaaaa ataaatatat ctaccccaga ctagatgtag tattttttgt | 2256 |
| ataattggat ttcctaatac tgtcatcctc aaagaaagtg tattggtttt taaaaaaga | 2316 |
| aagtgtattt ggaaataaag tcagatggaa aattcaaaaa aaaaaaaaaa aaaactcgag | 2376 |
| tctagagggc ccttcgaaca aaaactcatc tcagaagagg atctgaatat gcataccggt | 2436 |
| catcatcacc atcaccattg agtttaaacc cgctgatcag cctcgactgt gccttctagt | 2496 |
| tgccagccat ctgttgtttg cccctccccc gtgccttcct tgaccctgga aggtgccact | 2556 |
| cccactgtcc tttcctaata aaatgaggaa attgcatcgc attgtctgag taggtgtcat | 2616 |
| tctattctgg ggggtggggt ggggcaggac agcaagggg aggattggga agacaatagc | 2676 |
| aggcatgctg gggatgcggt gggctctatg gcttctgagg cggaaagaac cagctggggc | 2736 |
| tctaggggt atccccacgc gccctgtagc ggcgcattaa gcgcggcggg tgtggtggtt | 2796 |
| acgcgcagcg tgaccgctac acttgccagc gccctagcgc ccgctccttt cgctttcttc | 2856 |
| ccttcctttc tcgccacgtt cgccggcttt ccccgtcaag ctctaaatcg ggcatccct | 2916 |
| ttagggttcc gatttagtgc tttacggcac ctcgacccca aaaaacttga ttagggtgat | 2976 |
| ggttcacgta gtgggccatc gccctgatag acgttttttc gccctttgac gttggagtcc | 3036 |
| acgttcttta atagtggact cttgttccaa actggaacaa cactcaaccc tatctcggtc | 3096 |
| tattcttttg atttataagg gattttgggg atttcggcct attggttaaa aaatgagctg | 3156 |
| atttaacaaa aatttaacgc gaattaattc tgtggaatgt gtgtcagtta gggtgtggaa | 3216 |
| agtccccagg ctccccaggc aggcagaagt atgcaaagca tgcatctcaa ttagtcagca | 3276 |

-continued

```
accaggtgtg gaaagtcccc aggctcccca gcaggcagaa gtatgcaaag catgcatctc   3336
aattagtcag caaccatagt cccgcccta  actccgccca tcccgcccct aactccgccc   3396
agttccgccc attctccgcc ccatggctga ctaattttt  ttatttatgc agaggccgag   3456
gccgcctctg cctctgagct attccagaag tagtgaggag gcttttttgg aggcctaggc   3516
ttttgcaaaa agctcccggg agcttgtata tccattttcg gatctgatca gcacgtgttg   3576
acaattaatc atcggcatag tatatcggca tagtataata cgacaaggtg aggaactaaa   3636
ccatggccaa gttgaccagt gccgttccgg tgctcaccgc gcgcgacgtc gccggagcgg   3696
tcgagttctg gaccgaccgg ctcgggttct cccgggactt cgtggaggac gacttcgccg   3756
gtgtggtccg ggacgacgtg accctgttca tcagcgcggt ccaggaccag gtggtgccgg   3816
acaacaccct ggcctgggtg tgggtgcgcg gcctggacga gctgtacgcc gagtggtcgg   3876
aggtcgtgtc cacgaacttc cgggacgcct ccggccggc  catgaccgag atcggcgagc   3936
agccgtgggg gcgggagttc gccctgcgcg accggccgg  caactgcgtg cacttcgtgg   3996
ccgaggagca ggactgacac gtgctacgag atttcgattc caccgccgcc ttctatgaaa   4056
ggttgggctt cggaatcgtt ttccgggacg ccggctggat gatcctccag cgcgggatc    4116
tcatgctgga gttcttcgcc cacccaact  tgtttattgc agcttataat ggttacaaat   4176
aaagcaatag catcacaaat ttcacaaata aagcatttt  ttcactgcat tctagttgtg   4236
gtttgtccaa actcatcaat gtatcttatc atgtctgtat accgtcgacc tctagctaga   4296
gcttggcgta atcatggtca tagctgtttc ctgtgtgaaa ttgttatccg ctcacaattc   4356
cacacaacat acgagccgga agcataaagt gtaaagcctg gggtgcctaa tgagtgagct   4416
aactcacatt aattgcgttg cgctcactgc ccgctttcca gtcgggaaac ctgtcgtgcc   4476
agctgcatta atgaatcggc caacgcgcgg ggagaggcgg tttgcgtatt gggcgctctt   4536
ccgcttcctc gctcactgac tcgctgcgct cggtcgttcg ctgcggcga  gcggtatcag   4596
ctcactcaaa ggcggtaata cggttatcca cagaatcagg ggataacgca ggaaagaaca   4656
tgtgagcaaa aggccagcaa aaggccagga accgtaaaaa ggccgcgttg ctggcgtttt   4716
tccataggct ccgcccccct gacgagcatc acaaaaatcg acgctcaagt cagaggtggc   4776
gaaacccgac aggactataa agataccagg cgtttccccc tggaagctcc ctcgtgcgct   4836
ctcctgttcc gaccctgccg cttaccggat acctgtccgc ctttctccct tcgggaagcg   4896
tggcgctttc tcaatgctca cgctgtaggt atctcagttc ggtgtaggtc gttcgctcca   4956
agctgggctg tgtgcacgaa ccccccgttc agcccgaccg ctgcgcctta tccggtaact   5016
atcgtcttga gtccaacccg gtaagacacg acttatcgcc actggcagca gccactggta   5076
acaggattag cagagcgagg tatgtaggcg gtgctacaga gttcttgaag tggtggccta   5136
actacggcta cactagaagg acagtatttg gtatctgcgc tctgctgaag ccagttacct   5196
tcggaaaaag agttggtagc tcttgatccg gcaaacaaac caccgctggt agcggtggtt   5256
tttttgtttg caagcagcag attacgcgca gaaaaaaagg atctcaagaa gatcctttga   5316
tcttttctac ggggtctgac gctcagtgga acgaaaactc acgttaaggg attttggtca   5376
tgagattatc aaaaaggatc ttcacctaga tccttttaaa ttaaaaatga agttttaaat   5436
caatctaaag tatatatgag taaacttggt ctgacagtta ccaatgctta atcagtgagg   5496
cacctatctc agcgatctgt ctatttcgtt catccatagt tgcctgactc cccgtcgtgt   5556
agataactac gatacgggag ggcttaccat ctggccccag tgctgcaatg ataccgcgag   5616
```

| | | |
|---|---|---|
| acccacgctc accggctcca gatttatcag caataaacca gccagccgga agggccgagc | 5676 | |
| gcagaagtgg tcctgcaact ttatccgcct ccatccagtc tattaattgt tgccgggaag | 5736 | |
| ctagagtaag tagttcgcca gttaatagtt tgcgcaacgt tgttgccatt gctacaggca | 5796 | |
| tcgtggtgtc acgctcgtcg tttggtatgg cttcattcag ctccggttcc caacgatcaa | 5856 | |
| ggcgagttac atgatccccc atgttgtgca aaaaagcggt tagctccttc ggtcctccga | 5916 | |
| tcgttgtcag aagtaagttg gccgcagtgt tatcactcat ggttatggca gcactgcata | 5976 | |
| attctcttac tgtcatgcca tccgtaagat gcttttctgt gactggtgag tactcaacca | 6036 | |
| agtcattctg agaatagtgt atgcggcgac cgagttgctc ttgcccggcg tcaatacggg | 6096 | |
| ataataccgc gccacatagc agaactttaa aagtgctcat cattggaaaa cgttcttcgg | 6156 | |
| ggcgaaaact ctcaaggatc ttaccgctgt tgagatccag ttcgatgtaa cccactcgtg | 6216 | |
| cacccaactg atcttcagca tcttttactt tcaccagcgt ttctgggtga gcaaaaacag | 6276 | |
| gaaggcaaaa tgccgcaaaa aagggaataa gggcgacacg gaaatgttga atactcatac | 6336 | |
| tcttcctttt tcaatattat tgaagcattt atcagggtta ttgtctcatg agcggataca | 6396 | |
| tatttgaatg tatttagaaa aataaacaaa taggggttcc gcgcacattt ccccgaaaag | 6456 | |
| tgccacctga cgtcgacgga tcggga | 6482 | |

<210> SEQ ID NO 22
<211> LENGTH: 193
<212> TYPE: PRT
<213> ORGANISM: Artificial Sequence
<220> FEATURE:
<223> OTHER INFORMATION: plasmid pcDNA4(mycHis)A hRhoA wt

<400> SEQUENCE: 22

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Val
            180                 185                 190

Leu
```

<210> SEQ ID NO 23
<211> LENGTH: 6853
<212> TYPE: DNA
<213> ORGANISM: Artificial Sequence
<220> FEATURE:
<223> OTHER INFORMATION: Plasmid pcDNA3 hRhoA wt
<220> FEATURE:
<221> NAME/KEY: CDS
<222> LOCATION: (127)..(705)
<223> OTHER INFORMATION: human RhoA sequence

<400> SEQUENCE: 23

```
aattcggcac gaggctcgtt agtccacggt ctggtcttca gctacccgcc ttcgtctccg      60
agtttgcgac tcgcggaccg gcgtccccgg cgcgaagagg ctggactcgg attcgttgcc     120 tgagca atg gct gcc atc cgg aag aaa ctg gtg att gtt ggt gat gga        168
       Met Ala Ala Ile Arg Lys Lys Leu Val Ile Val Gly Asp Gly
       1               5                   10 gcc tgt gga aag aca tgc ttg ctc ata gtc ttc agc aag gac cag ttc       216
Ala Cys Gly Lys Thr Cys Leu Leu Ile Val Phe Ser Lys Asp Gln Phe
15                  20                  25                  30 cca gag gtg tat gtg ccc aca gtg ttt gag aac tat gtg gca gat atc       264
Pro Glu Val Tyr Val Pro Thr Val Phe Glu Asn Tyr Val Ala Asp Ile
                35                  40                  45 gag gtg gat gga aag cag gta gag ttg gct ttg tgg gac aca gct ggg       312
Glu Val Asp Gly Lys Gln Val Glu Leu Ala Leu Trp Asp Thr Ala Gly
        50                  55                  60 cag gaa gat tat gat cgc ctg agg ccc ctc tcc tac cca gat acc gat       360
Gln Glu Asp Tyr Asp Arg Leu Arg Pro Leu Ser Tyr Pro Asp Thr Asp
65                  70                  75 gtt ata ctg atg tgt ttt tcc atc gac agc cct gat agt tta gaa aac       408
Val Ile Leu Met Cys Phe Ser Ile Asp Ser Pro Asp Ser Leu Glu Asn
            80                  85                  90 atc cca gaa aag tgg acc cca gaa gtc aag cat ttc tgt ccc aac gtg       456
Ile Pro Glu Lys Trp Thr Pro Glu Val Lys His Phe Cys Pro Asn Val
95                  100                 105                 110 ccc atc atc ctg gtt ggg aat aag aag gat ctt cgg aat gat gag cac       504
Pro Ile Ile Leu Val Gly Asn Lys Lys Asp Leu Arg Asn Asp Glu His
                115                 120                 125 aca agg cgg gag cta gcc aag atg aag cag gag ccg gtg aaa cct gaa       552
Thr Arg Arg Glu Leu Ala Lys Met Lys Gln Glu Pro Val Lys Pro Glu
        130                 135                 140 gaa ggc aga gat atg gca aac agg att ggc gct ttt ggg tac atg gag       600
Glu Gly Arg Asp Met Ala Asn Arg Ile Gly Ala Phe Gly Tyr Met Glu
145                 150                 155 tgt tca gca aag acc aaa gat gga gtg aga gag gtt ttt gaa atg gct       648
Cys Ser Ala Lys Thr Lys Asp Gly Val Arg Glu Val Phe Glu Met Ala
            160                 165                 170 acg aga gct gct ctg caa gct aga cgt ggg aag aaa aaa tct ggg tgc       696
Thr Arg Ala Ala Leu Gln Ala Arg Arg Gly Lys Lys Lys Ser Gly Cys
175                 180                 185                 190 ctt gtc ttg tgaaaccttg ctgcaagcac agcccttatg cggttaattt              745
Leu Val Leu tgaagtgctg tttattaatc ttagtgtatg attactggcc ttttcatttt atctataatt     805
tacctaagat tacaaatcag aagtcatctt gctaccagta tttagaagcc aactatgatt     865
attaacgatg tccaacccgt ctggcccacc agggtccttt tgacactgct ctaacagccc     925
tcctctgcac tcccacctga cacaccaggc gctaattcaa ggaatttctt aacttcttgc     985
ttctttctag aaagagaaac agttggtaac ttttgtgaat taggctgtaa ctactttata   1045
actaacatgt cctgcctatt atctgtcagc tgcaaggtac tctggtgagt caccacttca   1105
```

```
gggctttact ccgtaacaga ttttgttggc atagctctgg ggtgggcagt tttttgaaaa    1165
tgggctcaac cagaaaagcc caagttcatg cagctgtggc agagttacag ttctgtggtt    1225
tcatgttagt taccttatag ttactgtgta attagtgcca cttaatgtat gttaccaaaa    1285
ataaatatat ctaccccaga ctagatgtag tattttttgt ataattggat ttcctaatac    1345
tgtcatcctc aaagaaagtg tattggtttt ttaaaaaaga aagtgtattt ggaaataaag    1405
tcagatggaa aattcaaaaa aaaaaaaaaa aaaactcgag catgcatcta gagggccta    1465 ttctatagtg tcacctaaat gctagagctc gctgatcagc ctcgactgtg ccttctagtt    1525
gccagccatc tgttgtttgc ccctcccccg tgccttcctt gacccctggaa ggtgccactc    1585 ccactgtcct ttcctaataa aatgaggaaa ttgcatcgca ttgtctgagt aggtgtcatt    1645
ctattctggg gggtggggtg gggcaggaca gcaaggggga ggattgggaa gacaatagca    1705
ggcatgctgg ggatgcggtg ggctctatgg cttctgaggc ggaaagaacc agctggggct    1765 ctaggggta tccccacgcg ccctgtagcg gcgcattaag cgcggcgggt gtggtggtta    1825
cgcgcagcgt gaccgctaca cttgccagcg ccctagcgcc cgctcctttc gctttcttcc    1885
cttcctttct cgccacgttc gccggctttc cccgtcaagc tctaaatcgg ggcatccctt    1945
tagggttccg atttagtgct ttacggcacc tcgacccaaa aaaacttgat tagggtgatg    2005
gttcacgtag tgggccatcg cccctgataga cggttttcg ccctttgacg ttggagtcca    2065
cgttctttaa tagtggactc ttgttccaaa ctggaacaac actcaaccct atctcggtct    2125
attcttttga tttataaggg attttgggga tttcggccta ttggttaaaa aatgagctga    2185
tttaacaaaa atttaacgcg aattaattct gtggaatgtg tgtcagttag ggtgtggaaa    2245
gtccccaggc tccccaggca ggcagaagta tgcaaagcat gcatctcaat tagtcagcaa    2305
ccaggtgtgg aaagtcccca ggctccccag caggcagaag tatgcaaagc atgcatctca    2365
attagtcagc aaccatagtc ccgcccctaa ctccgcccat cccgcccta actccgccca    2425 gttccgccca ttctccgccc catggctgac taatttttt tatttatgca gaggccgagg    2485
ccgcctctgc ctctgagcta ttccagaagt agtgaggagg ctttttgga ggcctaggct    2545 tttgcaaaaa gctcccggga gcttgtatat ccatttccgg atctgatcaa gagacaggat    2605
gaggatcgtt tcgcatgatt gaacaagatg gattgcacgc aggttctccg gccgcttggg    2665
tggagaggct attcggctat gactgggcac aacagacaat cggctgctct gatgccgccg    2725
tgttccggct gtcagcgcag gggcgcccgg ttcttttgt caagaccgac ctgtccggtg    2785
ccctgaatga actgcaggac gaggcagcgc ggctatcgtg gctggccacg acgggcgttc    2845
cttgcgcagc tgtgctcgac gttgtcactg aagcgggaag ggactggctg ctattgggcg    2905
aagtgccggg gcaggatctc ctgtcatctc accttgctcc tgccgagaaa gtatccatca    2965
tggctgatgc aatgcggcgg ctgcatacgc ttgatccggc tacctgccca ttcgaccacc    3025
aagcgaaaca tcgcatcgag cgagcacgta ctcggatgga agccggtctt gtcgatcagg    3085
atgatctgga cgaagagcat caggggctcg cgccagccga actgttcgcc aggctcaagg    3145
cgcgcatgcc cgacggcgag gatctcgtcg tgacccatgg cgatgcctgc ttgccgaata    3205
tcatggtgga aaatggccgc ttttctggat tcatcgactg tggccggctg ggtgtggcgg    3265
accgctatca ggacatagcg ttggctaccc gtgatattgc tgaagagctt ggcggcgaat    3325
gggctgaccg cttcctcgtg ctttacggta tcgccgctcc cgattcgcag cgcatcgcct    3385
tctatcgcct tcttgacgag ttcttctgag cgggactctg gggttcgaaa tgaccgacca    3445
```

```
agcgacgccc aacctgccat cacgagattt cgattccacc gccgccttct atgaaaggtt    3505
gggcttcgga atcgtttttcc gggacgccgg ctggatgatc ctccagcgcg gggatctcat    3565
gctggagttc ttcgcccacc ccaacttgtt tattgcagct tataatggtt acaaataaag    3625
caatagcatc acaaatttca caaataaagc atttttttca ctgcattcta gttgtggttt    3685
gtccaaactc atcaatgtat cttatcatgt ctgtataccg tcgacctcta gctagagctt    3745
ggcgtaatca tggtcatagc tgtttcctgt gtgaaattgt tatccgctca caattccaca    3805
caacatacga gccggaagca taaagtgtaa agcctggggt gcctaatgag tgagctaact    3865
cacattaatt gcgttgcgct cactgcccgc tttccagtcg ggaaacctgt cgtgccagct    3925
gcattaatga atcggccaac gcgcggggag aggcggtttg cgtattgggc gctcttccgc    3985
ttcctcgctc actgactcgc tgcgctcggt cgttcggctg cggcgagcgg tatcagctca    4045
ctcaaaggcg gtaatacggt tatccacaga atcagggga aacgcaggaa agaacatgtg    4105
agcaaaaggc cagcaaaagg ccaggaaccg taaaaaggcc gcgttgctgg cgttttccca    4165
taggctccgc ccccctgacg agcatcacaa aaatcgacgc tcaagtcaga ggtggcgaaa    4225
cccgacagga ctataaagat accaggcgtt tccccctgga agctccctcg tgcgctctcc    4285
tgttccgacc ctgccgctta ccggatacct gtccgccttt ctcccttcgg gaagcgtggc    4345
gctttctcaa tgctcacgct gtaggtatct cagttcggtg taggtcgttc gctccaagct    4405
gggctgtgtg cacgaacccc ccgttcagcc cgaccgctgc gccttatccg gtaactatcg    4465
tcttgagtcc aacccggtaa gacacgactt atcgccactg gcagcagcca ctggtaacag    4525
gattagcaga gcgaggtatg taggcggtgc tacagagttc ttgaagtggt ggcctaacta    4585
cggctacact agaaggacag tatttggtat ctgcgctctg ctgaagccag ttaccttcgg    4645
aaaaagagtt ggtagctctt gatccggcaa acaaaccacc gctggtagcg gtggtttttt    4705
tgtttgcaag cagcagatta cgcgcagaaa aaaaggatct caagaagatc ctttgatctt    4765
ttctacgggg tctgacgctc agtggaacga aaactcacgt taagggattt tggtcatgag    4825
attatcaaaa aggatcttca cctagatcct tttaaattaa aaatgaagtt ttaaatcaat    4885
ctaaagtata tatgagtaaa cttggtctga cagttaccaa tgcttaatca gtgaggcacc    4945
tatctcagcg atctgtctat ttcgttcatc catagttgcc tgactccccg tcgtgtagat    5005
aactacgata cgggagggct taccatctgg ccccagtgct gcaatgatac cgcgagaccc    5065
acgctcaccg gctccagatt tatcagcaat aaaccagcca gccggaaggg ccgagcgcag    5125
aagtggtcct gcaactttat ccgcctccat ccagtctatt aattgttgcc gggaagctag    5185
agtaagtagt tcgccagtta atagtttgcg caacgttgtt gccattgcta caggcatcgt    5245
ggtgtcacgc tcgtcgtttg gtatggcttc attcagctcc ggttcccaac gatcaaggcg    5305
agttacatga tcccccatgt tgtgcaaaaa agcggttagc tccttcggtc ctccgatcgt    5365
tgtcagaagt aagttggccg cagtgttatc actcatggtt atggcagcac tgcataattc    5425
tcttactgtc atgccatccg taagatgctt ttctgtgact ggtgagtact caaccaagtc    5485
attctgagaa tagtgtatgc ggcgaccgag ttgctcttgc ccggcgtcaa tacgggataa    5545
taccgcgcca catagcagaa ctttaaaagt gctcatcatt ggaaaacgtt cttcggggcg    5605
aaaactctca aggatcttac cgctgttgag atccagttcg atgtaaccca ctcgtgcacc    5665
caactgatct tcagcatctt ttactttcac cagcgtttct gggtgagcaa aaacaggaag    5725
gcaaaatgcc gcaaaaaagg gaataagggc gacacgaaaa tgttgaatac tcatactctt    5785
cctttttcaa tattattgaa gcatttatca gggttattgt ctcatgagcg gatacatatt    5845
```

-continued

```
tgaatgtatt tagaaaaata aacaaatagg ggttccgcgc acatttcccc gaaaagtgcc    5905
acctgacgtc gacggatcgg gagatctccc gatcccctat ggtcgactct cagtacaatc    5965
tgctctgatg ccgcatagtt aagccagtat ctgctccctg cttgtgtgtt ggaggtcgct    6025
gagtagtgcg cgagcaaaat ttaagctaca acaaggcaag gcttgaccga caattgcatg    6085
aagaatctgc ttagggttag gcgttttgcg ctgcttcgcg atgtacgggc cagatatacg    6145
cgttgacatt gattattgac tagttattaa tagtaatcaa ttacgggtc attagttcat     6205 agcccatata tggagttccg cgttacataa cttacggtaa atggcccgcc tggctgaccg    6265
cccaacgacc cccgcccatt gacgtcaata atgacgtatg ttcccatagt aacgccaata    6325
gggactttcc attgacgtca atgggtggac tatttacggt aaactgccca cttggcagta    6385
catcaagtgt atcatatgcc aagtacgccc cctattgacg tcaatgacgg taaatggccc    6445
gcctggcatt atgcccagta catgacctta tgggactttc ctacttggca gtacatctac    6505
gtattagtca tcgctattac catggtgatg cggttttggc agtacatcaa tgggcgtgga    6565
tagcggtttg actcacgggg atttccaagt ctccacccca ttgacgtcaa tgggagtttg    6625
ttttggcacc aaaatcaacg ggactttcca aaatgtcgta acaactccgc cccattgacg    6685
caaatgggcg gtaggcgtgt acggtgggag gtctatataa gcagagctct ctggctaact    6745
agagaaccca ctgcttactg gcttatcgaa attaatacga ctcactatag ggagacccaa    6805
gcttggtacc gagctcggat ccactagtaa cggccgccag tgtgctgg                 6853
```

<210> SEQ ID NO 24
<211> LENGTH: 193
<212> TYPE: PRT
<213> ORGANISM: Artificial Sequence
<220> FEATURE:
<223> OTHER INFORMATION: Plasmid pcDNA3 hRhoA wt

<400> SEQUENCE: 24

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
```

```
            180             185             190
Leu

<210> SEQ ID NO 25
<211> LENGTH: 28
<212> TYPE: DNA
<213> ORGANISM: Artificial Sequence
<220> FEATURE:
<223> OTHER INFORMATION: PCR Primer RAGE_SE

<400> SEQUENCE: 25
ccgaattccg gaagcaggat ggcagccg                                           28

<210> SEQ ID NO 26
<211> LENGTH: 32
<212> TYPE: DNA
<213> ORGANISM: Artificial Sequence
<220> FEATURE:
<223> OTHER INFORMATION: PCR Primer RAGE_AS

<400> SEQUENCE: 26
ccctcgagcc cctcaaggcc ctcagtacta ct                                      32

<210> SEQ ID NO 27
<211> LENGTH: 31
<212> TYPE: DNA
<213> ORGANISM: Artificial Sequence
<220> FEATURE:
<223> OTHER INFORMATION: PCR Primer N-SE A

<400> SEQUENCE: 27
agtaacggcc gccagtgtgc tggaattcgg a                                       31

<210> SEQ ID NO 28
<211> LENGTH: 32
<212> TYPE: DNA
<213> ORGANISM: Artificial Sequence
<220> FEATURE:
<223> OTHER INFORMATION: PCR Primer C-SE B

<400> SEQUENCE: 28
ccggtaccac ctgcagttgg cccctcctcg cc                                      32

<210> SEQ ID NO 29
<211> LENGTH: 34
<212> TYPE: DNA
<213> ORGANISM: Artificial Sequence
<220> FEATURE:
<223> OTHER INFORMATION: PCR Primer hNogo HindIII

<400> SEQUENCE: 29
ccaagcttat gaagagggcg tccgctggag ggag                                    34

<210> SEQ ID NO 30
<211> LENGTH: 35
<212> TYPE: DNA
<213> ORGANISM: Artificial Sequence
<220> FEATURE:
<223> OTHER INFORMATION: PCR Primer hNogo EcoRI-TM

<400> SEQUENCE: 30
ccgaattcta gggcacctga gccttctgag tcacc                                   35

<210> SEQ ID NO 31
<211> LENGTH: 30
```

```
<212> TYPE: PRT
<213> ORGANISM: Artificial Sequence
<220> FEATURE:
<223> OTHER INFORMATION: Peptide 5

<400> SEQUENCE: 31

Asp Gly Lys Pro Leu Val Pro Asn Glu Lys Gly Val Ser Val Lys Glu
1               5                   10                  15

Gln Thr Arg Arg His Pro Glu Thr Gly Leu Phe Thr Leu Gln
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Peptide 6

<400> SEQUENCE: 32

Thr Leu Gln Ser Glu Leu Met Val Thr Pro Ala Arg Gly Gly Asp Pro
1               5                   10                  15

Arg Pro Thr Phe Ser Cys Ser Phe Ser Pro Gly Leu Pro Arg
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Peptide 7

<400> SEQUENCE: 33

Leu Pro Arg His Arg Ala Leu Arg Thr Ala Pro Ile Gln Pro Arg Val
1               5                   10                  15

Trp Glu Pro Val Pro Leu Glu Glu Val Gln Leu Val Val Glu
            20                  25                  30

<210> SEQ ID NO 34
<211> LENGTH: 256
<212> TYPE: PRT
<213> ORGANISM: Artificial Sequence
<220> FEATURE:
<223> OTHER INFORMATION: N-terminally truncated sRAGE comprising amino
      acids102-331 of human RAGE
<220> FEATURE:
<221> NAME/KEY: MISC_FEATURE
<222> LOCATION: (231)..(250)
<223> OTHER INFORMATION: myc tag
<220> FEATURE:
<221> NAME/KEY: MISC_FEATURE
<222> LOCATION: (1)..(230)
<223> OTHER INFORMATION: amino acids 102  to 331 of human sRAGE
<220> FEATURE:
<221> NAME/KEY: MISC_FEATURE
<222> LOCATION: (251)..(260)
<223> OTHER INFORMATION: his tag

<400> SEQUENCE: 34

Met Asn Arg Asn Gly Lys Glu Thr Lys Ser Asn Tyr Arg Val Arg Val
1               5                   10                  15

Tyr Gln Ile Pro Gly Lys Pro Glu Ile Val Asp Ser Ala Ser Glu Leu
            20                  25                  30

Thr Ala Gly Val Pro Asn Lys Val Gly Thr Cys Val Ser Glu Gly Ser
        35                  40                  45

Tyr Pro Ala Gly Thr Leu Ser Trp His Leu Asp Gly Lys Pro Leu Val
    50                  55                  60
```

-continued

```
Pro Asn Glu Lys Gly Val Ser Val Lys Glu Gln Thr Arg Arg His Pro
 65                  70                  75                  80

Glu Thr Gly Leu Phe Thr Leu Gln Ser Glu Leu Met Val Thr Pro Ala
             85                  90                  95

Arg Gly Gly Asp Pro Arg Pro Thr Phe Ser Cys Ser Phe Ser Pro Gly
            100                 105                 110

Leu Pro Arg His Arg Ala Leu Arg Thr Ala Pro Ile Gln Pro Arg Val
        115                 120                 125

Trp Glu Pro Val Pro Leu Glu Glu Val Gln Leu Val Val Glu Pro Glu
130                 135                 140

Gly Gly Ala Val Ala Pro Gly Gly Thr Val Thr Leu Thr Cys Glu Val
145                 150                 155                 160

Pro Ala Gln Pro Ser Pro Gln Ile His Trp Met Lys Asp Gly Val Pro
                165                 170                 175

Leu Pro Leu Pro Pro Ser Pro Val Leu Ile Leu Pro Glu Ile Gly Pro
            180                 185                 190

Gln Asp Gln Gly Thr Tyr Ser Cys Val Ala Thr His Ser Ser His Gly
        195                 200                 205

Pro Gln Glu Ser Arg Ala Val Ser Ile Ser Ile Glu Pro Gly Glu
    210                 215                 220

Glu Gly Pro Thr Ala Gly Ala Arg Gly Gly Pro Glu Gln Lys Leu Ile
225                 230                 235                 240

Ser Glu Glu Asp Leu Asn Ser Ala Val Asp His His His His His His
                245                 250                 255

<210> SEQ ID NO 35
<211> LENGTH: 36
<212> TYPE: DNA
<213> ORGANISM: Artificial Sequence
<220> FEATURE:
<223> OTHER INFORMATION: PCR Primer

<400> SEQUENCE: 35
cgaagcttga tgaacaggaa tggaaggag accaag                                36

<210> SEQ ID NO 36
<211> LENGTH: 34
<212> TYPE: DNA
<213> ORGANISM: Artificial Sequence
<220> FEATURE:
<223> OTHER INFORMATION: PCR Primer

<400> SEQUENCE: 36
tcctcgagca cctgcagttg gcccctcctc gcct                                 34

<210> SEQ ID NO 37
<211> LENGTH: 358
<212> TYPE: PRT
<213> ORGANISM: Artificial Sequence
<220> FEATURE:
<223> OTHER INFORMATION: sRAGE comprising amino acids1-331 of human RAGE
<220> FEATURE:
<221> NAME/KEY: MISC_FEATURE
<222> LOCATION: (353)..(358)
<223> OTHER INFORMATION: His tag
<220> FEATURE:
<221> NAME/KEY: MISC_FEATURE
<222> LOCATION: (332)..(352)
<223> OTHER INFORMATION: Myc tag
<220> FEATURE:
<221> NAME/KEY: MISC_FEATURE
<222> LOCATION: (1)..(331)
```

<223> OTHER INFORMATION: sRAGE

<400> SEQUENCE: 37

```
Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Gly Thr Lys Leu Gly
                325                 330                 335

Pro Glu Gln Lys Leu Ile Ser Glu Glu Asp Leu Asn Ser Ala Val Asp
            340                 345                 350

His His His His His His
            355
```

AGER-PEPTIDES AND USE THEREOF

CROSS-REFERENCE TO RELATED APPLICATION(S)

This is a U.S. national stage entry of International Patent Application No. PCT/EP2006/000420, filed on Jan. 18, 2006, which claims priority to U.S. Provisional Patent Application No. 60/681,211, filed on May 13, 2005, U.S. Provisional Patent Application No. 60/668,704, filed on Apr. 5, 2005, U.S. Provisional Patent Application No. 60/645,211, filed on Jan. 18, 2005, German Patent Application No. 10 2005 022 285.4, filed on May 13, 2005, German Patent Application No. 10 2005 015 832.3, filed on Apr. 6, 2005, and German Patent Application No. 10 2005 002 353.3, filed on Jan. 18, 2005.

The present invention relates to the identification, functionality and use of domains from the N terminus of the receptor for advanced glycation end products (AGER or RAGE). These domains, called receptor multimerization epitope (RME), are highly conserved in all AGER protein sequences. They represent the mediators for AGER self-association and heteromerization with other proteins. The invention likewise relates to the identification, functionality and use of peptides derived from the C domain of AGER (AGER-CDP). The AGER-RMEs and AGER-CDPs of the invention are suitable as target for identifying AGER ligands which modulate the natural ligand interaction; as immunogen for active or passive immunization of individuals, as diagnostic means for identifying immunogenic reactions, and as peptide ligands for modulating protein-protein interactions involving AGER.

PRIOR ART

It is known from the prior art that numerous human disorders are associated with an increased occurrence of AGER or AGER-binding ligands (Jerums G et al.: Arch Biochem Biophys. 2003 Nov. 1; 419(1):55-62.; Bucciarelli L G et al.: Cell Mol Life Sci. 2002 July; 59(7):1117-28; Hofmann H S et al.: Am J Respir Crit. Care Med. 2004 Sep. 1; 170(5):516-9.; Lotze M T et al: Curr Opin Investig Drugs. 2003 December; 4(12):1405-9).

WO-A-2004/016229 describes N-terminal AGER fragments capable of ligand binding (RAGE-LBE) and proposes their use inter alia (as fusion protein with an immunoglobulin element) for the treatment of AGER-associated disorders. Examples mentioned of such disorders are amyloidoses, cancer, arthritis, Crohn's disease, chronic inflammatory disorders, acute inflammatory disorders, cardiovascular disorders, diabetes, diabetic complications, prion-associated disorders, vasculitis, nephropathies, retinopathies and neuropathies. AGER-associated disorders which are particularly mentioned are: Alzheimer's, rheumatoid arthritis, osteoarthritis, bowel disease, multiple sclerosis, psoriasis, lupus, autoimmune disease in general, sepsis, arteriosclerosis and restenosis It is particularly proposed in the international patent application that AGER fragments with a length of 118-344 amino acids (starting in each case at the first N-terminal residue of the receptor) are used. Shorter fragments are not described. The WO specification also makes a general reference to the possible therapeutic usefulness of isolated antibodies which are specifically immunoreactive with an epitope of the AGER amino acid sequence. No specific epitopes are proposed, nor are specific antibodies produced.

It is therefore an object of the present invention to provide novel therapeutic approaches to the treatment of AGER-associated disorders.

BRIEF DESCRIPTION OF THE INVENTION

The above object has surprisingly been achieved by isolating and characterizing specific receptor multimerization epitopes (RME) and peptides of the Ig-like C domain of AGER.

DESCRIPTION OF THE FIGURES

FIG. 1 shows a sequence comparison (ClustAll W alignment) of human, mouse, rat and bovine RAGE. The sequence segment corresponding to NtermR31 is identified by "I+ . . . +I". Indications of sequence agreement are to be found in each case in the last line of a sequence block. Identical amino acid positions are identified by "*", while "." and ":" represent similar amino acids; if agreement is absent, a space (" ") has been entered. The Ig-like domain of the V type (V domain) is emphasized for the human sequence by bold underlining, the Ig-like domain C2 type 1 is emphasized for the human sequence by broken underlining, the Ig-like domain C2 type 2 is emphasized for the human sequence by bold broken underlining.

FIG. 4b shows the result of a FACS analysis for expressed cell surface receptors hNgR and hp75 of an HEK293 triple transfectant produced according to the invention (clone #4 and #8) and of untransformed HEK293 cells (top), in each case for analyses with Anti-p75 and anti-NgR antibodies.

FIG. 10A illustrates the competition for binding of AP-Nogo-66 (0.1 nM) to the Nogo rezeptor (NogoR) by sRAGE (circles) and soluble His-NogoR (triangles) as a function of the respective competitor concentration; FIG. 10B shows the competition for the binding of AP-Nogo66 (0.1 nM) to the Nogo receptor by NtermR31 as a function of the respective competitor concentration.

FIG. 12a shows immunohistological investigations on thin sections of transgenic APP mouse brain using commercial anti-RAGE antibodies. Strong stimulation of membrane-bound RAGE is to be seen in the gyrus dentatus of 10-week old mice (left-hand picture) at a time when no amyloid plaques have yet formed. When there is extensive formation of amyloid and development of plaques (from month 9 to 12 of life), membrane-bound RAGE disappears in favor of soluble RAGE. This explains the distinctly weaker staining in 11-month old mice (right-hand picture).

FIG. 21 shows the competition of sRAGE-A13 globulomer binding with the monoclonal anti-RAGE antibodies ML37-6A6 and ML37-11H8 compared with nonspecific mouse IgG1 and 2a.

DETAILED DESCRIPTION OF THE INVENTION

I. Specific Aspects of the Invention

Figure 2:
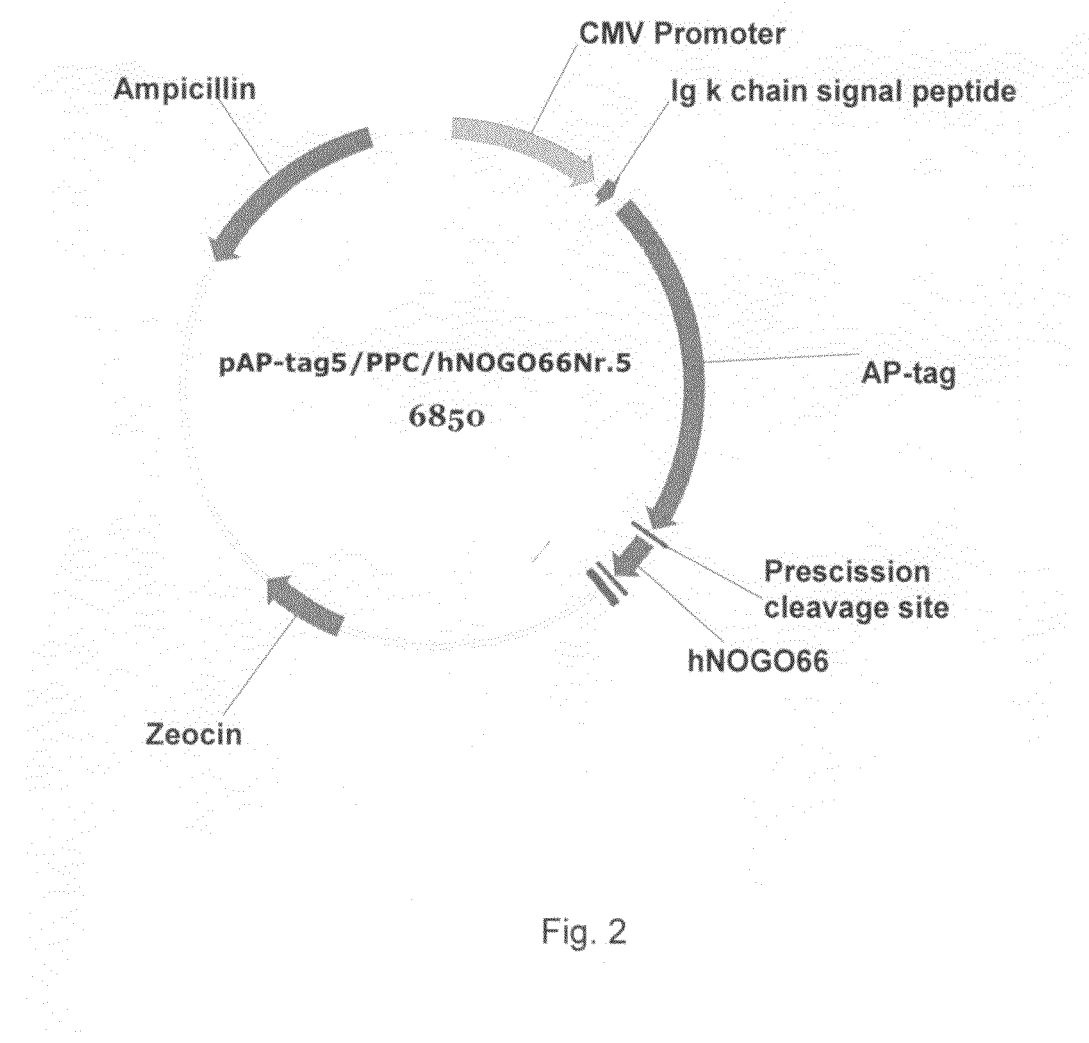
FIG. 2 shows the plasmid map of the plasmid pAP-tag5/PPC/hNOGO66No. 5 used according to the invention.

A first aspect of the invention relates to the use of the receptor multimerization epitope (RME) of the advanced glycation end products receptor (AGER), comprising a peptide fragment, capable of auto-multimerization, of the N-terminal AGER ectodomain, or of a peptide (AGER-CDP) derived from the non-V domain AGER domain, such as in particular an Ig-like C domain (such as in particular from the Ig-like C2 domain, type 1 and/or the Ig-like C2 domain type 2), or of a functional, immunogenic equivalent of AGER-RME or of AGER-CDP, as immunogen for preparing a polyclonal antiserum or monoclonal antibodies against AGER-RME or AGER-CDP.

The AGER-RME employed in this case has in particular a length of about 8 to 50 amino acid residues and is derived from the human AGER ectodomain having an amino acid sequence as shown in Genbank Ref. Seq. sequence NM_001136 or from a functionally equivalent ectodomain, especially from the Ig-like domain of the V type (V domain).

The AGER-RME comprises for example the following sequence:

C(K/R)GAPKKP(P/T)Q(Q/R/K)LE     (SEQ ID NO: 1)

The AGER-RME preferably comprises a sequence selected from

CRGAPKKPPQQLE        (SEQ ID NO: 2)

CKGAPKKPPQRLE        (SEQ ID NO: 3)

CKGAPKKPTQKLE        (SEQ ID NO: 4)

An AGER-RME which can be used according to the invention may, however, also comprise a sequence of the following general formula:

$$X^1—X^2—X^3—X^4$$

in which
X¹ is a hydrogen atom or the amino acid Q or the dipeptide DQ;
X² is NITARIG(K/E)PL(V/M)L(N/S/K) (SEQ ID NO:5);
X³ is a sequence according SEQ ID NO: 1, 2, 3 or 4; and
X⁴ is the peptide sequence WKLN.

For example, AGER-CDPs with a length of about 5 to 50 amino acid residues which are derived from the human AGER ectodomain having an amino acid sequence as shown in Genbank Ref. Seq. sequence NM_001136 or a functionally equivalent ectodomain, in particular an Ig-like C domain, especially the C2 domain type 1 and/or type 2 thereof (cf. also FIG. 1), are employed according to the invention.

Suitable AGER-CDP peptides comprise one of the following sequences:

```
DGKPLVPNEKGVSVKEQTRRHPETGLFTLQ    (SEQ ID NO: 31)

TLQSELMVTPARGGDPRPTFSCSFSPGLPR    (SEQ ID NO: 32)
and

LPRHRALRTAPIQPRVWEPVPLEEVQLVVE.   (SEQ ID NO: 33)
```

Alternatively, the AGER-RME or AGER-CDP, in particular having one of the sequences indicated above, may be in the form of a cyclic peptide.

A further aspect of the invention relates to the use of an AGER-RME or of an AGER-CDP as defined above as diagnostic marker such as, for example, as capture antigen for the diagnosis of diseases or stages of diseases in which autoantibodies against the AGER-RME occur.

A further aspect of the invention relates to the use of an AGER-RME or of an AGER-CDP as defined above, of the AGER ectodomain having an amino acid sequence as shown in Genbank Ref. Seq. sequence NM_001136 and N-terminal subfragments thereof, and of muteins and derivatives of these AGER molecules, or of AGER-RME- or AGER-CDP-binding ligands for producing a pharmaceutical composition for the diagnosis or therapy of AGER-mediated diseases or stages of diseases.

Diseases or stages of diseases which can be treated according to the invention are those associated with an AGER/AGER, AGER/ligand, AGER/receptor, AGER/receptor/ligand, AGER/receptor/coreceptor and/or AGER/receptor/counter-receptor interaction.

Examples of disorders which may be mentioned as associated with an AGER/AGER interaction are: Alzheimer's and amyloidoses; examples which may be mentioned of disorders associated with an AGER/ligand interaction are: Alzheimer's and HIV-associated dementia; examples which may be mentioned of disorders associated with an AGER/receptor interaction are: spinal cord injury and cranial trauma; examples which may be mentioned of disorders associated with an AGER/receptor/coreceptor and/or AGER/receptor/counter-receptor interaction are: multiple sclerosis, sepsis, arteriosclerosis.

The diseases or stages of diseases which can be treated and/or diagnosed according to the invention may further be selected from the following groups:
a) mechanical injuries of the skull and spinal cord;
b) ischaemic damage, such as stroke;
c) chronic disorders selected from neurodegenerative, inflammatory and autoimmune diseases such as, in particular, multiple sclerosis, parkinsonism, Alzheimer's, HIV-1-associated dementia;
d) diabetic sequelae such as diabetic nephropathy, diabetic neuropathy, and diabetic vasculopathy;
e) tumor progression and metastasis;
f) altered neurogenesis processes associated with psychotic disorders such as depression and schizophrenia, and chronic states of pain caused by excessive neurite sprouting and/or pathological synaptogenesis, such as phantom pain following amputation;
g) impairments of neuronal regeneration, of axonal sprouting, of neurite extension and of neuronal plasticity
h) central/peripheral amyloid disorders; and
i) arteriosclerosis.

In a particular embodiment, the AGER-RME- or AGER-CDP-binding ligand is an anti-AGER-RME or anti-AGER-CDP antibody.

A further aspect of the invention relates to the use of AGER-RME or of an AGER-CDP as defined above as target for the detection or identification of AGER-binding ligands.

A further aspect of the invention relates to the use of AGER-RME or of an AGER-CDP as defined above as immunogen for active or passive immunization.

The invention further relates to a polyclonal anti-AGER-RME or anti-AGER-CDP antiserum obtainable by immunization of a mammal with an antigenic amount of an AGER-RME or of an AGER-CDP peptide as defined above.

The invention further relates to monoclonal anti-AGER-RME or anti-AGER-CDP antibodies or antigen-binding fragments thereof, if appropriate in humanized form.

Preferred antibodies or antisera have at least one of the following properties:
a) improved specificity for an AGER-RME or an AGER-CDP as defined above, improved specificity for a new epitope formed with involvement of the AGER-RME or of an AGER-CDP as defined above,
b) inhibition of the AGER-RME-mediated multimerization with sRAGE or anti-AGER-RME antibody (to be observed in particular in an AlphaScreen or assay);
c) specific recognition of an AGER ligand-induced, e.g. a Aβ 1-42-induced, receptor status of sRAGE;
d) induction of a receptor configuration of sRAGE which modulates, such as, for example, promotes, binding of an AGR ligand such as, for example, selected from a Aβ 1-42, Aβ 0-42, Aβ 12-42 and their globulomers, amyloid, AGE, to sRAGE.

The invention further relates to monoclonal, bispecific antibodies comprising
a) a first antigen-binding domain derived from a monoclonal antibody as defined above, and
b) a second antigen-binding domain with specificity for at least one cell surface receptor which are able to interact with AGER-RME or AGER-CDP, such as, for example, AGER, NgR, or with specificity for a ligand, coreceptor or counter-receptor for one of these receptors, or an antigen-binding fragment thereof, if appropriate in humanized form.

The invention further relates to a hybrid protein comprising an AGER-RME or an AGER-CDP as defined above. Such hybrid proteins additionally comprise a functional part of a protein selected from immunoglobulins and fragments thereof, such as, for example, an Ig Fc fragment functionally linked to, for example, the C terminus of AGER-RME or AGER-CDP.

The invention also relates to AGER-RME or AGER-CDP derivatives comprising AGER-RME or AGER-CDP as defined above in PEGylated form or coupled to a, for example optical, enzymatic or radioactive marker.

A further aspect of the invention relates to pharmaceutical compositions comprising in a pharmaceutically acceptable carrier at least one active ingredient selected from:
a) AGER-RME or AGER-CDP as defined above;
b) nucleic acid sequences coding for AGER-RME as defined above;
c) monoclonal or polyclonal anti-AGER-RME or anti-AGER-CDP antibodies as defined above;
d) bispecific antibodies as defined above, and
e) hybrid proteins and derivatives as defined above.

Pharmaceutical compositions of the invention may additionally comprise as further active ingredient an active substance which is selected from:
a) neurotrophic factors such as nerve growth factors, such as, for example, NGF, NT-3, BNDF; inosine; neuroimmunophilins such as FK506, GPI1046; chondroitin sulfate proteoglycan-degrading enzymes such as chondroitinase ABC;
b) antibodies against neurite growth inhibitors; Nogo-A such as the antibodies IN-1, 7B12; MAG; Omgp; and/or their receptors such as anti-NgR and anti-p75 antibodies;
c) soluble NgR fragments; Nogo-A peptide fragments such as NEP1-40 and Nogo66,
d) inhibitors of the p75-mediated signal cascade, such as RHO A inhibitors, ROCK inhibitors such as Y-27632,
e) cAMP and functional analogs, protein kinase A, arginase I, polyamines, ciliary neurotrophis factor.

Pharmaceutical compositions of this type are suitable for example for intrathecal, intravenous, subcutaneous, oral or parenteral, nasal and inhalational administration.

The invention further relates to an immunogen comprising AGER-RME or AGER-CDP as defined above in a pharmaceutically acceptable carrier and, if appropriate, with an adjuvant for active immunization.

The invention also relates to a method for detecting effectors of the AGER receptor, where a sample in which an effector is suspected is incubated with an AGER-RME or an AGER-CDP polypeptide as defined above, and the mixture is investigated for the formation of an effector-AGER-RME complex or effector-AGER-CDP complex.

The invention further relates to expression vectors comprising at least one coding nucleic acid sequence for a linear AGER-RME or AGER-CDP as defined above, operatively linked to at least one regulatory nucleic acid sequence.

The invention additionally relates to recombinant microorganisms which harbor at least one such vector.

The invention also relates to hybridoma cell lines which produce a monoclonal antibody as defined above.

The invention further relates to methods for producing AGER-RME or AGER-CDP as defined above or a hybrid protein comprising the latter, where a recombinant microorganism as defined above is cultivated, and the produced protein product is isolated from the culture.

The invention further relates to methods for producing a monoclonal antibody as defined above, where a hybridoma cell line as defined above is cultivated, and the produced protein product is isolated from the culture.

The invention further comprises functional, in particular immunogenic equivalents of AGER-RME as defined above, which have a degree of homology of less than 100% to SEQ ID NO: 6.

Functional equivalents according to the invention of AGER-RME have at least one of the following properties:

a. inhibition of signal transduction in the actin cytoskeletal rearrangement (ACR) assay;
b. competition with sRAGE for binding with an AGER ligand, such as, for example, Aβ globulomers, Aβ 1-42, Aβ 20-42, AR 12-42, amyloid, AGE;
c. auto-multimerization or multimerization with AGER-RME or s-RAGE.

Functional equivalents according to the invention of AGER-RME may additionally have a core sequence with high positive charge density of the following general formula:

in which
the residues Z are independently of one another an amino acid residue having a positively charged side chain, such as, in particular, lysine and arginine; and
the residues $X^1$ and $X^2$ are independently of one another any 1 to 5 identical or different amino acids which have no positively charged side chains.

A further aspect of the invention relates to combinations of at least one first and at least one second monoclonal antibodies differing in antigenic specificity, where at least one first monoclonal antibody (or a group of 2 or more, such as, for example, 2, 3 or 4, first monoclonal antibody) binds to an antigen which is formed wholly or partly from a sequence region of the Ig-like V domain of AGER (or sRAGE), and at least one second monoclonal antibody (or a group of 2 or more, such as, for example, 2, 3 or 4, second monoclonal antibody) binds to an antigen which is formed wholly or partly from a sequence region of an AGER domain (non-V domain) different from the Ig-like V domain.

Those antibody combinations where the AGER domain different from the Ig-like V domain is an Ig-like C domain (for example comprising C2 type 1 and/or C2 type 2) of AGER are described in particular.

Also described are those antibody combinations where at least one first monoclonal antibody and, if appropriate, at least one second monoclonal antibody competes with the binding of AGER or a soluble equivalent thereof with an AGER binding partner such as, for example, an AR globulomer.

The invention also relates to the use of such antibody combinations as medicaments.

The invention further relates to pharmaceutical compositions comprising an antibody combination as defined above.

The invention additionally relates to the use of antibody combinations of the invention for producing a pharmaceutical composition for the therapy of diseases or pathological states as defined above.

II. Explanations of General Terms

The designation "receptors" is given in the context of the present invention in particular to surface molecules which are bound to a cell membrane and which can interact with a, for example soluble, ligand and, as a consequence of this interaction, can initiate a signal which is directed for example into the interior of the cell, or a signal cascade (also referred to as signaling).

The designation "coreceptors" is given to membrane structural elements which are located in the same cell as the receptor. The coreceptor is necessary to define and/or to modulate the functionality of the receptor.

The designation "counter-receptors" is given to membrane-bound surface molecules which are located on two different (adjacent) cells and which can come into mutual contact and thus initiate signaling.

The designation "ligand" is given to a natural, i.e. in vivo produced, or artificially generated, low or high molecular weight binding partner for a "receptor". The ligand is preferably capable of free movement in the extracellular environment.

A "receptor multimerization epitope" (RME) means a peptide fragment which is capable in particular of auto-multimerization and can thus form dimeric, trimeric, tetrameric etc. complexes with oligo- or polypeptides having substantially the same amino acid sequence. The RME may additionally be capable of hetero-multimerization, and form complexes with at least one oligo- or polypeptide differing therefrom. The complex formation can be detectable for example by gel chromatography, native gel electrophoresis, if appropriate after stabilization of the complexes by crosslinking, e.g. with customary methods of protein biochemistry.

The designation "immunogen" is given to a peptide fragment of the invention in glycosylated or non-glycosylated form, which is suitable for inducing the formation of antibodies against the immunogen. Binding of the immunogen (as hapten) to a macromolecular carrier may be advantageous if appropriate.

The designation "epitope" or antigenic determinant is given to the region which defines the antibody specificity of an antigen such as, for example, a protein. If this epitope is newly formed in a segment of the protein, or expressed on the accessible molecular surface for example through external influences such as, for example, an interaction of a protein with a ligand, the term used is "neoepitope".

The designation "domain" of a protein or antibody is given to a complex structure formed by alpha-helix and/or beta-pleated sheet elements and demarcated within the protein. sRAGE comprises for example Ig-like domains of the V type and C2 type 1 and C2 type 2 domains, as illustrated in FIG. 1.

"sRAGE" comprises a soluble form of the AGER ectodomaine such as, for example, sRAGE 1-331 as shown in SEQ ID NO:37). Unless indicated otherwise, sRAGE means in particular sRAGE 1-331.

The AGER "V domain" designates an Ig-like sequence segment to be found in the region of the N terminus of the AGER molecule, as illustrated in FIG. 1 for various AGER molecules, such as, in particular, partial sequences corresponding to residues 23-115 (Ala23-Val115) of the human sequence in FIG. 1. An AGER "non-V domain" is to be found C-terminally of the above-identified V domain in the AGER molecule. Examples of such non-V domains are the Ig-like C domains, in particular C2 domains of type 1 and type 2 as illustrated in FIG. 1 for various AGER molecules.

III. Further Information on Implementation of the Invention

1. Polypeptides

The invention relates in particular to receptor multimerization epitopes (RME) of the advanced glycation end product receptor (AGER), comprising a peptide fragment, capable of auto-multimerization, of the N-terminal AGER ectodomain, or of a functional immunogenic equivalent of AGER-RME. AGER-RME which are preferred according to the invention are linear or cyclic peptides having a length of about 8 to 50 amino acid residues derived from the human AGER ectodomain having an amino acid sequence as shown in Genbank Ref. Seq. sequence NM_001136 or a functionally equivalent ectodomain.

Preferred AGER-RME may comprise the following sequence

C(K/R)GAPKKP(P/T)Q(Q/R/K)LE    (SEQ ID NO: 1)

and in particular one of the sequences

```
CRGAPKKPPQQLE       (SEQ ID NO: 2)
CKGAPKKPPQRLE       (SEQ ID NO: 3)
CKGAPKKPTQKLE.      (SEQ ID NO: 4)
```

The invention also relates to AGER-CDP peptides having a length of about 5 to 50 amino acid residues which are derived from the human AGER ectodomain having an amino acid sequence as shown in Genbank Ref. Seq. sequence NM_001136 or a functionally equivalent ectodomain, in particular an Ig-like C domain thereof.

Examples of suitable AGER-CDP peptides comprise one of the following sequences:

```
DGKPLVPNEKGVSVKEQTRRHPETGLFTLQ    (SEQ ID NO: 31)
TLQSELMVTPARGGDPRPTFSCSFSPGLPR    (SEQ ID NO: 32)
and
LPRHRALRTAPIQPRVWEPVPLEEVQLVVE.   (SEQ ID NO: 33)
```

The invention also comprises likewise "functional equivalents" of the specifically disclosed novel polypeptides.

"Functional equivalents" or analogs of the specifically disclosed AGER-RME polypeptides are in the context of the present invention polypeptides which differ therefrom, such as, for example, those having a degree of homology of less than 100% to SEQ ID NO: 6 (Nterm 31) or SEQ ID NO:3 (Nterm 13), but which continue to have the desired biological activity, such as, for example, inhibition of signal transduction in the actin cytoskeletal rearrangement (ACR) assay; competition with sRAGE for binding with an AGER ligand; auto-multimerization or multimerization with AGER-RME or s-RAGE.

"Functional equivalents" or analogs of the specifically disclosed AGER-CDP polypeptides are in the context of the present invention polypeptides which differ therefrom, such as, for example, those having a degree of homology of less than 100% to SEQ ID NO: 31, 32 or 33 but which continue to have the desired biological activity, such as, for example, the inhibition, described in the examples, of sRAGE-Aβ-1-42 oligomer binding.

Functional equivalents of AGER-RME may, however, also have a characteristic core sequence or lead structure with high positive charge density of the following general formula

ZX$^1$ZZX$^2$Z in which the residues Z are independently of one another an amino acid residue with a positively charged side chain; and the residues X$^1$ and X$^2$ are independently of one another any 1 to 5 identical or different amino acids which have no positively charged side chains.

"Functional equivalents" mean according to the invention in particular mutants which have in at least one of the sequence positions of the abovementioned specific sequences an amino acid which differs from that specifically mentioned, but nevertheless have one of the biological activities mentioned herein. "Functional equivalents" thus comprise the mutants obtainable by one or more amino acid additions, substitutions, deletions and/or inversions, it being possible for said changes to occur in any sequence position as long as they lead to a mutant having the profile of properties according to the invention. Functional equivalence exists in particular also when there is a qualitative agreement between the mutant and unmodified polypeptide in the reactivity pattern, i.e. for example identical biological effects are to be observed but differ greatly in the level of expression. Examples of suitable substitutions of amino acid residues are the following:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also precursors of the polypeptides described, and functional derivatives and salts of the polypeptides. The term "salts" means both salts of carboxyl groups and acid addition salts of amino groups of the protein molecules of the invention. Salts of carboxyl groups can be prepared in a manner known per se and comprise inorganic salts such as, for example, sodium, calcium, ammonium, iron and zinc salts, and salts with organic bases such as, for example, amines, such as triethanolamine, arginine, lysine, piperidine and the like. Acid addition salts such as, for example, salts with mineral acids such as hydrochloric acid or sulfuric acid and salts with organic acids, such as acetic acid and oxalic acid are likewise an aspect of the invention.

"Functional derivatives" of polypeptides of the invention can likewise be prepared on functional amino acid side groups or on their N- or C-terminal end with the aid of known techniques. Derivatives of these types comprise for example aliphatic esters of carboxylic acid groups, amides of carboxylic acid groups, obtainable by reaction with ammonia or with a primary or secondary amine; N-acryl derivatives of free amino groups prepared by reaction with acyl groups; or O-acyl derivatives of free hydroxy groups prepared by reaction with acyl groups.

"Functional equivalents" of course also comprise polypeptides obtainable from other organisms, and naturally occurring variants. For example, areas of homologous sequence regions can be found by sequence comparison, and equivalent enzymes can be established on the basis of the specific requirements of the invention.

"Functional equivalents" are moreover fusion proteins having one of the abovementioned polypeptide sequences or functional equivalents derived therefrom, and at least one further heterologous sequence functionally different therefrom in functional N- or C-terminal linkage (i.e. with negligible mutual functional impairment of the portions of the fusion proteins). Nonlimiting examples of such heterologous sequences are, for example, enzymes and immunoglobulins.

"Functional equivalents" also comprised by the invention are homologs of the specifically disclosed proteins. These have at least 60%, preferably at least 75%, in particular at least 85%, such as, for example, 90%, 95% or 99%, homology to one of the specifically disclosed sequences, calculated by the algorithm of Pearson and Lipman, Proc. Natl. Acad, Sci. (USA) 85(8), 1988, 2444-2448. A percentage homology of a homologous polypeptide of the invention means in particular the percentage identity of the amino acid residue based on the complete length of one of the amino acid sequences specifically described herein.

A "derived" amino acid sequence means according to the invention, unless indicated otherwise, a sequence which has an identity of at least 80% or at least 90%, in particular 91%, 92%, 93%, 94%, 95%, 96%, 97%, 98% and 99%, with the initial sequence.

"Identity" between two sequences means identity of the amino acid residues over the complete length of the sequence in each case, such as, for example, the identity calculated by comparison with the aid of the Vector NTI Suite 7.1 Software from Informax (USA) using the Clustal method (Higgins D G, Sharp P M. Fast and sensitive multiple sequence alignments on a microcomputer. Comput Appl. Biosci. 1989 April; 5(2):151-1), setting the following parameters:

Multiple Alignment Parameter:

| Gap opening penalty | 10 |
|---|---|
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| FAST algorithm | on |
|---|---|
| K-tuple size | 1 |
| Gap penalty | 3 |
| Window size | 5 |
| Number of best diagonals | 5 |

In the case where protein glycosylation is possible, equivalents of the invention comprise proteins of the type designated above in deglycosylated or glycosylated form and modified forms obtainable by altering the glycosylation pattern.

Homologs of the peptides of the invention can be identified by screening combinatorial libraries of mutants such as, for example, truncation mutants. For example, it is possible to generate a variegated library of peptide variants by combinatorial mutagenesis at the nucleic acid level, such as, for example, by enzymatic ligation of a mixture of synthetic oligonucleotides. There is a large number of methods which can be used to produce libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide all sequences which encode the desired set of potential protein sequences in one mixture. Methods for synthesizing degenerate oligonucleotides are known to the skilled worker (e.g. Narang, S. A. (1983) Tetrahedron 39:3; Itakura et al. (1984) Annu. Rev.

Biochem. 53:323; Itakura et al., (1984) Science 198:1056; Ike et al. (1983) Nucleic Acids Res. 11:477).

2. Nucleic Acids

The invention further relates to the nucleic acid sequences coding for the AGER-RME or AGER-CDP peptides described above, and nucleic acid sequences derived therefrom.

All nucleic acid sequences of the invention (single- and double-stranded DNA and RNA sequences, such as, for example, cDNA and mRNA) can be prepared in a manner known per se by chemical synthesis from the nucleotide units, such as, for example, by fragment condensation of individual overlapping, complementary nucleic acid units of the double helix. Chemical synthesis of oligonucleotides can take place for example in a known manner by the phosphoamidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods are described in Sambrook et al. (1989), Molecular Cloning: A laboratory manual, Cold Spring Harbor Laboratory Press.

A "derived" nucleic acid sequence means according to the invention, unless indicated otherwise, a sequence which has an identity of at least 80% or at least 90%, in particular 91%, 92%, 93%, 94%, 95%, 96%, 97%, 98% and 99%, with the initial sequence.

"Identity" between two nucleic acids means the identity of the nucleotides over the complete length of the nucleic acid in each case, in particular the identity by comparison with the aid of the Vector NTI Suite 7.1 Software from Informax (USA) using the Clustal method (see above).

The invention also relates to nucleic acid sequences coding for one of the above peptides and their functional equivalents, which can be obtained for example by use of artificial nucleotide analogs.

The invention relates both to isolated nucleic acid molecules which code for peptides of the invention or biologically active segments thereof, and nucleic acid fragments which can be used for example as hybridization probes or primers for identifying or amplifying coding nucleic acids of the invention.

The nucleic acid molecules of the invention may additionally comprise untranslated sequences from the 3' and/or 5' end of the coding region of the gene.

An "isolated" nucleic acid molecule is separated from other nucleic acid molecules which are present in the natural source of the nucleic acid and may moreover be substantially free of other cellular material or culture medium if it is prepared by recombinant techniques, or free of chemical precursors or other chemicals if it is synthesized chemically.

A nucleic acid molecule of the invention can be isolated by means of standard techniques of molecular biology and the sequence information provided by the invention. For example, cDNA can be isolated from a suitable cDNA library by using one of the specifically disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). It is moreover possible to isolate a nucleic acid molecule comprising one of the sequences of the invention or a segment thereof by polymerase chain reaction using the oligonucleotide primers constructed on the basis of this sequence. The nucleic acid amplified in this way can be cloned into a suitable vector and characterized by DNA sequence analysis. The oligonucleotides of the invention can also be prepared by standard synthesis methods, e.g. using an automatic DNA synthesizer.

The invention further comprises the nucleic acid molecules complementary to the specifically described nucleotide sequences, or a segment thereof.

The nucleotide sequences of the invention make it possible to produce probes and primers which can be used for identifying and/or cloning homologous sequences in other cell types and organisms. Such probes and primers usually comprise a nucleotide sequence region which hybridizes under stringent conditions to at least about 12, preferably at least about 25, such as, for example, about 40, 50 or 75, consecutive nucleotides of a sense strand of a nucleic acid sequence of the invention or of a corresponding antisense strand.

Further nucleic acid sequences of the invention are derived from coding sequences for the AGER-RMEs or AGER-CDPs of the invention and differ therefrom by addition, substitution, insertion or deletion of one or more nucleotides, but still code for peptides having the desired profile of properties.

The invention also comprises nucleic acid sequences which comprise so-called silent mutations, or are modified in accordance with the codon usage of a specific original or host organism compared with a specifically mentioned sequence, as well as naturally occurring variants such as, for example, splice variants or allelic variants, thereof. Sequences obtainable by conservative nucleotide substitutions (i.e. the relevant amino acid is replaced by an amino acid of the same charge, size, polarity and/or solubility) are likewise an aspect.

The invention also relates to the molecules derived from the specifically disclosed nucleic acids through sequence polymorphisms. These genetic polymorphisms may exist because of the natural variation between individuals within a population. These natural variations normally result in a variance of from 1 to 5% in the nucleotide sequence of a gene.

The invention further also comprises nucleic acid sequences which hybridize with the abovementioned coding sequences or are complementary thereto. These polynucleotides can be found by screening genomic or cDNA libraries and if appropriate be amplified therefrom by means of PCR with suitable primers, and subsequently isolated for example with suitable probes. A further possibility is the transformation of suitable microorganisms with polynucleotides or vectors of the invention, to multiply the microorganisms and thus the polynucleotides and subsequently to isolate them. An additional possibility is to synthesize polynucleotides of the invention also by a chemical route.

The property of being able to "hybridize" onto polynucleotides means the ability of a polynucleotide or oligonucleotide to bind under stringent conditions to an almost complementary sequence, while there are nonspecific bindings between non-complementary partners under these conditions. For this purpose, the sequences should be 70-100%, preferably 90-100%, complementary. The property of complementary sequences being able to bind specifically to one another is made use of, for example, in the Northern or Southern blotting technique or in the primer binding in PCR or RT-PCR. Oligonucleotides with a length of 30 base pairs or more are normally employed for this purpose. Stringent conditions mean, for example, in the Northern blotting technique the use of a washing solution, for example 0.1×SSC buffer with 0.1% SDS (20×SSC: 3M NaCl, 0.3M Na citrate, pH 7.0), at 50-70° C., preferably 60-65° C., for eluting nonspecifically hybridized cDNA probes or oligonucleotides. In this case, as mentioned above, only nucleic acids with a high degree of complementarity remain bound to one another. The setting up of stringent conditions is known to the skilled worker and is described for example in Ausubel et al., Current Protocols in Molecular Biology, John Wiley & Sons, N.Y. (1989), 6.3.1-6.3.6.

A further aspect of the invention relates to "antisense" nucleic acids. This comprises a nucleotide sequence which is complementary to a coding "sense" nucleic acid. The antisense nucleic acid may be complementary to the entire coding strand or only to a segment thereof. In a further embodiment, the antisense nucleic acid molecule is antisense to a noncoding region of the coding strand of a nucleotide sequence. The term "noncoding region" relates to the sequence segments referred to as 5'- and 3'-untranslated regions.

An antisense oligonucleotide may be, for example, about 5, 10, 15, 20, 25, 30, 35, 40, 45 or 50 nucleotides long. An antisense nucleic acid of the invention can be constructed by chemical synthesis and enzymatic ligation reactions using methods known in the art. An antisense nucleic acid can be synthesized chemically, using naturally occurring nucleotides or variously modified nucleotides which are configured so that they increase the biological stability of the molecules or increase the physical stability of the duplex formed between the antisense and sense nucleic acids. Examples which can be used are phosphorothioate derivatives and acridine-substituted nucleotides. Examples of modified nucleotides which can be used for generating the antisense nucleic acid are, inter alia, 5-fluorouracil, 5-bromouracil, 5-chlorouracil, 5-iodouracil, hypoxanthine, xanthine, 4-acetylcytosine, 5-(carboxyhydroxylmethypuracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, methyl uracil-5-oxyacetate, uracil-5-oxyacetic acid (v), 5-methyl-2-thiouracil, 3-(3-amino-3-N-2-carboxypropyl) uracil, (acp3)w and 2,6-diaminopurine. The antisense nucleic acid may also be produced biologically by using an expression vector into which a nucleic acid has been subcloned in the antisense direction.

3. Expression constructs and vectors

The invention additionally relates to expression constructs comprising, under the genetic control of regulatory nucleic acid sequences, a nucleic acid sequence coding for an AGER-RME or AGER-CDP of the invention or functional equivalent or immunglobulin, and to vectors comprising at least one of these expression constructs.

Such constructs of the invention preferably comprise a promoter 5'-upstream from the particular coding sequence, and a terminator sequence 3'-downstream, and, if appropriate, other usual regulatory elements, in particular each operatively linked to the coding sequence. "Operative linkage" means the sequential arrangement of promoter, coding sequence, terminator and, if appropriate, other regulatory elements in such a way that each of the regulatory elements is able to comply with its function as intended for expression of the coding sequence. Examples of sequences which can be operatively linked are targeting sequences and enhancers, polyadenylation signals and the like. Other regulatory elements comprise selectable markers, amplification signals, origins of replication and the like. Suitable regulatory sequences are described, for example, in Goeddel, Gene Expression Technology: Methods in Enzymology 185, Academic Press, San Diego, Calif. (1990).

In addition to the artificial regulatory sequences it is possible for the natural regulatory sequence still to be present in front of the actual structural gene. This natural regulation can, if appropriate, be switched off by genetic modification, and expression of the genes can be increased or decreased. The gene construct can, however, also have a simpler structure, that is to say no additional regulatory signals are inserted in front of the structural gene, and the natural promoter with its regulation is not deleted. Instead, the natural regulatory sequence is mutated so that regulation no longer takes place, and gene expression is enhanced or diminished. The nucleic acid sequences may be present in one or more copies in the gene construct.

Examples of promoters which can be used are: cos, tac, trp, tet, trp-tet, lpp, lac, lpp-lac, lacIq, T7, T5, T3, gal, trc, ara, SP6, lambda-PR or lambda-PL promoter, which are advantageously used in Gram-negative bacteria; and the Gram-positive promoters amy and SPO2, the yeast promoters ADC1, MFalpha, AC, P-60, CYC1, GAPDH or the plant promoters CaMV/35S, SSU, OCS, lib4, usp, STLS1, B33, not or the ubiquitin or phaseolin promoter. The use of inducible promoters is particularly preferred, such as, for example, light- and, in particular, temperature-inducible promoters such as the $P_rP_l$ promoter. It is possible in principle for all natural promoters with their regulatory sequences to be used. In addition, it is also possible advantageously to use synthetic promoters.

Said regulatory sequences are intended to make specific expression of the nucleic acid sequences and protein expression possible. This may mean, for example, depending on the host organism, that the gene is expressed or overexpressed only after induction or that it is immediately expressed and/or overexpressed.

The regulatory sequences or factors may moreover preferably influence positively, and thus increase or reduce, expression. Thus, enhancement of the regulatory elements can take place advantageously at the level of transcription by using strong transcription signals such as promoters and/or enhancers. However, it is also possible to enhance translation by, for example, improving the stability of the mRNA.

An expression cassette is produced by fusing a suitable promoter to a suitable coding nucleotide sequence and to a terminator signal or polyadenylation signal. Conventional techniques of recombination and cloning are used for this purpose, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are well known to the skilled worker and can be found, for example, in "Cloning Vectors" (Pouwels P. H. et al., eds, Elsevier, Amsterdam-New York-Oxford, 1985). Vectors also mean not only plasmids but also all other vectors known to the skilled worker, such as, for example, phages, viruses, such as SV40, CMV, baculovirus and adenovirus, transposons, IS elements, phasmids, cosmids, and linear or circular DNA. These vectors may undergo autonomous replication in the host organism or chromosomal replication.

Examples of suitable expression vectors which may be mentioned are:

Conventional fusion expression vectors such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.), with which respectively glutathione S-transferase (GST), maltose E-binding protein and protein A are fused to the recombinant target protein.

Nonfusion protein expression vectors such as pTrc (Amann et al., (1988) Gene 69:301-315) and pET 11d (Studier et al. Gene Expression Technology: Methods in Enzymology 185, Academic Press, San Diego, Calif. (1990) 60-89).

Yeast expression vector for expression in the yeast S. cerevisiae, such as pYepSec1 (Baldari et al., (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods for constructing vectors suitable for use in other fungi such as filamentous fungi comprise those which are described in detail in: van den Hondel, C. A. M. J. J. & Punt, P. J. (1991) "Gene transfer systems and vector development for filamentous fungi, in: Applied Molecular Genetics of Fungi, J. F. Peberdy et al., eds, pp. 1-28, Cambridge University Press: Cambridge.

Baculovirus vectors which are available for expression of proteins in cultured insect cells (for example Sf9 cells) comprise the pAc series (Smith et al., (1983) Mol. Cell. Biol. 3:2156-2165) and pVL series (Lucklow and Summers (1989) Virology 170:31-39).

Plant expression vectors such as those described in detail in: Becker, D., Kemper, E., Schell, J. and Masterson, R. (1992) "New plant binary vectors with selectable markers located proximal to the left border", Plant Mol. Biol. 20:1195-1197; and Bevan, M. W. (1984) "Binary Agrobacterium vectors for plant transformation", Nucl. Acids Res. 12:8711-8721.

Mammalian expression vectors such as pCDM8 (Seed, B. (1987) Nature 329:840) and pMT2PC (Kaufman et al. (1987) EMBO J. 6:187-195).

Further suitable expression systems for prokaryotic and eukaryotic cells are described in chapters 16 and 17 of Sambrook, J., Fritsch, E. F. and Maniatis, T., Molecular cloning: A Laboratory Manual, 2nd edition, Cold Spring Harbor Laboratory, Cold Spring Harbor Laboratory Press, Cold Spring Harbor, N.Y., 1989.

4. Recombinant Host Organisms:

The vectors of the invention can be used to produce recombinant organisms which are transformed, for example, with at least one vector of the invention and can be employed for producing the polypeptides of the invention. The recombinant constructs of the invention described above are advantageously introduced and expressed in a suitable host system. Cloning and transfection methods familiar to the skilled worker, such as, for example, coprecipitation, protoplast fusion, electroporation, retroviral transfection and the like, are preferably used to bring about expression of said nucleic acids in the particular expression system. Suitable systems are described, for example, in Current Protocols in Molecular Biology, F. Ausubel et al., eds, Wiley Interscience, New York 1997, or Sambrook et al. Molecular Cloning: A Laboratory Manual, 2nd edition, Cold Spring Harbor Laboratory, Cold Spring Harbor Laboratory Press, Cold Spring Harbor, N.Y., 1989.

Suitable host organisms are in principle all organisms which enable expression of the nucleic acids of the invention, their allelic variants, their functional equivalents or derivatives. Host organisms mean, for example, bacteria, fungi, yeasts, plant or animal cells. Preferred organisms are bacteria, such as those of the genera Escherichia, such as, for example, Escherichia coli, Streptomyces, Bacillus or Pseudomonas, eukaryotic microorganisms such as Saccharomyces cerevisiae, Aspergillus, higher eukaryotic cells from animals or plants, for example Sf9 or CHO cells.

Successfully transformed organisms can be selected through marker genes which are likewise present in the vector or in the expression cassette. Examples of such marker genes are genes for antibiotic resistance and for enzymes which catalyze a color-forming reaction which causes staining of the transformed cell. These can then be selected by automatic cell sorting. Microorganisms which have been successfully transformed with a vector and harbor an appropriate antibiotic resistance gene (for example G418 or hygromycin) can be selected by appropriate antibiotic-containing media or nutrient media. Marker proteins present on the surface of the cell can be used for selection by means of affinity chromatography.

If desired, the gene product can also be expressed in transgenic organisms such as transgenic animals such as, in particular, mice, sheep or transgenic plants.

The invention further relates to methods for the recombinant production of AGER-RME or AGER-CDP peptides of the invention or functional, biologically active fragments thereof, wherein a peptide-producing recombinant host organism is cultured, expression of the polypeptides is induced if appropriate, and they are isolated from the culture. The peptides can also be produced on the industrial scale in this way if desired.

The recombinant host can be cultured and fermented by known methods. Bacteria can be grown, for example, in TB or LB medium and at a temperature of 20 to 40° C. and a pH of from 6 to 9. Details of suitable culturing conditions are described, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation methods. The cells may alternatively be disrupted by high-frequency ultrasound, by high pressure, such as, for example, in a French pressure cell, by osmolysis, by the action of detergents, lytic enzymes or organic solvents, by homogenizers or by a combination of a plurality of the methods mentioned.

The peptides can be purified by known chromatographic methods such as molecular sieve chromatography (gel filtration), such as Q-Sepharose chromatography, ion exchange chromatography and hydrophobic chromatography, and by other usual methods such as ultrafiltration, crystallization, salting out, dialysis and native gel electrophoresis. Suitable methods are described, for example, in Cooper, F. G., Biochemische Arbeitsmethoden, Verlag Walter de Gruyter, Berlin, New York or in Scopes, R., Protein Purification, Springer Verlag, New York, Heidelberg, Berlin.

It is particularly advantageous for isolation of the recombinant peptide to use vector systems or oligonucleotides which extend the cDNA by particular nucleotide sequences and thus code for modified polypeptides or fusion proteins which serve, for example, for simpler purification. Suitable modifications of this type are, for example, so-called tags which act as anchors, such as, for example, the modification known as hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors can be used to attach the peptides to a solid support, such as, for example, a polymer matrix, which can, for example, be packed into a chromatography column, or can be used on a microtiter plate or another support.

These anchors can at the same time also be used for recognition of the peptides. It is also possible to use for recognition of the peptides conventional markers such as fluorescent dyes, enzyme markers which form a detectable reaction product after reaction with a substrate, or radioactive labels, alone or in combination with the anchors for derivatizing the peptides.

5. Immunoglobulins

5.1 Definition

The present invention relates to monoclonal or polyclonal antibodies which bind specifically to an AGER-RME or AGER-CDP of the invention or derivative/equivalent thereof, i.e. antibodies having specificity for an AGER-RME of the invention or derivative/equivalent thereof. The present invention also relates to parts of these antibodies, especially antigen-binding parts thereof, i.e. antibody fragments which bind an AGER-RME or AGER-CDP of the invention or a derivative/equivalent thereof.

A "derivative/equivalent" of AGER-RME or AGER-CDP means in this connection also precursors such as AGER or sRAGE or other AGER splice variants in various conformational states which are induced transiently or permanently for example by interaction of these molecules with a corresponding binding partner.

The antibody of the invention is preferably chosen so that it has particular binding kinetics (e.g. high affinity, little dissociation, low off rate, strong neutralizing activity) for the specific binding to AGER-RME of the invention or derivate/equivalent thereof.

Thus, antibodies with an affinity for the AGER-RME or AGER-CDP of the invention or derivative/equivalent thereof in the region of $K_D=10^{-6}$-$10^{-12}$ M can be provided.

According to a further aspect, the antibodies of the invention can be chosen so that they bind the AGER-RME or AGER-CDP or derivative/equivalent thereof with a $k_{off}$ rate constant of 0.1 s$^{-1}$ or less.

The antibodies are preferably isolated antibodies. According to a further aspect, the antibodies are neutralizing antibodies. The antibodies of the invention include in particular monoclonal and recombinant antibodies. The antibodies of the invention may comprise an amino acid sequence which derives completely from a single species, and thus may be for example a human antibody or a mouse antibody. According to further embodiments, the antibody may be a chimeric antibody or a CDR graft antibody or another type of humanized antibody.

The term "antibody" is intended to refer to immunoglobulin molecules which are formed of 4 polypeptide chains, two heavy (H) chains and two light (L) chains. The chains are usually linked together by disulfide bonds. Every heavy chain is composed of a variable region of the heavy chain (abbreviated here to HCVR or VH) and a constant region of the heavy chain. The constant region of the heavy chain is formed from three domains CH1, CH2 and CH3. Each light chain is composed of a variable region of the light chain (abbreviated here to LCVR or VL) and a constant region of the light chain. The constant region of the light chain is formed from a CL domain. The VH and VL regions may be further divided into hypervariable regions which are referred to as complementarity-determining regions (CDR) and are interspersed with more conserved regions which are referred to as framework regions (FR). Each VH and VL region is formed from three CDRs and four FRs which are arranged from the N terminus to the C terminus in the following sequence: FR1, CDR1, FR2, CDR2, FR3, CDR3, FR4.

The term "antigen-binding part" of an antibody (or simply "antibody part") refers to one or more fragments of an antibody having specificity for an AGER-RME or AGER-CDP of the invention or derivative/equivalent thereof, the fragment(s) still having the ability to bind specifically the AGER-RME or AGER-CDP or derivative/equivalent thereof. It has been shown that the antigen-binding function of an antibody can be undertaken by fragments of a complete antibody. Examples of binding fragments include within the meaning of the term "antigen-binding part" of an antibody (i) an Fab fragment, i.e. a monovalent fragment composed of the VL, VH, CL and CH1 domains; (ii) an F(ab)$_2$ fragment, i.e. a bivalent fragment which comprises two Fab fragments linked together by a disulfide bridge in the hinge region; (iii) an Fd fragment which is composed of the VH and CH1 domains; (iv) an Fv fragment which is composed of the VL and VH domains of a single arm of an antibody; (v) a dAb fragment (Ward et al., (1989) *Nature* 341:544-546) which consists of a VH domain or VH, CH1, CH2, DH3, or VH, CH2, CH3; and (vi) an isolated complementarity-determining region (CDR). Although the two domains of the Fv fragment, namely VL and VH, are encoded by separate genes they can furthermore be connected together by a synthetic linker by use of recombinant methods, whereby they can be produced as a single protein chain in which the VL and VH regions are present together in order to form monovalent molecules (known as single-chain Fv (ScFv), see, for example, Bird at al. (1988) *Science* 242:423-426; and Huston et al. (1988) *Proc. Natl. Acad. Sci. USA* 85:5879-5883). Such single-chain antibodies are also intended to be encompassed by the term "antigen-binding part" of an antibody. Other types of single-chain antibodies such as diabodies likewise belong thereto. Diabodies are bivalent, bispecific antibodies in which VH and VL domains are expressed on a single polypeptide chain, but with use of a linker which is too short for the two domains to be present together on the same chain, the domains thus being forced to pair with complementary domains of another chain and to form two antigen-binding sites (see, for example, Holliger, P., et al. (1993) *Proc. Natl. Acad. Sci. USA* 90:6444-6448; Poljak, R. J., et al. (1994) *Structure* 2:1121-1123).

A further possibility is for an antibody or antigen-binding part thereof to be part of a larger immunoadhesion molecule which is formed by covalent or non-covalent association of the antibody or antibody part with one or more further proteins or peptides. Such immunoadhesion molecules involve the use of the streptavidin core region in order to produce a tetrameric scFv molecule (Kipriyanov, S. M., et al. (1995) *Human Antibodies and Hybridomas* 6:93-101) and the use of a cysteine residue, of a marker peptide and of a C-terminal polyhistidine tag in order to make bivalent and biotinylated scFv molecules (Kipriyanov, S. M., et al. (1994) *Mol. Immunol.* 31:1047-1058).

Antibody parts, such as Fab and F(ab')$_2$ fragments, can be produced from whole antibodies by using conventional techniques such as digestion with papain or pepsin. It is additionally possible to obtain antibodies, antibody parts and immunoadhesion molecules by using standardized recombinant DNA techniques. An "isolated antibody having specificity for an AGER-RME or AGER-CDP of the invention or derivative/equivalent thereof" describes an antibody which has specificity for an AGER-RME or AGER-CDP of the invention or derivative/equivalent thereof and which is substantially free of other antibodies having different antigen specificities.

The term "neutralizing antibody" describes an antibody whose binding to a particular antigen leads to inhibition of the biological activity of the antigen. This inhibition of the biological activity of the antigen can be assessed by measuring one or more indicators of the biological activity of the antigen, using a suitable in vitro or in vivo assay.

The term "monoclonal antibody" describes an antibody which is derived from a hybridoma (e.g. an antibody which is secreted by a hybridoma produced by means of hybridoma technology such as the standardized hybridoma methods of Miller and Milstein). An antibody derived from a hybridoma and having specificity for an AGER-RME or AGER-CDP of the invention or derivative/equivalent thereof is therefore referred to as a monoclonal antibody.

The term "recombinant antibody" describes antibodies which are produced, expressed, generated or isolated by recombinant means, such as antibodies which are expressed by use of a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al. (1992) *Nucl. Acids Res.* 20:6287-6295); or antibodies which are produced, expressed, generated or isolated in any other way in which particular immunglobulin gene sequences (such as human immunoglobulin gene sequences) are combined with other DNA sequences. Recombinant antibodies include, for example, chimeric, CDR graft and humanized antibodies.

The term "human antibody" describes antibodies whose variable and constant regions correspond to immunoglobulin sequences of the human germline, as described for example by Kabat et al. (see Kabat, et al. (1991) *Sequences of Proteins of Immunological Interest*, Fifth Edition, U.S. Department of Health and Human Services, NIH Publication No. 91-3242), or are derived therefrom. The human antibodies of the invention may, however, comprise amino acid residues which are not encoded by human germline immunglobulin sequences (e.g. mutations introduced by random or site-specific mutagenesis in vitro or by somatic mutation in vivo), for example in the CDRs, and especially in CDR3. Recombinant human antibodies of the invention have variable regions and may also comprise constant regions derived from immunoglobulin sequences of the human germline (see Kabat, E. A., et al. (1991) *Sequences of Proteins of Immunological Interest*, Fifth Edition, U.S. Department of Health and Human Services, NIH Publication No. 91-3242). According to particular embodiments, such recombinant human antibodies are, however, subjected to an in vitro mutagenesis (or to a somatic in vivo mutagenesis if an animal which is transgenic due to human Ig sequences is used), so that the amino acid sequences of the VH and VL regions of the recombinant antibodies are sequences which, although they are related to VH and VL sequences of the human germline or are derived therefrom, do not naturally exist within the human antibody germline repertoire in vivo. According to particular embodiments, such recombinant antibodies are the result of a selective mutagenesis or back-mutation, or both.

The term "back-mutation" refers to a method in which some or all of the somatically mutated amino acids of a human antibody are replaced by the corresponding germline residues of a homologous germline antibody sequence. The sequences of the heavy and light chain of a human antibody of the invention are separately compared with the germline sequences in the VBASE database in order to identify the sequences with the greatest homology. Deviations in the human antibody of the invention are returned to the germline sequence by mutation at defined nucleotide positions which encode such deviant amino acids. The direct or indirect significance of each amino acid, identified in this way as candidate for back-mutation, for antigen binding was to be investigated, and an amino acid which, after mutation, impairs a desirable property of the human antibody was not to be included in the eventual human antibody. In order to minimize the number of amino acids for a back-mutation, it is possible to leave unchanged those amino acid positions which, although deviating from the closest germline sequence, are identical to the corresponding amino acid sequence of a second germline sequence, provided that the second germline sequence is identical and colinear with the sequence of the human antibody of the invention in at least 10 and preferably in 12 amino acids on both sides of the amino acid in question. Back-mutations can be undertaken at any stage in antibody optimization.

The term "chimeric antibody" comprises antibodies in which individual parts of the molecule are derived from different species. Thus, chimeric antibodies are, without being restricted thereto, for example antibodies which comprise sequences for the variable region of the heavy and light chain from one species, but in which the sequences of one or more of the CDR regions from VH and/or VL are replaced by CDR sequences of another species. The variable regions in such antibodies may have mouse heavy and light chains in which one or more of the mouse CDRs (e.g. CDR3) are replaced by human CDR sequences.

The term "humanized antibody" describes antibodies which comprise sequences of the variable region of heavy and light chain from a non-human species (e.g. mouse, rat, rabbit, chicken, camelid, goat), but in which at least one part of the VH and/or VL sequence has been modified in order to be "more human-like", i.e. be like variable sequences of the human germline. One type of humanized antibody is a CDR graft antibody in which human CDR sequences are inserted into non-human VH and VL sequences in order to replace the corresponding non-human CDR sequences.

A method for measuring the binding kinetics of an antibody is based on so-called surface plasmon resonance. The term "surface plasmon resonance" refers to an optical phenomenon with which it is possible to analyze biospecific interactions by detecting changes in protein concentrations with a biosensor matrix, using for example the BIAcore system (Pharmacia Biosensor AB, Uppsala, Sweden and Piscataway, N.J.). For further descriptions, see Jönsson, U. et al. (1993) *Ann. Biol. Clin.* 51:19-26; Jönsson, U. et al., (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$" describes the off rate constant for dissociation of an antibody from the antibody/antigen complex.

The term "$K_d$" describes the dissociation constant of a particular antibody-antigen interaction.

The binding affinity of the antibodies of the invention can be assessed by using standardized in vitro immunoassays such as ELISA or BIAcore analyses.

5.2 Production of immunoglobulins 5.2.1 Production of Polyclonal Antibodies

The present invention relates to polyclonal anti-AGER-RME or anti-AGER-CDP antibodies and the production thereof.

For this purpose, a host is immunized with at least one AGER-RME or AGER-CDP of the invention or derivative/ equivalent thereof; and an antibody-containing serum of the host which is formed in response to the immunization is obtained.

If the AGER-RMEs or AGER-CDPs to be used have only weak or no immunogenicity, their immunogenicity can be increased by coupling them to carriers, preferably a carrier protein such as keyhole limpet hemocyanin (KLH), Limulus Polyphenus hemocyanin ((LPH), bovine serum albumin (BSA) or ovalbumin (OVA). A number of coupling possibilities are available to the skilled worker and are generally known. An expedient possibility is, for example, reaction with glutaraldehyde, for example by incubation of AGER-RMEs or AGER-CDPs with a suitable peptide or peptide mixture in water or an aqueous solvent. This reaction can conveniently be carried out at ambient temperature, usually meaning room temperature. However, cooling or gentle heating may also be expedient. The reaction usually leads to the desired result within a few hours, and a reaction time of, for example, 2 h is in the normal range. The glutaraldehyde concentration is usually in the ppm to % range, expediently from 10 ppm to 1%, preferably from 100 ppm to 0.5%. Optimization of the reaction parameters is within the scope of the skilled worker.

In addition to the antigen, the compositions ordinarily comprise further excipients, especially adjuvants normally employed for immunization, e.g. Freund's adjuvant. In particular, complete Freund's adjuvant is used for the first immunization, whereas all further immunizations are carried out with incomplete Freund's adjuvant. The immunizing cocktail is produced by adding the antigen (immunogen), preferably as component mixture described above, to the excipient(s). The antigen is usually emulsified in this case.

Suitable as host are in particular rodents or else rabbits. These or other suitable hosts are injected with the immunizing cocktail, preferably subcutaneously. The antibody titers can be determined using an immunoassay, for example competitively using a sheep antiserum directed against host IgG, and labeled AGER-RME or AGER-CDP. It is thus possible to decide towards the end of the immunization whether a particular host is suitable for obtaining antibodies. If, for example, four immunizations are carried out, the antibody titer can be determined after the third immunization, and then antibodies can be obtained from animals showing a sufficient antibody titer.

Blood is preferably taken from the hosts over several weeks or months in order to obtain the antibodies formed. It is possible finally to exsanguinate the host. Serum which comprises the desired antibodies can be obtained in a manner known per se from the blood obtained in this way. The whole serum obtained in this way can if necessary be further purified in a manner known to the skilled worker, in order to concentrate the antibody fraction present therein and, in particular, the AGER-RME- or AGER-CDP-recognizing antibodies.

In a particular embodiment of this method, at least one antibody of the serum which specifically recognizes the AGER-RME, AGER-CDP or a derivative/equivalent thereof used as immunogen is selected. Specificity means in this connection a higher binding affinity of the antibody for the immunogen than for other, in particular immunogenically related proteins, such as APP (amyloid precursor protein).

5.2.2 Production of Monoclonal Antibodies

Immunoglobulins useful according to the invention can be obtained using methods known per se. Thus, hybridoma technology allows monospecific antibodies for an antigen of interest to be produced. In addition, recombinant antibody techniques, such as the in vitro screening of antibody libraries, have been developed and can likewise be used to produce such specific antibodies.

Thus, for example, an animal can be immunized with the antigen of interest. This in vivo approach may further comprise establishing a series of hybridomas from the lymphocytes or spleen cells of an animal, and selecting a hybridoma which secretes an antibody which specifically binds the antigen. The animal to be immunized may be for example a mouse, rat, rabbit, chicken, camelid or sheep, or a transgenic version of one of the aforementioned animals, for example a transgenic mouse with human immunoglobulin genes which makes human antibodies after an antigen stimulus. Further types of animals which can be immunized include mice with severe combined immunodeficiency (SCID) which have been reconstituted with human peripheral mononuclear blood cells (chimeric hu-PBMC-SCID mice) or with lymphoid cells or precursors thereof, as well as mice which have been treated with lethal whole-body irradiation, subsequently protected from radiation with bone-marrow cells from a mouse with severe combined immunodeficiency (SCID) and subsequently transplanted with functional human lymphocytes (the so-called trimera system). A further type of animal to be immunized is an animal (e.g. a mouse) in whose genome an endogenous gene which encodes the antigen of interest has been switched off ("knocked out"), e.g. by homologous recombination, so that this animal recognizes the antigen as foreign after immunization with the antigen. It is clear to the skilled worker that the polyclonal or monoclonal antibodies produced by these methods are characterized and selected by using known screening methods, which include ELISA techniques, but without being restricted thereto.

According to a further embodiment, a recombinant antibody library is screened with the antigen. The recombinant antibody library can be expressed for example on the surface of bacteriophages or on the surface of yeast cells or on the surface of bacterial cells. The recombinant antibody library can be for example an scFv library or an Fab library. In a further embodiment, antibody libraries can be expressed as RNA-protein fusions.

A further approach to the production of antibodies of the invention comprises a combination of in vivo and in vitro approaches. For example, the antigen can be allowed to act on the antibody repertoire by immunizing an animal with the antigen in vivo and subsequently using the antigen for in vitro screening of a recombinant antibody library produced from lymphoid cells of the animal, or a single-domain antibody library (e.g. with heavy and/or light chains). According to a further approach, the antigen is allowed to act on the antibody repertoire by immunizing an animal with the antigen in vivo and subsequently subjecting a recombinant antibody library produced from lymphoid cells of the animal or a single-domain library to an affinity maturation. According to a further approach, the antigen is allowed to act on the antibody repertoire by immunizing an animal with the antigen in vivo, subsequently selecting single antibody-producing cells which secrete an antibody of interest, and obtaining from these selected cells cDNAs for the variable region of the heavy and light chain (e.g. by PCR) and expressing the variable regions of the heavy and light chain in vitro in mammalian host cells (which is referred to as the lymphocyte-antibody selection method or SLAM for selected lymphocyte antibody method), allowing the selected antibody gene sequences to be selected and manipulated further. Monoclonal antibodies can additionally be selected by expression cloning by expressing the antibody genes for the heavy and light chain in mammalian cells, and selecting the mammalian cells which secrete an antibody having the desired binding affinity.

The present invention makes defined antigens available in the form of AGER-RMEs or AGER-CDPs for screening and counterscreening. It is thus possible according to the invention to select those polyclonal and monoclonal antibodies which show a profile of properties which is desired according to the invention as defined above, such as, for example, to specifically recognize an AGER-induced receptor status.

The method of the invention for producing antibodies can be used to produce various types of antibodies. These include substantially human antibodies, chimeric antibodies, humanized antibodies and CDR graft antibodies, and antigen-binding parts thereof.

Methods for producing antibodies of the invention are described below. A distinction is made in this connection between in vivo approaches, in vitro approaches or a combination of the two.

In Vivo Approaches:

Starting from cells which produce the antibody generated in vivo it is possible to produce monoclonal antibodies by standardized techniques, such as the hybridoma technique originally described by Köhler and Milstein (1975, *Nature* 256:495-497) (see also Brown et al. (1981) *J. Immunol.* 127: 539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is sufficiently well known (see in general R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). An immortalized cell line (typically a myeloma) is for this purpose fused to lymphocytes (typically splenocytes or lymph node cells or peripheral blood lymphocytes) of a mammal immunized with the AGER-RME or AGER-CDP of the invention or derivative/equivalent thereof, and the culture supernatants of the resulting hybridoma cells are screened in order to identify a hybridoma which produces a monoclonal antibody having specificity for AGER-RME or AGER-CDP of the invention or for a derivative/equivalent thereof. It is possible to use for this purpose any of the many sufficiently well known protocols for fusing lymphocytes and immortalized cell lines (see also G. Galfre et al. (1977) *Nature* 266:550-52; Gefter et al. *Somatic Cell Genet.*, cited supra; Lerner, *Yale J. Biol. Med.*, cited supra; Kenneth, Monoclonal Antibodies, cited supra). The skilled worker is additionally aware of many different variations of such methods, which can likewise be used. Typically, the immortalized cell lines (e.g. a myeloma cell line) were derived from the same mammalian species as the lymphocytes. It is possible for example to establish murine hybridomas by fusing lymphocytes from a mouse immunized with an immunogenic preparation of the invention with an immortalized mouse cell line. Preferred immortalized cell lines are mouse myeloma cell lines which are sensitive to culture medium comprising hypoxanthine, aminopterin and thymidine (HAT medium). Any one of many myeloma cell lines can be used in standard fashion as fusion partner, e.g. the P3-NS1/1-Ag4-1, P3-X63-Ag8.653 or Sp2/O-Ag14 myeloma line. These myeloma cell lines are obtainable from the American Type Culture Collection (ATCC), Rockville, Md. Typically, HAT-sensitive mouse myeloma cells are fused to mouse splenocytes using polyethylene glycol (PEG). The hybridoma cells resulting from the fusion are then selected using HAT medium whereby non-fused and non-productively fused myeloma cells are killed (non-fused splenocytes die after several days because they are not transformed). Monoclonal antibody-producing hybridoma cells which specifically recognize an AGER-RME or AGER-CDP of the invention or a derivative/equivalent thereof are identified by screening the hybridoma culture supernants of such antibodies e.g. by using a standard ELISA assay in order to select those antibodies which are able to bind specifically the AGER-RME or AGER-CDP of the invention or a derivative/equivalent thereof.

Depending on the nature of the desired antibody, various host animals can be used for the in vivo immunization. A host which itself expresses an endogenous version of the antigen of interest can be used. Alternatively, a host which has been made deficient for an endogenous version of the antigen of interest can be used. It has been shown for example that mice which have been made deficient of a particular endogenous protein by homologous recombination on the corresponding endogenous gene (i.e. knockout mice) generate a humoral response to the protein with which they have been immunized and can therefore be used to produce high-affinity monoclonal antibodies against the protein (see, for example, Roes, J. et al. (1995) *J. Immunol. Methods* 183:231-237; Lunn, M. P. et al. (2000) *J. Neurochem.* 75:404-412).

Many non-human mammals are suitable as hosts for antibody production for producing non-human antibodies against AGER-RME or AGER-CDP of the invention or a derivative/equivalent thereof. These include mice, rats, chickens, camelids, rabbits and goats (and knockout versions thereof), although mice are preferred for hybridoma production. It is further possible to use a non-human host animal which expresses a human antibody repertoire for producing substantially human antibodies against a human antigen having dual specificity. Such non-human animals include transgenic animals (e.g. mice) which harbor human immunglobulin transgenes (chimeric hu-PBMC-SCID mice) and human/mouse radiation chimeras, which are described in detail below.

According to one embodiment, the animal which is immunized with an AGER-RME or AGER-CDP of the invention or derivative/equivalent thereof is a non-human mammal, preferably a mouse which is transgenic owing to human immunoglobulin genes, so that the non-human mammal makes human antibodies after an antigenic stimulus. Typically, immunoglobulin transgenes for heavy and light chain with human germline configuration are introduced into such animals, the animals having been modified so that their endogenous loci for heavy and light chain are inactive. Stimulation of such animals with antigen (e.g. with a human antigen) leads to production of antibodies which are derived from the human immunglobulin sequences (i.e. human antibodies). Human monoclonal antibodies can be made from the lymphocytes of such animals by means of standardized hypridoma technology. For further description of transgenic mice with human immunoglobulins and their use in the production of human antibodies, see, for example, U.S. Pat. No. 5,939, 598, WO 96/33735, WO 96/34096, WO 98/24893 and WO 99/53049 (Abgenix Inc.), and U.S. Pat. No. 5,545,806, No. 5,569,825, No. 5,625,126, No. 5,633,425, No. 5,661,016, No. 5,770,429, No. 5,814,318, No. 5,877,397 and WO 99/45962 (Genpharm Inc.); see likewise MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N. (1995) *Ann. N.Y. Acad. Sci.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188:483-495; Green, L. L.

(1999) *J. Immunol. Methods* 231:11-23; Yang, X. D. et al. (1999) *J. Leukoc. Biol.* 66:401-410; Gallo, M. L. et al. (2000) *Eur. J. Immunol.* 30:534-540.

In a further embodiment, the animal which is immunized with AGER-RME or AGER-CDP of the invention or a derivative/equivalent thereof can be a mouse with severe combined immunodeficiency (SCID) which has been reconstituted with human peripheral mononuclear blood cells or lymphoid cells or precursors thereof. Such mice, which are referred to as chimeric hu-PBMC-SCID mice, have been demonstrated to produce human immunoglobulin responses after an antigenic stimulus. For further description of these mice and their use for generating antibodies, see, for example, Leader, K. A. et al. (1992) *Immunology* 76:229-234; Bombil, F. at al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. at al. (1997) *J. Immunol.* 159:1393-1403; Nguyen, H. et al. (1997) *Microbiol. Immunol.* 41:901-907; Arai, K. et al. (1998) *J. Immunol. Methods* 217:79-85; Yoshinari, K. and Arai, K. (1998) *Hybridoma* 17:41-45; Hutchins, W. A. et al. (1999) *Hybridoma* 18:121-129; Murphy, W. J. et al. (1999) *Clin. Immunol.* 90:22-27; Smithson, S. L. et al. (1999) *Mol. Immunol.* 36:113-124; Chamat, S. et al. (1999) *J. Infect. Diseases* 180:268-277; and Heard, C. et al. (1999) *Molec. Med.* 5:35-45.

In a further embodiment, the animal which is immunized with AGER-RME or AGER-CDP of the invention or a derivative/equivalent thereof is a mouse which has been treated with a lethal whole-body irradiation, subsequently protected against radiation with bone-marrow cells from mice with severe combined immunodeficiency (SCID), and subsequently transplanted with functional human lymphocytes. This type of chimera, referred to as the trimera system, is used to produce human monoclonal antibodies by immunizing the mice with the antigen of interest, and subsequently producing monoclonal antibodies using standardized hybridoma technology. For further description of these mice and their use for generating antibodies, see, for example, Eren, R. et al. (1998) *Immunology* 93:154-161; Reisner, Y. and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

In Vitro Approaches:

As alternative to the production of antibodies of the invention by immunization and selection, it is possible to identify and isolate antibodies of the invention by screening a recombinant combinatorial immunglobulin library with an AGER-RME or AGER-CDP of the invention or derivative/equivalent thereof in order thus to isolate members of the immunoglobulin library which bind specifically to the AGER-RME or AGER-CDP or derivative/equivalent thereof. Kits for generating and screening display libraries are commercially available (e.g. the Recombinant Phage Antibody System from Pharmacia, catalog No. 27-9400-01; and the SurfZAP® Phage Display Kit from Stratagene, catalog No. 240612). In many embodiments, the display library is an scFv library or an Fab library. The phage display technique for screening recombinant antibody libraries has been sufficiently well described. Examples of methods and compounds which can be used particularly advantageously in the generation and screening of antibody display libraries can be found for example in McCafferty et al. WO 92/01047, U.S. Pat. No. 5,969,108 and EP 589 877 (describes in particular the display of scFv), Ladner at al. U.S. Pat. No. 5,223,409, No. 5,403,484, No. 5,571,698, No. 5,837,500 and EP 436 597 (describes for example the pill fusion); Dower et al. WO 91/17271, U.S. Pat. No. 5,427,908, U.S. Pat. No. 5,580,717 and EP 527 839 (describes in particular the display of Fab); Winter et al. International Publication WO 92/20791 and EP 368,684 (describes in particular the cloning of sequences for variable immunoglobulin domains); Griffiths at al. U.S. Pat. No. 5,885,793 and EP 589 877 (describes in particular the isolation of human antibodies against human antigens using recombinant libraries); Garrard at al. WO 92/09690 (describes in particular phage expression techniques); Knappik et al. WO 97/08320 (describes the human recombinant antibody library HuCal); Salfeld et al. WO 97/29131 (describes the production of a recombinant human antibody against a human antigen (human tumor necrosis factor alpha), and in vitro affinity maturation of the recombinant antibody) and Salfeld et al. U.S. Provisional Application No. 60/126,603 and the patent applications based thereon (likewise describes the production of recombinant human antibodies against human antigen (human interleukin-12), and the in vitro affinity maturation of the recombinant antibody).

Further descriptions of screenings of recombinant antibody libraries are to be found in scientific publications such as Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; McCafferty et al. *Nature* (1990) 348:552-554; and Knappik et al. (2000) *J. Mol. Biol.* 296:57-86.

As an alternative to the use of bacteriophage display systems it is possible to express recombinant antibody libraries on the surface of yeast cells or bacterial cells. Methods for producing and screening libraries expressed on the surface of yeast cells are described in WO 99/36569. Methods for producing and screening libraries expressed on the surface of bacterial cells are described in detail in WO 98/49286.

As soon as an antibody of interest has been identified from a combinatorial library, the DNAs which encode the light and heavy chains of the antibody are isolated by standardized techniques of molecular biology, for example by PCR amplification of DNA from the display package (e.g. the phage) which has been isolated during the screening of the library. Nucleotide sequences of genes for light and heavy antibody chains which can be used to produce PCR primers are known to the skilled worker. Many such sequences are described for example in Kabat, E. A., et al. (1991) *Sequences of Proteins of Immunological Interest*, Fifth Edition, U.S. Department of Health and Human Services, NIH Publication No. 91-3242 and the database for sequences of the human germline VBASE.

An antibody or antibody part of the invention can be produced by recombinant expression of the genes for light and heavy immunglobulin chains in a host cell. For recombinant expression of an antibody, a host cell is transfected with one or more recombinant expression vectors which harbor DNA fragments which encode the light and heavy immunoglobulin chains of the antibody, so that the light and heavy chains are expressed in the host cell and preferably secreted into the medium in which the host cells are cultivated. The antibodies can be obtained from this medium. Standardized recombinant DNA methods are used to obtain genes for heavy and light antibody chains, to insert these genes into recombinant expression vectors and to introduce the vectors into host cells. Methods of this type are described for example in Sambrook, Fritsch and Maniatis (editors), *Molecular Cloning; A Laboratory Manual*, Second Edition, Cold Spring Harbor, N.Y., (1989), Ausubel, F. M. et al. (editors) *Current Protocols in Molecular Biology*, Greene Publishing Associates, (1989) and in U.S. Pat. No. 4,816,397 of Boss et al.

As soon as DNA fragments which encode the VH and VL segments of the antibody of interest have been obtained, these DNA fragments can be further manipulated using standardized recombinant DNA techniques, for example in order to convert the genes for variable regions into genes for full-length antibody chains, into genes for Fab fragments or into an scFv gene. These manipulatins lead to operative linkage of a VL- or VH-encoding DNA fragment to a further DNA fragment which encodes a further protein, e.g. a constant antibody region or a flexible linker. The term "operative linkage" is intended here to mean that the two DNA fragments are connected together in such a way that the amino acid sequences encoded by the two DNA fragments remain in the reading frame (in-frame).

The isolated DNA encoding the VH region can be converted into a gene for a full-length heavy chain for operative linkage of the DNA encoding the VH region to a further DNA molecule encoding constant regions of the heavy chain (CH1, CH2 and CH3). The sequences of genes for constant regions of human heavy chains are sufficiently well known (see, for example, Kabat, E. A., et al. (1991) *Sequences of Proteins of Immunological Interest*, Fifth Edition, U.S. Department of Health and Human Services, NIH Publication No. 91-3242), and DNA fragments which span these regions can be obtained by standardized PCR amplification. The constant region of the heavy chain may be a constant region from IgG1, IgG2, IgG3, IgG4, IgA, IgE, IgM or IgD, with preference for a constant region from IgG1 or IgG4. A gene for an Fab fragment of the heavy chain can be obtained by operative linkage of the VH-encoding DNA with a further DNA molecule which encodes only the constant region CH1 of the heavy chain.

The isolated DNA encoding the VL region can be converted into a gene for a full-length light chain (and a gene for an Fab light chain) by operative linkage of the VL-encoding DNA with a further DNA molecule which encodes the constant region CL of the light chain. The sequences of genes of the constant region of human light chains are sufficiently well known (see Kabat, E. A., et al. (1991) *Sequences of Proteins of Immunological Interest*, Fifth Edition, U.S. Department of Health and Human Services, NIH Publication No. 91-3242), and DNA fragments which span these regions can be obtained by standardized PCR amplification. The constant region of the light chain may be a constant kappa or lambda region, with preference for a constant kappa region.

An scFv gene can be generated by operative linkage of the VH- and VL-encoding DNA fragments to a further fragment encoding a flexible linker, e.g. the amino acid sequence $(Gly_4-Ser)_3$, so that the VH and VL sequences are expressed as continuous single-chain protein, with the VL and VH regions being connected together by the flexible linker (see Bird et al. (1988) *Science* 242:423-426; Huston et al. (1988) *Proc. Natl. Acad. Sci. USA* 85:5879-5883; McCafferty et al., *Nature* (1990) 348:552-554).

VH and VL single domains with specificity for AGER-RME or AGER-CDP of the invention or a derivative/equivalent thereof can be isolated from single-domain libraries using the methods described above. Two VH single-domain chains (with or without CH1) or two VL chains or a pair of a VH chain and a VL chain having the desired specificity can be used to bind AGER-RMEs or AGER-CDPs of the invention or derivatives/equivalents thereof.

The recombinant antibodies or antibody parts of the invention can be expressed by inserting the DNAs which encode the partial or full-length light and heavy chains into expression vectors to result in operative linkage of the genes to transcriptional and translational control sequences. The term "operative linkage" in this connection is intended to mean that an antibody gene is ligated in a vector in such a way that transcriptional and translational control sequences within the vector fulfil their intended function of regulating the transcription and translation of the antibody gene.

The expression vector and the expression control sequences are chosen so that they are compatible with the host cell used for expression. The gene for the light antibody chain and the gene for the heavy antibody chain can be inserted into separate vectors, or both genes are inserted into the same expression vector, which is usually the case. The antibody genes are inserted into the expression vector by standardized methods (e.g. ligation of complementary restriction cleavage sites on the antibody gene fragment and vector, or ligation of blunt ends, if no restriction cleavage sites are present). The expression vector may already harbor sequences for constant antibody regions before the insertion of the sequences for the light and heavy chain. One approach for example is to convert the VH and VL sequences into full-length antibody genes by inserting them into expression vectors which already encode constant regions of heavy and light chains respectively, so that there is operative linkage of the VH segment to the CH segment(s) within the vector, and also operative linkage of the VL segment to the CL segment within the vector. An additional or alternative possibility is for the recombinant expression vector to encode a signal peptide which facilitates secretion of the antibody chain from the host cell. The gene for the antibody chain can be cloned into the vector in such a way that the signal peptide is linked in reading frame with the N terminus of the gene for the antibody chain. The signal peptide may be an immunoglobulin signal peptide or a heterologous signal peptide (i.e. a signal peptide from a non-immunoglobulin protein). In addition to the genes for the antibody chain, the expression vectors of the invention may have regulatory sequences which control expression of the genes for the antibody chain in a host cell. The term "regulatory sequence" is intended to include promoters, enhancers and further expression control elements (e.g. polyadenylation signals) which control the transcription or translation of the genes for the antibody chain. Such regulatory sequences are described for example in Goeddel; *Gene Expression Technology: Methods in Enzymology* 185, Academic Press, San Diego, Calif. (1990). The skilled worker is aware that the design of the expression vector, which includes the selection of regulatory sequences, may depend on factors such as the choice of the host cell to be transformed, the desired strength of protein expression etc. Preferred regulatory sequences for expression in mammalian host cells include viral elements which lead to strong protein expression in mammalian cells, such as promoters and/or enhancers, which are derived from cytomegalovirus (CMV) (such as the CMV promoter/enhancer), simian virus 40 (SV40) (such as the SV40 promoter/enhancer), adenovirus (e.g. the late adenovirus major promoter (AdMLP for Adenovirus Major Late Promoter) and polyoma. For further description of viral regulatory elements and sequences thereof, see, for example, U.S. Pat. No. 5,168,062 of Stinski, U.S. Pat. No. 4,510,245 of Bell et al. and U.S. Pat. No. 4,968,615 of Schaffner et al.

In addition to the genes for the antibody chain and the regulatory sequences, the recombinant expression vectors of the invention may have additional sequences such as sequences which regulate the replication of the vector in host cells (e.g. origins of replication) and selectable marker genes. The selectable marker genes facilitate the selection of host cells in which the vector has been introduced (see, for example, U.S. Pat. Nos. 4,399,216, 4,634,665 and 5,179,017, all of Axel et al.). For example, it is usual for the selectable marker gene to make a host cell into which the vector has been inserted resistant to active substances such as G418, hygromycin or methotrexate. Preferred selectable marker genes include the gene for dihydrofolate reductase (DHFR) (for use in dhfr⁻ host cells with methotrexate selection/amplification) and the neogene (for G418 selection).

For expression of the light and heavy chains, the expression vector(s) encoding the heavy and light chains is or are transfected into a host cell using standardized techniques. The various forms of the term "transfection" are intended to encompass a large number of techniques which are normally used to introduce exogenous DNA into a prokaryotic or eukaryotic host cell, e.g. electroporation, calcium phosphate precipitation, DEAE-dextran transfection and the like. Although it is theoretically possible to express the antibodies of the invention either in prokaryotic or eukaryotic host cells, expression of the antibodies in eukaryotic cells and in particular in mammalian host cells is preferred, because the probability that a correctly folded and immunologically active antibody is assembled and secreted is higher in such eukaryotic cells and especially mammalian cells than in prokaryotic cells. It has been reported that prokaryotic expression of antibody genes is inefficient for the production of large yields of active antibody (Boss, M. A. and Wood, C. R. (1985) *Immunology Today* 6:12-13).

Mammalian host cells preferred for the expression of recombinant antibodies of the invention include CHO cells (including dhfr CHO cells, which are described in Urlaub and Chasin, (1980) *Proc. Natl. Acad. Sci. USA* 77:4216-4220, and are used with a DHFR selectable marker as described for example in R. J. Kaufman and P. A. Sharp (1982) *Mol. Biol.* 159:601-621), NSO myeloma cells, COS cells and SP2 cells. If recombinant expression vectors which encode the antibody genes are introduced into mammalian host cells, the antibodies are produced by cultivating the host cells until the antibody is expressed in the host cells or, preferably, the antibody is secreted into the culture medium in which the host cells grow. The antibodies can be obtained from the culture medium by using standardized methods for purifying proteins.

It is likewise possible to use host cells to produce parts of intact antibodies, such as Fab fragments or scFv molecules. The invention of course includes variations of the procedure described above. For example, it may be desirable to transfect a host cell with DNA which encodes either the light chain or the heavy chain (but not both) of an antibody of the invention. If light or heavy chains which are unnecessary for the binding of the antigen of interest are present, the DNA which encodes either one such light or one such heavy chain or both is partly or completely deleted by means of recombinant DNA technology. Molecules expressed by such truncated DNA molecules likewise belong to the antibodies of the invention. It is additionally possible to produce bifunctional antibodies in which one heavy and one light chain are an antibody of the invention, and the other heavy and light chain have specificity for an antigen other than that of interest, by crosslinking an antibody of the invention with a second antibody by standardized chemical methods.

In a preferred system for recombinant expression of an antibody of the invention or antigen-binding part thereof, a recombinant expression vector which encodes both the heavy antibody chain and the light antibody chain is introduced by calcium phosphate-mediated transfection into dhfr CHO cells. There is operative linkage within the recombinant expression vector of the genes for the heavy and light antibody chain in each case to regulatory CMV enhancer/AdMLP promoter elements in order to bring about strong transcription of the genes. The recombinant expression vector also harbors a DHFR gene which can be used to select CHO cells transfected with the vector by using methotrexate selection/amplification. The selected transformed host cells are cultivated so that the heavy and light antibody chains are expressed, and intact antibody is obtained from the culture medium. Standardized techniques of molecular biology are used in order to produce the recombinant expression vector, to transfect the host cells, to select the transformants, to cultivate the host cells and to obtain the antibody from the culture medium. Thus, the invention relates to a method for synthesizing a recombinant antibody of the invention by cultivating a host cell of the invention in a suitable culture medium until a recombinant antibody of the invention is synthesized. The method may further comprise isolating the recombinant antibody from the culture medium.

As alternative to the screening of recombinant antibody libraries by phage display, it is possible to employ further methods known to the skilled worker for screening large combinatorial libraries in order to identify the antibodies of the invention. In one type of alternative expression system, the recombinant antibody library is expressed in the form of RNA-protein fusions as described in WO 98/31700 of Szostak and Roberts, and in Roberts, R. W. and Szostak, J. W. (1997) *Proc. Natl. Acad. Sci. USA* 94:12297-12302. In this system, a covalent fusion is generated by in vitro translation of synthetic mRNAs which carry at their 3' end puromycin, a peptidyl acceptor antibiotic, between an mRNA and the peptide or protein which it encodes. It is thus possible to enrich a specific mRNA from a complex mixture of mRNAs (e.g. a combinatorial library) on the basis of the properties of the encoded peptide or protein (e.g. of the antibody or a part thereof), such as binding of the antibody or part thereof to AGER-RME or AGER-CDP of the invention or a derivative/equivalent thereof. Nucleic acid sequences which encode antibodies or parts thereof and which are obtained from the screening of such libraries can be expressed by recombinant means in the manner described above (e.g. in mammalian host cells) and additionally be subjected to a further affinity maturation by either screening mRNA-peptide fusions in further rounds, in which case mutations are introduced into the original selected sequence(s), or by using other methods for in vitro affinity maturation of recombinant antibodies in the manner described above.

Combinations of In Vivo and In Vitro Approaches:

The antibodies of the invention can likewise be produced by applying a combination of in vivo and in vitro approaches, such as methods in which initially AGER-RME or AGER-CDP of the invention or a derivative/equivalent thereof is allowed to act on an antibody repertoire in vivo in a host animal in order to stimulate the production of AGER-RME- or AGER-CDP- or derivative/equivalent-binding antibodies, and subsequently further antibody selection and/or antibody maturation (i.e. optimization) is accomplished with the aid of one or more in vitro techniques. According to one embodiment, such a combined method may comprise initially immunizing a non-human animal (e.g. a mouse, rat, rabbit, chicken, camelids, goat or a transgenic version thereof or a chimeric mouse) with the AGER-RME or AGER-CDP of the invention or derivative/equivalent thereof in order to stimulate an antibody response against the antigen, and subsequently producing and screening a phage display antibody library using immunoglobulin sequences from lymphocytes which have been stimulated in vivo through the action of the AGER-RME or AGER-CDP or derivative/equivalent in vivo. The first step of this combined procedure can be carried out in the manner described above in connection with in vivo approaches, whereas the second step of this procedure can be carried out in the manner described above in connection with in vitro approaches. Preferred methods for the hyperimmunization of non-human animals with subsequent in vitro screening of phage display libraries produced from the stimulated lymphocytes include those described by BioSite Inc., see, for example WO 98/47343, WO 91/17271, U.S. Pat. No. 5,427, 908 and U.S. Pat. No. 5,580,717.

According to a further embodiment, a combined method comprises initially immunizing a non-human animal (e.g. a mouse, rat, rabbit, chicken, camelids, goat or a knockout and/or transgenic version thereof, or a chimeric mouse) with an AGER-RME or AGER-CDP of the invention or derivative/equivalent thereof in order to stimulate an antibody response against the AGER-RME or AGER-CDP or derivative/equivalent thereof, and selecting the lymphocytes which produce the antibodies having the desired specificity by screening hybridomas (produced for example from the immunized animals). The genes for the antibodies or single-domain antibodies are isolated from the selected clones (by standardized cloning methods such as reverse transcriptase-polymerase chain reaction) and subjected to an in vitro affinity maturation in order thus to improve the binding properties of the selected antibody or of the selected antibodies. The first step of this procedure can be completed in the manner described above in connection with the in vivo approaches, whereas the second step of this procedure can be completed in the manner described above in connection with the in vitro approaches, especially by using methods of in vitro affinity maturation such as those described in WO 97/29131 and WO 00/56772.

In a further combined method, the recombinant antibodies are generated from single isolated lymphocytes by using a procedure which is known to the skilled worker as lymphocyte antibody selection method (SLAM) and is described in U.S. Pat. No. 5,627,052, WO 92/02551 and Babcock, J. S. et al. (1996) *Proc. Natl. Acad. Sci. USA* 93:7843-7848. In this method, a non-human animal (e.g. a mouse, rat, rabbit, chicken, camelids, goat or a transgenic version thereof, or a chimeric mouse) is initially immunized in vivo with AGER-RME or AGER-CDP of the invention or a derivative/equivalent thereof in order to stimulate an immune response against the AGER-RME or AGER-CDP or derivative/equivalent, and then single cells secreting antibodies of interest are selected by using an antigen-specific hemolytic plaque assay. For this purpose, the AGER-RME or AGER-CDP or derivative/equivalent thereof, or structurally related molecules of interest, can be coupled to sheep erythrocytes, using a linker such as biotin, whereby individual cells which secrete antibodies of suitable specificity can be identified by using the hemolytic plaque assay. Following the identification of cells which secrete antibodies of interest, cDNAs for the variable regions of the light and heavy chains are obtained from the cells by reverse transcriptase-PCR, and these variable regions can then be expressed in conjunction with suitable constant immunoglobulin regions (e.g. human constant regions) in mammalian host cells such as COS or CHO cells. The host cells transfected with the amplified immunoglobulin sequences derived from lymphocytes selected in vivo can then be subjected to a further in vitro analysis and selection by, for example, expanding the transfected cells in order to isolate cells which express antibodies having the desired specificity. The amplified immunoglobulin sequences can moreover be manipulated in vitro.

6. Pharmaceutical Compositions 6.1 General

The present invention also relates to pharmaceutical compositions which comprise as active substance a protein of the invention (AGER-RME or AGER-CDP; AGER-RME- or AGER-CDP-binding ligands such as anti-AGER-RME or anti-AGER-CDP antibodies, bispecific antibodies, hybrid proteins as defined above; AGER ectodomains and N-terminal subfragments) or a coding AGER-RME nucleic acid sequence and, if appropriate, a pharmaceutically acceptable carrier. Pharmaceutical compositions of the invention may additionally comprise at least one additional therapeutic agent, e.g. one or more additional therapeutic agents for the treatment of one of the disorders described herein.

The pharmaceutically acceptable carriers include all solvents, dispersion media, coatings, antimicrobial agents, tonicity agents and agents delaying absorption, and the like, as long as they are physiologically compatible.

Pharmaceutically acceptable carriers include for example water, saline solution, phosphate-buffered saline solution, lactose, dextrose, sucrose, sorbitol, mannitol, starch, gum arabic, calcium phosphate, alginates, tragacanth, gelatin, calcium silicate, microcrystalline cellulose, polyvinylpyrrolidone, cellulose, water, syrup and methylcellulose. The formulations may additionally comprise pharmaceutically acceptable carriers or conventional excipients such as lubricants, for example tallow, magnesium stearate and mineral oil; wetting agents; emulsifying and suspending agents; preservatives such as methyl and propyl hydroxybenzoates; antioxidants; antiirritants; chelating agents; coating aids; emulsion stabilizers film formers; gel formers; odor-masking agents, masking flavors, resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilizers; suppository bases; tablet excipients such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik and angrenzende Gebiete, 4th edition, Aulendorf: ECV-Editio-Kantor-Verlag, 1996. Compare also Hager's Handbuch der Pharmazeutischen Praxis, Springer Verlag, Heidelberg.

The pharmaceutical compositions may be suitable for example for parenteral administration. For this purpose, the active substance such as, for example, the antibody is preferably prepared as injectable solutions with an active substance content of 0.1-250 mg/ml. The injectable solutions can be prepared in liquid or lyophilized form in a flintglass or vial, an ampoule or a filled syringe as dosage form.

The buffer may comprise L-histidine (1-50 mM, preferably 5-10 mM) and have a pH of 5.0-7.0, preferably of 6.0. Further suitable buffers include, without being restricted thereto, sodium succinate, sodium citrate, sodium phosphate or potassium phosphate buffers.

Sodium chloride can be used to adjust the tonicity of the solution to a concentration of 0-300 mM (preferably 150 mM for a liquid dosage form). Cryoprotectants can be included for a lyophilized dosage form, such as, for example, sucrose (e.g. 0-10%, preferably 0.5-1.0% (w/w)). Further suitable cryoprotectants include trehalose and lactose. Fillers can be included for a lyophilized dosage form e.g. mannitol (e.g. 1-10%, preferably 2-4% (w/w)). Stabilizers can be used both in liquid and lyophilized dosage forms, e.g. L-methionine (e.g. 51-50 mM, preferably 5-10 mM). Further suitable fillers include glycine and arginine. It is likewise possible to use surfactants, for example polysorbate 80 (e.g. 0-0.05%, preferably 0.005-0.01% (w/w)). Further surfactants include polysorbate 20 and BRIJ surfactants.

The compositions of the invention may assume a large number of forms. These include liquid, semisolid and solid dosage forms such as liquid solutions (e.g. injectable and infusible solutions, lotions, eye drops and ear drops), liposomes, dispersions or suspensions and solid forms such as oral powders, dusting powders, granules, tablets, pastilles, sachets, cachets, coated tablets, capsules such as hard and soft gelatin capsules, suppositories or vaginal pharmaceutical forms, semisolid pharmaceutical forms such as ointments, creams, hydrogels, pastes or patches. Implanted delivery devices can also be used to administer active substances of the invention. The preferred form depends on the intended mode of administration and therapeutic use. Typically, compositions in the form of injectable or infusible solutions are preferred. A suitable route of administration is, for example, parenteral (e.g. intravenous, subcutaneous, intraperitoneal, intramuscular). In a preferred embodiment, the active substance is administered by intravenous infusion or injection. According to a further preferred embodiment, the active substance is administered by intramuscular or subcutaneous injection.

Therapeutic compositions must typically be sterile and stable under the conditions of manufacture and storage. The compositions may be formulated as solution, microemulsion, dispersion, liposomal or a further ordered structure which is suitable for high active substance concentrations. Sterile injectable solutions can be produced by introducing the active compound (such as, for example, the antibody) in the required amount into a suitable solvent, if appropriate with one or a combination of the aforementioned ingredients, as required, and subsequently sterilizing by filtration. Dispersions are ordinarily prepared by introducing the active compound into a sterile vehicle which comprises a basic dispersion medium and, if appropriate, further required ingredients. In the case of a sterilized lyophilized powder for preparing sterile injectable solutions, the preferred methods of manufacture are vacuum drying and spray drying, resulting in a powder of the active ingredient and, if appropriate, further desired ingredients from a solution which has previously been sterilized by filtration. The correct flowability of a solution can be maintained by for example using a coating such as lecithin, in the case of dispersions maintaining the required particle size, or using surfactants. Prolonged absorption of injectable compositions can be achieved by incorporating an agent which delays absorption, for example monostearate salts and gelatin, into the composition.

The active substances of the invention can be administered with a large number of methods which are known to the skilled worker, although subcutaneous injection, intravenous injection or infusion represents the preferred mode of administration for many therapeutic applications. The skilled worker is aware that the route and/or mode of administration depend on the desired result. According to certain embodiments, the active compound can be prepared with a carrier which protects the compound from rapid release, for example a formulation with controlled release, including implants, transdermal patches and microencapsulated delivery systems. It is possible to use biodegradable biocompatible polymers such as ethylene-vinyl acetate, polyanhydrides, polyglycolic acid, collagen, polyorthoesters and polylactic acid. The methods for preparing such formulations are generally known to the skilled worker, see, for example, *Sustained and Controlled Release Drug Delivery Systems*, J. R. Robinson, ed., Marcel Dekker, Inc., New York, 1978.

According to certain embodiments, an active substance of the invention can be administered orally, for example in an inert diluent or an assimilable edible carrier. The active substance (and further ingredients if required) can also be enclosed in a hard or soft gelatin capsule, compressed to tablets or added directly to food. For oral therapeutic administration, the active substances can be mixed with excipients and used in the form of swallowable tablets, buccal tablets, capsules, elixirs, suspensions, syrups and the like. If an active ingredients of the invention are to be administered by a route other than parenteral, it may be necessary to choose a coating of a material which prevents its inactivation.

The active substances of the invention can be administered together with one or more additional therapeutic agents which can be used in the treatment of the disorders described above.

The pharmaceutical compositions of the present invention ordinarily comprise a therapeutically effective amount or a prophylactically effective amount of at least one active substance of the invention. Dosage regimens can be chosen and adapted depending on the desired treatment, whether for example a therapeutic or prophylactic treatment is desired. For example a single dose, a plurality of separate doses distributed over time or a rising or decreasing dosage depending on the requirements of the therapeutic situation can be administered. It is particularly advantageous to formulate parenteral compositions in unit dosage form in order to facilitate administration and ensure a uniformity of dosage.

The treating physician is able to determine without difficulty the dosage form, mode of administration and dosage most suitable for the particular therapy and the particular active substance.

A therapeutically or prophylactically effective around of an active substance of the invention may be for example in the range of 0.1-20 mg/kg and preferably 1-10 mg/kg, without being restricted thereto. It is, of course, possible for these amounts to vary depending on the nature and severity of the condition to be alleviated.

6.2 Vaccines

The AGER-RME or AGER-CDP of the invention and derivatives/equivalents thereof can be used as immunogen for vaccination of a patient to be treated.

Vaccines which can be used for this purpose generally represent a pharmaceutical composition which comprises at least one AGER-RME and/or AGER-CDP of the invention and/or at least one derivative/equivalent of the invention thereof. The composition may additionally comprise a physiologically tolerated carrier and, if appropriate, further excipients, for example immunostimulants.

Whereas suitable carriers can in principle be chosen as desired, the nature of the carrier is generally governed by the route of administration. Thus, the vaccines of the invention can be formulated in particular in a form suitable for parenteral, for example intravenous, intramuscular and subcutaneous, administration. In these cases, the carrier preferably comprises water, saline solution, alcohol, a fat, a wax and/or a buffer.

It is possible to use any one of a large number of immunostimulants in the vaccines of the invention. For example, an adjuvant can be included. Most adjuvants comprise a substance which is intended to protect the antigen from rapid degradation, such as aluminum hydroxide or a mineral oil, and a protein derived from lipid A, Bortadella pertussis or *Mycobacterium tuberculosis*. Suitable adjuvants are usually commercially available, for example complete or incomplete Freund's adjuvant; AS-2; aluminum salts such as aluminum hydroxide (if appropriate as gel) or aluminum phosphate; calcium, iron or zinc salts; an insoluble suspension of acylated tyrosine; acylated sugars; cationically or anionically derivatized polysaccharides; polyphosphazenes; biodegradable microspheres; monophosphoryl-lipid A. Cytokines such as GM-CSF or interleukin-2, -7 or -12 can likewise be used as adjuvants.

7. Therapeutic Methods 7.1 AGER-associated Disorders

The preconditions for the diagnosis and or therapy of "AGER-associated" disorders are improved or created for the first time according to the invention. "Ager-associated" disorders are in particular those associated with an AGER/AGER, AGER/ligand, AGER/receptor, AGER/receptor/ligand, AGER/receptor/coreceptor and/or AGER/receptor/counter-receptor interaction. "Ager-associated" disorders may additionally be characterized by an increased expression or other formation of AGER or AGER ligands.

AGER-associated disorders which should be particularly mentioned are the following diseases mentioned in WO 2004/016229 and/or described in the literature:

amyloidoses, cancer, arthritis, Crohn's disease, chronic inflammatory disorders, acute inflammatory disorders (Schmidt A M et al: J Clin Invest. 2001 October; 108(7):949-55.), cardiovascular disorders, diabetes, diabetic complications (Yan S D et al: Eur J Clin Invest. 1997 March; 27(3):179-81), prion-associated disorders (Sasaki N et al: Neurosci Lett. 2002 Jun. 28; 326(2):117-20), vasculitis, nephropathies, retinopathies and neuropathies (Thornalley P J.: Int Rev Neurobiol. 2002; 50:37-57.). Alzheimer's (Weldon D T et al: Geriatrics. 1997 September; 52 Suppl 2:S13-6; Yan S D et al: Biochim Biophys Acta. 2000 Jul. 26; 1502(1):145-57), rheumatoid arthritis, osteoarthritis (Drinda S et al: Rheumatol Int. 2004 Mar. 26), bowel disease (Foell D et al: Gut. 2003 June; 52(6):847-53), multiple sclerosis (Yan S S et al: Nat. Med. 2003 March; 9(3):287-93.), psoriasis (Foell D et al: Rheumatology (Oxford). 2003 November; 42(11):1383-9.), lupus (Tanji N et al: J Am Soc Nephrol. 2000 September; 11(9):1656-66.), autoimmune diseases in general, sepsis (Liliensiek B et al: J Clin Invest. 2004 June; 113(11):1641-50), arteriosclerosis and restenosis (Schmidt A M et al: Circ Res. 1999 Mar. 19; 84(5):489-97.).

7.2 Therapeutic Approaches

Therapeutic approaches of the invention are based on the modulating effect of at least one of the abovementioned therapeutic agents of an interaction, associated with the disorder to be treated, of the type: AGER/AGER, AGER/ligand, AGER/receptor, AGER/receptor/ligand, AGER/receptor/coreceptor or AGER/receptor/counter-receptor.

The therapeutic effect to be observed with the therapy carried out according to the invention may in this connection be based on an agonistic, partial agonistic, antagonistic or inverse agonistic effect on at least one of these interactions.

The therapeutic effect may in this connection be based in particular on:

a) induction, partial inhibition or complete interruption of a signal pathway; and/or b) formation of complex structures which can be better eliminated by the body or are physiologically/pathophysiologically ineffective.

8. Diagnostic Methods

Diagnostic agents which should be mentioned according to the invention are in particular AGER-RME and AGER-CDP and derivatives/equivalents as defined above, and anti-AGER-RME and anti-AGER-CDP antibodies.

The present invention therefore makes it possible in particular to determine, with qualitative or quantitative improvement, the pathological states defined above by detecting disease-typical antigens or antibodies.

The determination preferably takes place using immunological methods. This is possible in principle with any analytical or diagnostic test method in which antibodies are employed. These include agglutinations and precipitation techniques, immunoassays, immunohistochemical methods and immunoblotting techniques, e.g. Western blotting or dot-blot methods. Also included are in vivo methods, for example imaging methods.

Use in immunoassays is advantageous. Those suitable are both competitive immunoassays, i.e. antigen and labeled antigen (tracer) compete for the antibody binding, and sandwich immunoassays, i.e. the binding of specific antibodies to the antigen is detected using a second, usually labeled antibody. These assays may be either homogeneous, i.e. without separation into solid and liquid phase, or heterogeneous, i.e. bound labels are separated from unbound ones, for example by solid phase-bound antibodies. The various heterogeneous and homogeneous immunoassay formats can be assigned to particular classes depending on the labeling and method of measurement, for example RIAs (radioimmunoassays), ELISA (enzyme linked immunosorbent assay), FIA (fluorescence immunoassay), LIA (luminescence Immunoassay), TRFIA (time-resolved FIA), IMAC (immunactivation), EMIT (enzyme multiplied immune test), TIA (turbidimetric immunoassay), I-PCR (immuno-PCR).

Competitive immunoassays are preferred for the antigen determination of the invention. In this case, labeled antigen (tracer) competes with the antigen of the sample to be quantified for binding to the antibody used. The amount of antigen, that is the amount of antigen, in the sample can be determined from the amount of displaced tracer with the aid of a standard curve.

Of the labels available for these purposes, enzymes have proved to be advantageous. For example, it is possible to use systems based on peroxidases, especially horseradish peroxidase, alkaline phosphatase and β-D-galactosidase. Specific substrates are available for these enzymes, and their conversion can be followed for example by photometry. Suitable substrate systems are based on p-nitrophenyl phosphate (p-NPP), 5-bromo-4-chloro-3-indolyl phosphate/nitro blue tetrazolium (BCIP/NPT), fast red/naphthol-AS-TS phosphate for alkaline phosphatase; 2,2-azino-bis(3-ethylbenzthiazoline-6-sulfonic acid) (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazoline hydrazone (MBTH) for peroxidases; o-nitrophenyl β-D-galactoside (o-NPG), p-nitrophenyl β-D-galactoside and 4-methylumbelliphenyl β-D-galactoside (MUG) for β-D-galactosidase. These substrate systems are in many cases commercially available in a form ready for use, for example in the form of tablets, which may also comprise further reagents such as expedient buffers and the like.

The coupling of labels to peptides or antibodies to prepare tracers can take place in a manner known per se. In addition, a number of labels expediently modified for conjugation to proteins are available, for example biotin-, avidin-, extravidin- or streptavidin-conjugated enzymes, maleimide-activated enzymes and the like. These labels can be reacted directly with the molecule to be used according to the invention.

If a heterogeneous immunoassay format is chosen, the antigen-antibody complex can, for the purpose of separation, be bound to the support for example via an anti-idiotype antibody, e.g. an antibody directed against rabbit IgG, coupled to the support. Supports, especially microtiter plates, which are coated with appropriate antibodies are known and commercially available.

The present invention further relates to immunoassay sets with at least one antibody described above and further components. This comprises a collection, usually as pack unit, of means for carrying out an AGER determination of the invention. To maximize the simplicity of use, these means are preferably provided substantially ready for use. An advantageous arrangement is provided by the immunoassay in kit form. A kit usually comprises a plurality of containers for separate arrangement of components. All the components can be provided in dilution ready for use, as concentrate for dilution or as dry substance or lyophilisate for dissolving or suspending; single components or all the components may be frozen or be stored at ambient temperature until used. Sera are preferably shock-frozen, for example at −20° C., so that in these cases an immunoassay must be kept preferably at freezing temperatures before use.

Further components added to the immunoassay may be: standard protein, tracer; control serum, microtiter plates, preferably coated with antibody, buffer, for example for testing, for washing or for reacting the substrate, and the enzyme substrate itself.

General principles of immunoassays and the generation and use of antibodies as laboratory and clinical aids are to be found for example in Antibodies, A Laboratory Manual (Harlow, E., and Lane, D., Ed., Cold Spring Harbor Laboratory, Cold Spring Harbor, N.Y., 1988).

9. Screening Methods

The invention also relates to methods for detecting effectors of the AGER receptor, where a sample in which an effector is suspected is incubated with an AGER-RME or AGER-CDP polypeptide, and the mixture is investigated for the formation of an effector-AGER-RME or effector-AGER-CDP complex.

Such effectors may have an agonistic, partial agonistic, antagonistic or inverse agonistic effect. They may be for example synthetic low molecular weight substances, synthetic peptides, natural or synthetic antibody molecules or natural substances.

Such methods of the invention are usually carried out as in vitro screening methods with which it is possible to select from a large number of different substances those which appear to be most promising in relation to future use.

For example, extensive substance libraries comprising a large number of potential active substances can be set up by means of combinatorial chemistry. Screening of combinatorial substance libraries for substances having a desired activity can be automated. Robot screening devices are used for efficient evaluation of the individual assays arranged preferably on microtiter plates. Thus, the present invention also relates to screening methods, i.e. both primary and secondary screening methods, in which preferably at least one of the methods described below is used. If a plurality of methods is used, this is possible sequentially or simultaneously on one and the same sample or on different samples of a substance to be investigated.

An efficient technique for carrying out such methods is the scintillation proximity assay, abbreviated to SPA, which is known in the area of active substance screening. Kits and components for carrying out this assay can be purchased commercially, for example from Amersham Pharmacia Biotech. In principle, solubilized or membrane-bound receptors are immobilized on small fluoromicrospheres comprising scintillant. If, for example, a radioligand binds to the immobilized receptors, the scintillant is excited to emit light because the scintillant and radioligand are in spatial proximity.

A further efficient technique for carrying out such methods is the FlashPlateR technique known in the area of active substance screening. Kits and components for carrying out this assay can be purchased commercially, for example, from NEN Life Science Products. This principle is likewise based on microtiter plates (96- or 384-well) which are coated with scintillant.

Screening methods using the actin cytoskeletal rearrangement (ACR) assay described herein are likewise applicable.

The substances or parts of substance mixtures identifiable by these methods are likewise an aspect of the present invention.

The invention is now explained in more detail with reference to the following non-limiting examples of production and use Experimental Section I. General Information a) Constituents of Culture Media
RPMI-Glutamax (Invitrogen, Carlsbad, USA)
Geneticin (G418); (antibiotic; selection marker) (Invitrogen)
Fetal Bovine Serum (FBS) Dialyzed, (Invitrogen)
Antibiotic-Antimycotic (Invitrogen)
Zeocin (antibiotic; selection marker) (Invitrogen)
LIPOFECTAMINE (Invitrogen)

b) Cells

Human embryonic kidney cells (HEK293) (ATCC=American Tissue Culture Collection, order No.: CRL-1573) were stably transfected with Rho (HEK293-RhoA) or with Rho in combination with the receptor complex NgR/p75 (HEK293-RhoA/NgR/p75). The cells were maintained in RPMI-Glutamax medium supplemented with 5% heat-inactivated fetal bovine serum (FBS), HEPES (10 mM), penicillin (100 U/ml), streptomycin (100 mM) and either neomycin (HEK293-RhoA) or neomycin in combination with zeocin (HEK293-RhoA/NgR/p75).

c) Reagents

| | |
|---|---|
| Nogo-66, comprising an N-terminal alkaline phosphatase Tag (AP-Nogo-66) | |
| L-alpha-lysophosphatitic acid (LPA) | Sigma, Munich, DE |
| Anti-RhoA antibodies | Santa Cruz Biotechnology, Santa Cruz, USA |
| Anti-Nogo-66 antibodies (NogoA12-A) | Alpha Diagnostics International, San Antonio, Texas, USA |
| Alexa Phalloidin 568 or 488 (dye for fluorescent staining of F-actin) | Molecular Probes, Eugene, USA |
| DAPI (Hoechst 33342, trihydrochloride, trihydrate) | Molecular Probes Inc., Eugene, USA | d) General Assay Methods

1) ACR assay with Immunofluorescence Measurement:

$1 \times 10^4$ cells were transfected into microtiter plates with 96 wells two days before the stimulation. The cells were stimulated with a suitable reagent (e.g. LPA or AP-Nogo-66) in culture medium (RPMI-Glutamax) comprising 5% FCS. After a stimulation period of 5 to 10 minutes, the activation was stopped with cold PBS. The cells were fixed with 3-4% strength paraformaldehyde solution, permeabilized with PBS comprising 0.2% Triton X-100, and incubated with phalloidin Alexa 568 or 488 for 30-45 minutes. Incubation with DAPI additionally took place for 5 minutes for nuclear staining. The cells were visualized with the aid of an epifluorescence microscope (Axiovert 25).

Fluorescence micrograms were recorded using a cooled Zeiss CCD camera.

2) FACS Analysis

Reagents:

| | |
|---|---|
| Mouse anti-human p75; IgG monoclonal antibody | Sigma N-5408 |
| Anti-mouse-FITC | Sigma F-5262 |
| Goat anti-human NogoR | R&D Systems; AF1208 |
| Anti-goat-FITC | Sigma F7367 |

Procedure:

Firstly, the HEK293 cells were washed with PBS. Adherent cells were detached with PBS comprising 5 mM EDTA. Subsequently, $2 \times 10^6$ cells were transferred into an Eppendorff vessel and centrifuged at 1300 rpm for 2 minutes. The cells were resuspended in PBS comprising 1% BSA (1 ml/vessel) and centrifuged at 1300 rpm for 2 minutes.

The pellets were again resuspended with 0.1 ml of PBS/1% BSA including primary antibody (mouse anti-human p75 1:100, or goat anti-human NogoR 1:50) and incubated at 4° C. for 90 minutes. Subsequently, 0.1 ml of PBS/1% BSA was added, mixed and centrifuged at 1300 rpm for 2 minutes.

The pellets were resuspended in PBS comprising 1% BSA (0.1 ml/vessel) and secondary antibody (anti-mouse-FITC 1:100; or anti-goat-FITC 1:100) and incubated at 4° C. for 60 minutes.

PBS comprising 1% BSA (1 ml/vessel) was added, mixed and centrifuged at 1300 rpm for 2 minutes. After centrifugation, the pellets were again resuspended in PBS/0.1% propidium iodide to detect dead cells. Resuspension was followed by FACS analysis (FACScan, Becton Dickinson, Heidelberg, Germany).

II. Preparation Examples

Preparation Example 1

Preparation of AP-Nogo66 a) Cloning of the Nogo66 fragment of hNogoA

The starting point was the published hNogoA sequence (NCBI): AF148537. The two following synthetic oligonucleotides were derived from the published sequence:

Mez 402: GCCACC ATGAGGATATACAAGGGTGTGATCC (SEQ ID NO: 9); oligo from amino acid R1055 (italic) with start ATG (underlined) and Kozak sequence (bold)

Mez 404: CTTCAGAGAATCAACTAAATCATC (SEQ ID NO: 10); oligo up to amino acid K1120 (bold)

A PCR was carried out with these two oligos in frontal cortex cDNA as template (prepared using Superscript first strand synthesis system for RT-PCR; Invitrogen, Carlsbad, Calif.) (Novak et al., Brain Res. Mol. Brain, 2002, 107(2): 183-189). The reaction was carried out by a standard method, like Innis et al. (PCR Protocols. A Guide to Methods and Applications, Academic Press (1990)) with Herculase (Stratagene, La Jolla, USA). The resulting DNA fragment with a size of 207 bp was purified using the QIAEX II gel extraction kit (QIAGEN GmbH, Hilden, Germany) as specified by the manufacturer. The amplified, purified fragment was put into pcDNA3.1V5-His TOPO (pcDNA3.1/V5-His TOPO TA Expression Kit, #K4800-01). The construct obtained in this way, pcDNA3.1V5-His hNOGO66, was used to transform *E. coli* TOP10 cells (Invitrogen, Carlsbad, Calif.) by standard methods as described in Sambrook et al. (Molecular Cloning. A Laboratory Manual, Cold Spring Harbor, (1989)). Selection of plasmid-harboring cells was achieved by the antibiotic ampicillin.

Identification of nine clones by PCR showed a band of the correct size of 207 bp for three clones. The correctness of the sequence was checked by sequence analysis.

The coding Nogo66 sequence was cut out of the above plasmid pcDNA3.1V5-His hNOGO66 with XbaI and cloned into the plasmid pAP-tag5 (GenHunter Cooperation, Nashville, Tenn., USA) via XbaI. The plasmid pAP-tag5/PPC/hNOGO66 No. 5 (SEQ ID NO: 11), depicted in FIG. 2, is obtained.

b) Preparation of the Stable Cell Line:

HEK293 cells were cultured in growth medium (DMEM with 10% fetal bovine serum with addition of penicillin/streptomycin) at 37° C. and 5% $CO_2$. For the transfection, the cells were seeded in plates with 6 wells ($1 \times 10^6$ per well) and incubated overnight. The cells were transfected with a cocktail which comprised 1 µg of plasmid DNA (pAP-tag5/PPC/hNOGO66 No. 5) and 3 µl of Fugene6 (ROCHE Diagnostics, Mannheim) as stated by the manufacturer. Two days later, the cells were detached by treatment with trypsin and transferred into a cell culture bottle with a base area of 175 cm$^2$, and selection was started by adding 150 µg/ml zeocin to growth medium. Zeocin-resistant cell colonies which grew were detached with trypsin after about 4 weeks and isolated in 96-well plates using a cell sorter. After about three weeks, an aliquot of the medium supernatant of the grown single-cell colonies, whose confluence at this time was estimated at between 5 and 85%, was pipetted onto nitrocellulose. Protein expression was detected by adding a solution of NBT (nitroblue tetrazolium salt) and BCIP (5-bromo-4-chloro-3-indolyl phosphate) via the activity of the alkaline phosphatase on the basis of the resulting stain.

c) Expression of AP-Nogo66:

An HEK293 clone (clone No. 5) which produces AP-Nogo66 was expanded in culture medium (RPMI Glutamax+10% FCS, 150 µg/ml zeocin, antibiotic/antimycotic) by multiple passage (about 20) in culture bottles. The AP-Nogo66 expression was checked after every second or third passage in a dot blot assay (with NBT/BCIP reagent).

In order to produce AP-Nogo66 in serum-free medium, the cells were initially cultured almost to confluence in triple flasks, then the medium was changed to expression medium (Pro293a-CDM medium (Biowhittaker; #12-764Q), 2 mM glutamine, antibiotic/antimycotic). These cells were then cultured at 37° C. for 3-4 days, and the supernatants were removed and centrifuged (1500 rpm, 5 min). The supernatants were collected at −80° C. For further processing, they were thawed, mixed with proteinase inhibitors (PMSF 0.1 mM, Pefabloc SC 1 mM) and concentrated in Amicon tubes (Millipore), and the AP-Nogo66 concentration was determined (about 3 µg/ml) (Mw of monomeric AP: 67 kDa and monomeric AP-Nogo66 about 75 kDa in SDS gels).

The AP-Nogo66 pool was immunoprecipitated with anti-AP-agarose. The precipitate was denatured by heating in the presence of 5% mercaptoethanol at 95° C. for 10 minutes, and thus removed from the agarose beads, and finally verified by Western analysis using antibodies with specificity for AP and Nogo66. It was determined by gel chromatography (Superose 12, Amersham Biosciences, mobile phase: 20 mM sodium phosphate, 140 mM sodium chloride, pH 7.4) that AP-Nogo66 migrates as dimer and has an Mw of about 140 kDa. It was found in preliminary experiments that AP-Nogo66, but not GST-Nogo66, was functionally active. It is therefore presumed that NgR ligands must possibly all be in the form of dimers in order to be functional. As shown by the crystal structure of the alkaline phosphatase, the dimerization is induced by the AP tag (experiments not shown).

Preparation Example 2

Preparation of Recombinant HEK Cell Lines for Carrying Out the Functional Actin Cytoskeletal Rearrangement (ACR) Assay 1. Preparation of the Required Constructs
a) Cloning of hp75; preparation of pcDNA3.1(V5-His)hp75 No. 16 (FIG. 3d)

The starting point was the published sequences for human p75: NM_002507; M14764 (which are both 100% identical). The following oligonucleotides were derived from the published sequence:

Mey 36: GCCACCATGGGGGCAGGTGCCACC (SEQ ID NO: 13); oligo with start codon (bold) with Kozak sequence (italic)

Mey 35: TCACACTGGGGATGTGGCAG (SEQ ID NO: 12); oligo with stop codon (bold) in a base exchange of T instead of C (underlined) because the oligo is derived from the published rat sequence Mey 71: GCAGCCCCATCAGTCCGC (SEQ ID NO: 14); oligo starting 64 base pairs in front of ATG A PCR was then carried out (in analogy to the Nogo 66 cloning, example 1) with the primer pair Mey 35/71 in cDNA from the cell line SH-SY5Y (human neuroblastoma cell line ATCC # CRL-2266). The PCR with Mey 35/71 afforded a 1348 bp fragment. This was purified.

A subsequent PCR with the primer pair Mey 35/36 in the Mey 35/71 fragment yielded a clear band (fragment size: 1284 bp). This was purified. This band was then inserted into pcDNA3.1/V5-His TOPO vector (SEQ ID NO:15) (pcDNA3.1(V5-His) TOPO TA Expression Kit Invitrogen #K4800-01) uncut (topoisomerase principle). The construct obtained in this way (pcDNA3.1 hp75) was used to transform TOP10 cells by standard methods (analogous to Nogo 66 cloning, example 1).

13 clones of this transformation were checked, and four clones with the correct orientation (Nos. 13, 15, 16 and 18) were identifiable. Clone No. 16 was used further. The sequence of the contained construct (pcDNA3.1(V5-His) hp75 No. 16; cf. also FIG. 3d) is depicted in SEQ ID NO: 16. Further information on this sequence is summarized in the following section.

| | | |
|---|---|---|
| Human p75 | start: 40 | stop: 1320 |
| Neomycin | start: 2596 | stop: 3390 |
| Ampicillin | start: 4897 | stop: 5757 compl. |
| Bgh pA | start: 1487 | stop: 1701 |
| SV40 pA | start: 3416 | stop: 3654 |
| His tag | start: 1441 | stop: 1458 |
| V5 epitopes | start: 1397 | stop: 1438 |
| F1 ori | start: 1764 | stop: 2177 |
| SV40 promoter + ori | start: 2242 | stop: 2567 |
| pUC ori | start: 4086 | stop: 4759 | b) Preparation of pIRES hp75

The plasmid pIRES (Clontech, Palo Alto, USA) was cut with Xba I and Not I (Roche Diagnostics) using a restriction mixture (40 µl; 1.5 h at 37° C.) comprising 5 µg of DNA, 2 µl of Xba I, 2 µl of Not I, 4 µl of 10× buffer H (Roche) and 32 µl of double-distilled water. The excised fragment was isolated in a conventional way from a DNA gel using the Qiagen gel extraction kit.

The plasmid pcDNA3.1 hp75, prepared as described above, was cut with Spe I and Not I (Roche Diagnostics) using a restriction mixture (40 µl; 1.5 h at 37° C.) comprising 5 µg of DNA, 2 µl of Spe I, 2 µl of Not I, 4 µl of 10× buffer H (Roche), 32 µl of double-distilled water. The excised fragment was isolated in a conventional way from a DNA gel using the Qiagen gel extraction kit.

Figure 3A:
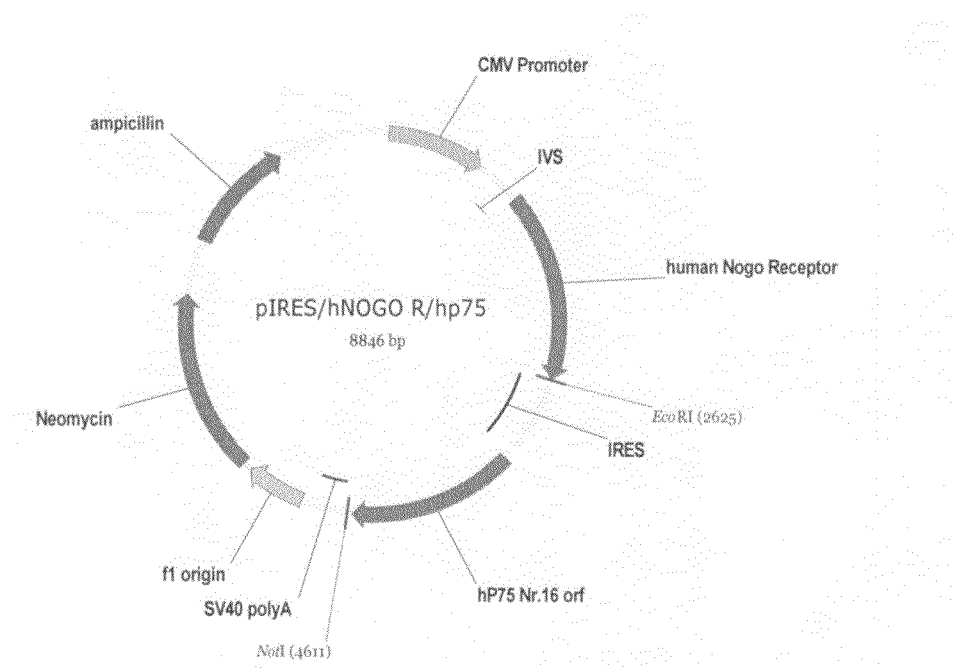
FIG. 3 shows the plasmid maps of various plasmids used according to the invention:
pIRES hNgR hp75 NgR (SEQ ID NO:18) (FIG. 3a)
pcDNA3 hRhoA wt (SEQ ID NO:23) (FIG. 3b)
pcDNA4 His Myc(mycHis)A hRhoA wt (SEQ ID NO:21) (FIG. 3c)
pcDNA3.1 (V5-His)hp75 No. 16 (SEQ ID NO:16) (FIG. 3d)
Figure 3B:
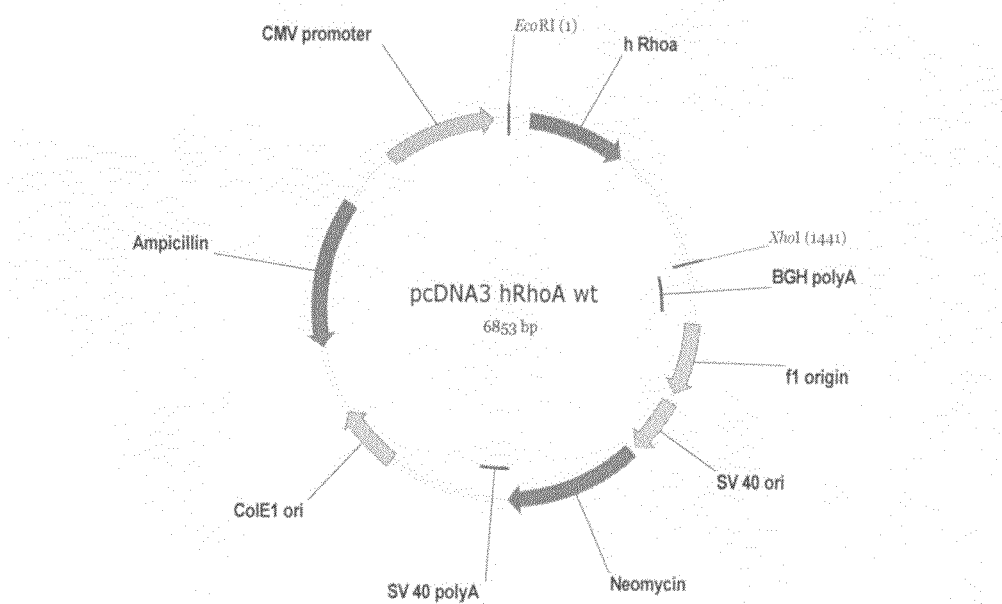

The restriction fragments prepared in this way were ligated at 16° C. overnight using the following mixture: 5 µl of hp75 construct, 2 µl of cut pIRES, 1.5 µl of T4-DNA ligase (Roche), 3 µl of 10× buffer T4 (Roche), 20.5 µl of double-distilled water. This ligation, which is referred to as pIRES hp75, was then transformed into the bacterial strain Super-Comp XL2 Blue (Stratagene).

c) Preparation of pIRES hNgR hp75 (FIG. 3a)

pcDNA hNgR CDS1, obtained commercially from RZPD (Deutsches Resourcenzentrum für Genomforschung GmbH, clone No.: IRAL-p962L1427Q2), comprising the coding sequence for human Nogo receptor (hNgR), was digested using a restriction mixture of 13 µl; 1 h at 37° C. comprising 5 µg of DNA, 1.5 µl of Hind III (Roche), 1.5 µl of 10× buffer B (Roche) and 10 µl of double-distilled water (blunt end). The excised fragment was isolated in a conventional way from a DNA gel using the Qiagen gel extraction kit.

The ends were filled in by incubating 20 µl of the cut pcDNA hNgR CDS1 construct in a mixture (100 µl; 30 min 11° C.) comprising 2 µl of T4-DNA polymerase (Roche), 10 µl of 10× buffer T4 (Roche), 1 µl of 100 mM DTT (Gibco), 10 µl of 20 mM NTP mix (Stratagene) and 77 µl of double-distilled water. The T4 fill-in was isolated from a DNA gel using the Qiagen gel extraction kit.

For the dephosphorylation in order to avoid religation of the blunt ends, 50 µl of the T4 fill-in of the hNgR CDS1 construct were incubated with 2 µl of alkaline phosphatase (Roche), 10 µl of 10× buffer (Roche) and 38 µl of double-distilled water initially at 37° C. for 30 min and then at 65° C. for 15 min. The dephosphorylation construct obtained in this way was finally purified using the Qiagen Hit clean-up.

The purified pcDNA h NgR Hind III blunt fragment was then digested with EcoRI using a restriction mixture (15 µl, 1 h at 37° C.) comprising 10 µl of eluate (from Qiagen Hit clean-up), 1.5 µl of EcoRI (Roche), 1.5 µl of 10× buffer H (Roche) and 2.0 µl of double-distilled water and isolated after restriction from a DNA gel using the Qiagen gel extraction kit.

pIRES hp75 (prepared as above) was opened with EcoR I and Hind III using a restriction mixture (27 µl, 1.5 h at 37° C.) comprising 5 µg of DNA, 1.5 µl of EcoR I, 1.5 µl of Hind III, 4 µl of 10× buffer H (Roche) and 20 µl of double-distilled water. The desired hP75 fragment was isolated after restriction from a DNA gel using the Qiagen gel extraction kit and ligated with the hNgR construct prepared above, using a ligation mixture comprising 5 pNgR construct, 2 µl of cut pIRES hp75, 1.5 µl of T4-DNA ligase (Roche), 3 µl of 10× buffer T4 (Roche) and 20.5 µl of double-distilled water at 16° C. overnight. The resulting construct pIRES hNgR hp75 (FIG. 3a; SEQ ID NO: 18) was then transformed into the bacterial strain SuperComp XL2 Blue (Stratagene).

Figure 3C:
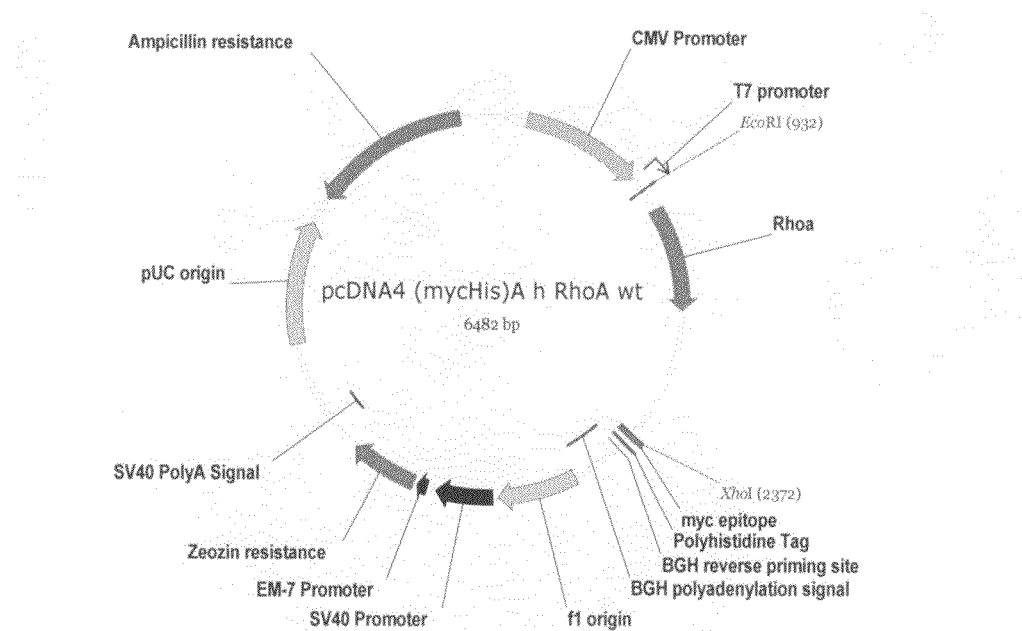
Figure 3D:
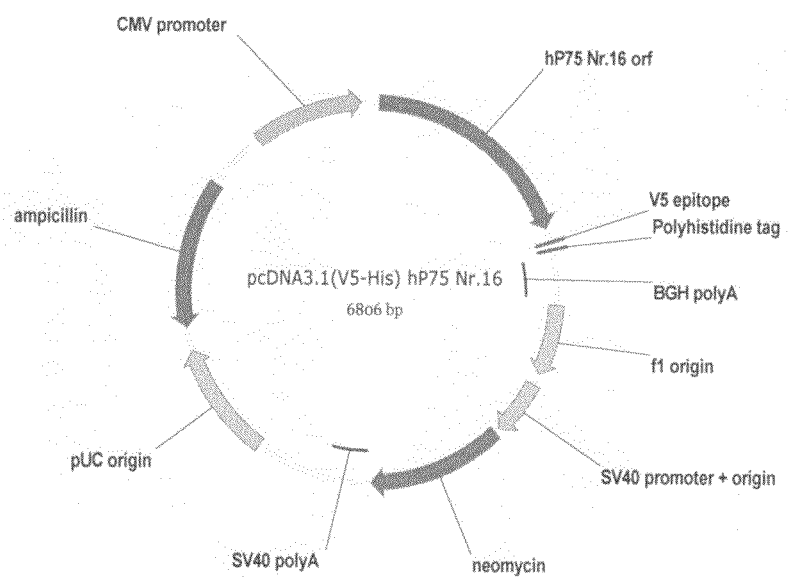

Further sequence information on pIRES hNgR hp75 is summarized in the following section:

| | |
|---|---|
| CMV prom. | 108-857 |
| NOGO R | 1202-2620 |
| IRES | 2658-3238 |
| hp75 | 3294-4574 |
| SV40pA | 4648-4869 |
| fl ori | 4964-5419 |
| Neo | 5483-6856 |
| amp | 7261-8121 |
| pUC ori | 8266-93 compl. | d) Preparation of pcDNA4(mycHis)A hRhoA wt (FIG. 3c)

The plasmid pOTB7 RhoA (obtained commercially from RZPD, Deutsches Resourcenzentrum für Genomforschung GmbH, clone No.: IRAL-p962A174), which comprises the coding sequence for human RhoA GTPase, was digested using the following restriction mixture (25 µl, 1.5 h at 37° C.) comprising 5 µg of DNA, 1.5 µl of EcoR I, 1.5 µl of Xho I (Roche), 3 µl of 10× buffer H (Roche) and 19 µl of double-distilled water.

In a second mixture, pcDNA4(mycHis) (Invitrogen, Carlsbad, USA) was likewise digested using the following restriction mixture (25 µl, 1.5 h at 37° C.) comprising 5 µg of DNA, 1.5 µl of EcoR I, 1.5 µl of Xho I (Roche), 3 µl of 10× buffer H (Roche) and 19 µl of double-distilled water.

The cut fragments were then purified and ligated as described above, resulting in the plasmid pcDNA4(mycHis)A h RhoA wt (cf. FIG. 3c: SEQ ID NO: 21). The resulting construct was then transformed into the bacterial strain Supercomp XL2 Blue (Stratagene).

Further sequence information on pcDNA4(mycHis)A hRhoA wt is summarized in the following section:

| | |
|---|---|
| CMV prom. | 197-851 |
| RhoA | 1058-1636 |
| His | 2437-2454 |
| myc | 2392-2421 |
| Bgh pA | 2480-2707 |
| SV40 pA | 4143-4273 |
| fl ori | 2753-3181 |
| amp | 5477-6334 compl. |
| pUC ori | 4656-5329 |
| Zeo | 3639-4010 |
| EM7 prom. | 3565-3620 |
| SV40 prom. | 3209-3517 | d) Preparation of pcDNA3 hRhoA wt (FIG. 3b)

The preparation takes place in analogy to pcDNA4(mycHis)A hRhoA wt, but using the plasmid pcDNA3.1V5-His TOPO described above instead of pcDNA4(mycHis).

Further sequence information on pcDNA3 hRhoA wt (cf. FIG. 3b; SEQ ID NO: 23) is summarized in the following section:

| | |
|---|---|
| CMV prom. | 6124-6778 |
| h RhoA | 127-705 |
| Bgh pA | 1478-1718 |
| SV40 pA | 3402-3597 |
| SV40 ori | 2259-2584 |
| ColE1 ori | 4141-4515 |
| fl ori | 1788-2201 |
| Neo | 2620-3411 |
| amp | 4919-5779 compl. |

2. Generation of Stable Recombinant HEK Cell Lines
a) Preparation of the Double Transfectant HEK293 NgR/p75

HEK293 wild-type cells (cultured in RPMI Glutamax+ 10% dial. FCS+1% antibiotic-antimycotic) were transfected in a first transfection step with the plasmid pIRES hNgR hp75. For this purpose for each mixture, 2 µg of plasmid DNA were mixed in 100 µl of serum-free RPMI-Gutamax medium and 2×10$^6$ cells in 12 µl of LIPOFECTAMINE in 100 µl of serum-free RPMI-Gutamax medium in culture dishes with 10 wells, and incubated at room temperature for 15 to 20 minutes. The total volume was then made up to 1 ml for each transfection mixture using serum-free medium. Subsequently, 2 ml of serum-free RPMI-Gutamax medium were added to each dish, and incubation was carried out at 37° C. for 6 h. The medium was then changed to RPMI-Glutamax+ 5% dialyzed FCS and incubation was carried out at 37° C. for 1 day. The contents of the dishes were then split (in various dilutions: 1:10; 1:50, 1:100, 1:250, 1:500, 1:1000; 1 mixture/dish per dilution) (in RPMI-Glutamax+10% dialyzed FCS+ 1% antibiotic-antimycotic+G418; 800 µg/ml)

Clones were isolated from the dilution which yielded the first separated clones. Sterile glass minicylinders (BASF) were cautiously dipped by one end in sterile petrolatum (BASF) using sterile tweezers. The petrolatum-wetted end of the glass minicylinders was cautiously placed over the previously selected single clones. The single clone should be completely surrounded by the glass minicylinder. Then an Eppendorf pipette with a sterile tip was used to add 40 µl of trypsin (Gibco, trypsin-EDTA) to the glass minicylinder. The trypsin was allowed to act on the cells for 1-2 minutes. The cells were resuspended by drawing up and discharging the trypsin with an Eppendorf pipette (sterile tip) several times (3-4 times). The resuspended cells were transferred with the Eppendorf pipette completely from the glass minicylinder into a 24-well plate (tissue culture plate, Falcon, Becton Dickinson, each well contained 1 ml of RPMI-Glutamax medium+5% dialyzed FCS).

Positive clones were detected by FACS as described above. Overexpression of the receptors NgR and p75 on the cell surface was moreover determined (results not shown).

b) Preparation of the Triple Transfectant HEK293 RhoA/NgR/p75

A positive clone prepared as in a) (clone 5) of the cell line HEK293 NgR/p75 is transfected in an analogous manner with the plasmid pcDNA4(mycHis)A hRhoA. In the last step, the mixtures are split in RPMI-Glutamax (+10% dialyzed FCS+1% antibiotic-antimycotic+G418; 800 µg/ml, +zeocin 125 µg/ml)

Positive clones were detected by testing them for RhoA expression by immunoblotting and for expression of the NgR and p75 receptors by FACS analysis.

Figure 4A:
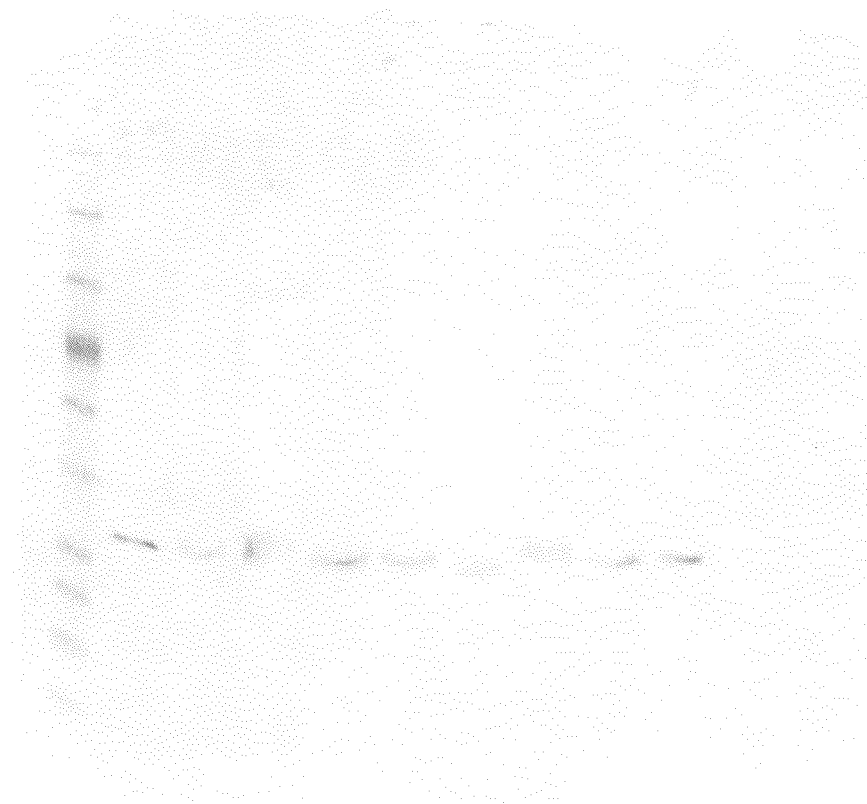
FIG. 4a shows the immunological detection of expressed Rho by positive clones isolated according to the invention (#1 to #8) of the triple transfectant HEK293 RhoA/NgR/p75 (clones 1 to 9), positive control (C) obtained by transient transfection with 100 ng of pcDNA4(mycHis)A hRhoA wt; the marker (M) used was Benchmark Prestain Protein Ladder, Invitrogen, order number #10748-010.

To detect RhoA, a cell homogenate derived from the particular clone was fractionated by SDS-PAGE gel electrophoresis (NuPAGE polyacrylamide gel 4-12%, 1.5 mm thick (Invitrogen Carlsbad, USA); the protein samples were denatured with 5% mercaptoethanol) and, after immunoblotting, tested with monoclonal mouse anti-RhoA antibody by a standard method. A typical result is depicted in FIG. 4a. A RhoA band with a molecular weight of about 21 kD is observed with positive clones.

Expression of NgR and p75 was detected by carrying out a FACS analysis as described above. A typical result is depicted in FIG. 4b.

Preparation Example 3

Preparation of Recombinant Human sRAGE Protein and N-terminally Truncated sRAGE a) Preparation of sRAGE Protein (sRAGE 1-331) (SEQ ID NO:37)

The basis for the expression and purification of recombinant sRAGE protein was the HEK 293 cell line "293/6.1 sRAGE H is 6" which was stably transfected with the vector pcDNA3 (−) 6.1 C HIS A.

The preparation of this cell line is firstly described below: Standard techniques of molecular biology were carried out in accordance with Sambrook, J. and Russell D. (2001) Molecular Cloning: A Laboratory Manual: 2nd. Edition, Cold Spring Harbor Press, NY.

Total RNA from lymphocytes (PBL) underwent reverse transcription using the Superscript RT-PCR system (Invitrogen, Carlsbad, USA) in order to amplify, using the oligonucleotide primers

```
                                           (SEQ ID NO: 25)
RAGE-SE: CCG AAT TCC GGA AGC AGG ATG GCA GCC G
und
                                           (SEQ ID NO: 26)
RAGE-AS: CCC TCG AGC CCC TCA AGG CCC TCA GTA CTA CT
``` the RAGE cDNA as described in the Genbank Ref. Seq. sequence NM_001136. After gel purification using the QIAquick gel extraction kit (Qiagen GmBH, Hilden, Germany), the cDNA was cut with the restriction endonucleases EcoR1 and XhoI in order to be ligated, after renewed gel purification, into the vector pcDNA 3 (Invitrogen, Carlsbad, USA) which was likewise cut with XhoI/EcoR1. After transformation into *E. coli* XL-1 blue cells (Invitrogen, Carlsbad, USA), a positive recombinant clone was amplified, the sequence was verified, and the plasmid DNA was isolated using the Plasmid Mini-Kit (Qiagen, Hilden, Germany). Starting from this plasmid, called pcDNA3/RAGE 2.6 and using the primers

```
                                           (SEQ ID NO: 27)
N-SE A: AGT AAC GGC CGC CAG TGT GCT GGA ATT CGG A
and
                                           (SEQ ID NO: 28)
C-SE B: CCG GTA CCA CCT GCA GTT GGC CCC TCC TCG CC
``` the cDNA (Genbank Ref. Seq. sequence NM_001136) of the soluble RAGE (sRAGE) was amplified. The PCR product was cut with EcoR1 and Kpn1 restriction endunucleases and, after the purification described above, ligated into the vektor "pcDNA3.1(−) Myc HIS" (Invitrogen, Carlsbad, USA) which had been linearized with EcoR1/Kpn1. The plasmid vector "pcDNA 3 (−) 6.1 C HIS A" newly produced in this way was transfected into HEK 293 using the transfection reagent "Superfect" (Qiagen, Hilden, Germany) in accordance with the manufacturer's statements. After selection of the "positive" cells with 800 μg/ml G418 in MEM medium (#M4528, Sigma, Munich, Germany)+10% FCS, 2 mM L-glutamine, 100 U/ml penicillin/streptavidin (Invitrogen, Carlsbad, USA), serial dilutions of the cell suspension were prepared so that it was possible, starting from a single clone, to identify the cell line "293/6.1 sRAGE H is 6".

The identity of sRAGE expression and secretion of the protein into the culture medium was checked in a Western blot with RAGE-specific antibodies (Santa Cruz; # sc5563).

For protein production, this cell line was grown in a stack of 4×20 l tanks in serum-containing MEM (see above). The cells were then cultivated in serum-free medium Pro293a-CDM (#12-764Q, BioWhittaker, Vervier, Belgium) at 37° C. for 3 days before the medium supernatant was removed and concentrated through "Hemolflow F-Series High-Flux" columns (Fresenisus Medical Care AG, Bad Homburg, Germany) to 1400 ml.

The protein was purified by "Immobilized Metal Ion Affinity Chromatography (IMAC) and was carried out by Diarect AG (Freiburg, Germany). The NiNTA column material employed was "chelating sepharose FF" (Amersham-Bioscience, Upsala, Sweden). Equilibration, binding to the column matrix and purification took place in accordance with the manufacturer's statements. The protein was eluted stepwise with increasing imidazole concentrations. The various fractions were examined for the content of sRAGE protein by Western blotting with anti-HIS antibodies. The purified sRAGE protein (Genbank Ref. Seq. sequence NM_001136) was eluted specifically at 250-500 mM imidazole. The fractions obtained in this way were combined, concentrated and dialyzed against PBS three times (2×4 h, 1×16 h).

b) Prepartion of N-terminally Truncated sRAGE (sRAGE 102-331) (SEQ ID NO:34)

The cDNA of the N-terminally truncated RAGE ecktodomain was amplified starting from the plasmid "pcDNA3/RAGE 2.6" (cf. preparation example 3a) using the primers

```
                                           (SEQ ID NO: 35)
"N-trunc HindIII":
CGA AGC TTG ATG AAC AGG AAT GGA AAG GAG ACC AAG
and
                                           (SEQ ID NO: 36)
"N-trunc XhoI":
TCC TCG AGC ACC TGC AGT TGG CCC CTC CTC GCC T.
```

After gel purification using the QIAquick gel extraction kit (Qiagen GmbH, Hilden, Germany), the cDNA was cut with the restriction endonucleases HindIII and XhoI in order to be ligated, after renewed gel purification, into the vector psecTAG 2A (Invitrogen, Carlsbad, USA) which was likewise cut with HindIII/XhoI. After transformation into *E. coli* "TOP10 One Shot" cells (Invitrogen, Carlsbad, USA), a positive recombinant clone was amplified, the sequence was verified, and the plasmid DNA was isolated using the plasmid minikit (Qiagen, Hilden, Germany).

The plasmid vector "psecTAG/N—C trunc sRAGE1" newly produced in this way was expressed using the "FreeStyle" transfection system (Invitrogen, Carlsbad, USA) in accordance with the manufacturer's statements. After 96 hours, the cells were spun down and the serum-free supernatant (60 ml) was employed for protein purification.

The protein purification took place by immobilized metal ion affinity chromatography (IMAC). NiNTA Superflow (Qiagen, Hilden, Germany) was employed as NiNTA column material. Equilibration and binding to the column matrix took place in accordance with the manufacturer's statements. The protein was eluted in elution buffer [PBS, 160 mM NaCl, 150 mM imidazole, pH 8.0]. The various fractions were checked in a PAGE for the content of N—C truncated sRAGE protein. The first three 250 μl fractions were combined, concentrated and dialyzed against TBS. The final protein concentration was determined by photometry.

Preparation Example 4 sRAGE Peptide Fragments

The following peptides were prepared by standard methods of peptide synthesis:

```
NtermR31:
QNITARIGEPLVLKCKGAPKKPPQRLEWKLN       (SEQ ID NO: 6)

NtermR13:
CKGAPKKPPRQRLE                        (SEQ ID NO: 3)

ScraNtermR31:
APLACPRELIKGKWEVKPKRNPKNQLTIGQL       (SEQ ID NO: 7)

ScraNtermR13:
GKPRAPKCLKPEQ                         (SEQ ID NO: 8)
```

Preparation Example 5

Preparation of His-NogoR Fusion Protein

The basis for the expression and purification of recombinant His-NogoR fusion protein (Genbank:NM_023004) was the HEK 293 cell line "CHO" stably transfected with the vector "pcDNA4/hNogoR-TM6".

The preparation of this cell line is firstly described below: standard techniques of molecular biology were carried out in accordance with Sambrook and Russel (2001).

The starting point for preparing the NgR-HIS expression plasmid was the cDNA clone pOTB7 IRALp962L1427Q2 which was purchased from RZPD GmbH (Berlin, Germany). The desired coding nucleotide sequence was amplified from the plasmid DNA by PCR using the oligonucleotide primers:

```
                                      (SEQ ID NO: 29)
hNogoR Hind III:
CCAAGCTTATGAAGAGGGCGTCCGCTGGAGGGAG (SEQ ID NO: 30)
hNogoR Eco RI-TM:
CCGAATTCTAGGGCACCTGAGCCTTCTGAGTCACC.
```

After gel purification using the QIAquick gel extraction kit (Qiagen GmbH, Hilden, Germany), the cDNA was cut with the restriction endonucleases HindIII and EcoR1 in order to be ligated, after renewed gel purification, into the vector pcDNA4/MycHIS A (Invitrogen, Carlsbad, USA) which was likewise cut with HindIII/EcoR1. After transformation into *E. coli* Top10 One Shot cells (Invitrogen, Carlsbad, USA), a positive recombinant clone was amplified, the sequence was verified, and the plasmid DNA was isolated using the Plasmid Mini-Kit (Qiagen, Hilden, Germany).

The plasmid vector "pcDNA4/hNogoR-TM6" newly produced in this way was transfected into CHO-K1 using the transfection reagent "Fugene 6" (Roche, Mannheim, Germany) in accordance with the manufacturer's statements. After selection of the "positive" cells with 800 µg/ml G418 in MEM medium (#M4528, Sigma, Munich, Germany) comprising 10% FCS, 2 mM L-glutamine, 100 U/ml penicillin/streptavidin (Invitrogen, Carlsbad, USA), serial dilutions of the cell suspension were prepared so that it was possible to identify the cell line "CHO-K1/" starting from a single clone.

The identity of the Nogo receptor expression and secretion of the protein in the culture medium was checked in a dot blot with anti-HIS specific antibodies (#1922416, Roche, Mannheim, Germany).

The cell clone was expanded under normal cell culture conditions and seeded in a stack of tanks. After growth under FCS for 21 days, the medium was replaced by fresh serum-free medium. After 3 days, 40 liters of serum-free cell culture supernatant were obtained. This supernatant was concentrated to one liter using a Fresenius Hemoflow F60 (factor of 40). Then 50 ml of Ni-NTA-Superflow Beads (Qiagen, Hilden), which were preequilibrated with PBS were added to the concentrate and stirred at 4° C. for 3 hours. The beads were sedimented by switching off the stirrer (overnight at 4° C.), the supernatant was discarded, and the Ni-NTA beads were packed into a column. The beads were washed with three column volume of 20 mM Na phosphate buffer, 300 mM NaCl of pH 8.0 at room temperature. Subsequent washing steps took place with 5 column volume of 20 mM Na phosphate buffer, 300 mM NaCl, 10 mM imidazoles of pH 8.0. The bound hexa-His-tagged NgR was eluted with 20 mM Na phosphate buffer, 300 mM NaCl, 100 mM imidazoles of pH 8.0. The eluate was dialyzed against 25 mM Tris/HCl pH 7.0 overnight. The dialyzate was put down to a Q-Sepharose column (Amersham Biosciences, 1.6×3 cm; Volume 6 ml) at room temperature. The following buffers were then used:
Buffer A: 50 mM Tris/HCl; pH 7.0;
Buffer B: 50 mM Tris/HCl; 1M NaCl; pH 7.0

The following gradient was used for elution at a flow rate of 2 ml/min:
0% buffer B for 5 column volume; 0-50% buffer B in 12 column volume; 50-100% buffer B in 2 column volume, and 100% buffer B in 5 column volume.

Two fractions were obtained per column volume. These were analyzed by standard SDS gel electrophoresis. Fractions with the greatest NgR purity were combined for the portion of the high-glycosylated receptor (molecular weight about 110 000-120 000) and for the portion of the low-glycosylated receptor (molecular weight about 75 000-90 000). The combined fractions were dialyzed against 20 mM Na phosphate buffer, 140 mM NaCl of pH 7.4 at 4° C. overnight. The dialyzates were then filtered through a 0.2 µm sterilizing filter and stored at 4° C.

Preparation Example 6

Preparation of a Monoclonal anti-NtermR31 Antibody

The following strategy was chosen to generate monoclonal antibodies against NtermR31. As immunogen, the peptide was conjugated to bovine thyroglobulin (BTG, Sigma, T-1001) which carries maleimide groups (derived from sulfosuccinimidyl 4-(N-maleimidomethyl)cyclohexane-1-carboxylate). To detect generated anti-peptide antibodies, the same peptide was, conjugated to bovine serum albumin (BSA, Sigma, A-7906) which likewise carries maleimide groups (derived from succinimidyl-6-[(β-maleimidopropionamido)hexanoate]) of different chemical structure. Conjugation of the same peptide to two different high molecular weight carriers via two different crosslinkers permits monoclonal antibodies for specificity against the peptide to be selected.

a) Preparation of the Immunizing Antigen

NtermR31 was conjugated to BTG using the sulfhydryl group-reactive heterobifunctional crosslinker sulfosuccinimidyl 4-(N-maleimidomethyl)-cyclohexane-1-carboxylate (sulfo-SMCC). Conjugation took place using the following two-stage method.

1. Maleylation of the Carrier Protein 4 mg of sulfo-SMCC in water (10 mg/ml) were added to 2 ml of the carrier protein solution (10 mg/ml) in HEPES-buffered saline solution (20 mM HEPES-Na, 150 mM NaCl, pH 7.5) at 4° C. The reaction mixture was incubated at 4° C. for 30 minutes and then at 25° C. for a further 30 minutes. After the incubation time the reaction mixture was desalted on a Sephadex G-50 column (1.5×14 cm) equilibrated with the same buffer. After the desalting time 8 ml of the maleylated BTG solution were obtained in a concentration of 2.5 mg/ml.

2. Coupling of Maleylated BTG to the Peptide NtermR31

1.2 ml of a solution of the peptide NtermR31 (10 mg/ml) in HEPES-buffered saline solution were added to 5 ml of the maleylated BTG solution (2.5 mg/ml) in the same buffer and incubated at 4° C. for 2 hours and then at room temperature for 4 hours. Unreacted maleimide groups were blocked with 2-mercaptoethanol in a final concentration of 10 mM and incubation overnight. This was followed by a dialysis against phosphate-buffered saline solution (PBS, 10 mM sodium phosphate, 150 mM sodium chloride, pH 7.2) at 4° C. and four buffer changes (MW exclusion 10 000).

b) Preparation of the ELISA Antigen

The peptide NtermR31 was conjugated to BSA using the sulfhydryl group-reactive heterobifunctional crosslinker succinimidyl-6-[β-maleimido-propionamido)hexanoate] (SMPH). The conjugation took place by the following two-stage method.

1. Maleylation of the Carrier Protein 4 mg of SMPH in water (10 mg/ml) were added to 2 ml of the carrier protein solution (10 mg/ml) in HEPES-buffered saline solution (20 mM HEPES-Na, 150 mM NaCl, pH 7.5) at 4° C. The reaction mixture was incubated at 4° C. for 30 minutes and then at 25° C. for a further 30 minutes. After the incubation time the reaction mixture was desalted on a Sephadex G-50 column (1.5×14 cm) equilibrated with the same buffer. After the desalting time 8 ml of the maleylated BSA solution were obtained in a concentration of 2.5 mg/ml.

2. Coupling of Maleylated BSA to NtermR31

1.2 ml of a solution of the peptide NtermR31 (10 mg/ml) in HEPES-buffered saline solution were added to 5 ml of the maleylated BSA solution (2.5 mg/ml) in the same buffer and incubated at 4° C. for 2 hours and then at room temperature for 4 hours. Unreacted maleimide groups were blocked with 2-mercaptoethanol in a final concentration of 10 mM and incubation overnight. This was followed by a dialysis against phosphate-buffered saline solution (PBS, 10 mM sodium phosphate, 150 mM sodium chloride, pH 7.2) at 4° C. and four buffer changes (MW exclusion 10 000).

c) Immunization 5 mice (8 weeks old) were treated by injection with 100 μg of BTG-peptide conjugate emulsified in complete Freud's adjuvant (Sigma, F-5881). The injection took place under the peritoneal cavity 90 days before fusion. All the other injections were administered into the peritoneal cavity according to the following scheme. Incomplete Freud's adjuvant from Sigma (catalog number F-5506) was used.

| Immunization | Days before fusion | Amount of antigen μg | Adjuvant |
|---|---|---|---|
| 1 | 90 | 100 | complete |
| 2 | 60 | 100 | incomplete |
| 3 | 30 | 100 | incomplete |
| 4 | 15 | 100 | without adjuvant |
| 5 | 7 | 200 | without adjuvant |
| 6 | 4 | 200 | without adjuvant | d) Myeloma Cell Line

The myeloma cell line used was SP2/0-Ag14 from the Deutsche Sammlung für Mikroorganismen and Zellkulturen. The cells do not synthesize or secrete any immunoglobulin chains, they are resistant to azaguanine (8-AZG, 20 μg/ml), do not grow in HAT (hypoxantine $10^{-4}$ M, aminopterin $10^{-5}$ M and thymidine $4 \times 10^{-5}$ M) medium. The SP2/0 cells were cultivated in tissue culture flasks in standard culture medium (DMEM+10% fetal calf serum (FCS) supplemented with 20 μg/ml 8-AZG in order to kill HGPRT+ revertants). One week before the fusion, the SP2/0 cells were maintained in standard culture medium without 8-AZG.

e) Cell Fusion and Plating

Three spleen organs from immunized mice were removed and comminuted aseptically. Single-cell suspensions were prepared therefrom. The spleen lymphocytes were fused to the SP2/0 myeloma cell line (ratio: 5 lymphocytes/1 SP2/0) in the presence of polyethylene glycol 3350. The cells produced in this way were resuspended in DMEM comprising HAT and 20% FCS. The cells were plated out in eight 96-well tissue culture plates (Corning Costar) which comprised cells from peritoneal exudate as feeder layer. The plates were incubated in a moist atmosphere comprising 5% carbon dioxide at 37° C. for 10 days. During this period, the cells were fed twice with HAT medium.

A part of the spleen cell suspension was cultivated in a T flask for 10 days.

f) Screening Assay

An indirect ELISA designed to detect IgG was employed to screen the cell culture supernatants. The assays were carried out in flat-bottomed polystyrene microtiter plates with 96 wells (Greiner, Cat. #756071) as follows: 100 μl aliquots of a solution of 0.5 M carbonate/bicarbonate buffer, pH 9.6, comprising 4 μg/ml BSA-NtermR31 conjugate (based on BSA) was added to each well of the plate. After incubation in a humidity chamber at 4° C. overnight, the plates were washed four times with tris-buffered saline solution (TBS, 50 mM Tris, 500 mM NaCl, pH 7.8) comprising 0.01% Triton X-100 (washing buffer), and blocked with 200 μl/well of 2% strength gelatin (from cold water fish skin, Sigma G-7765) in TBS (blocking buffer) at room temperature (RT) for 1 hour. The plates were washed with washing buffer, and 100 μl of cell culture supernatant was added to each of the wells. The cell culture supernatant from SP2/0 myeloma cells was used as negative control. The splenocyte cells culture supernatant was used as positive control.

The plates were incubated at room temperature for 1 hour. After several washing steps, the ELISA plates were incubated with goat anti-mouse IgG (mouse Fc-specific) conjugated to alkaline phosphatase (Sigma, A-2429) (50 μl/well, diluted in blocking buffer, 1:5000) at room temperature for 1 hour. After a further washing step, 150 μl/well of substrate buffer (2 mM 4-nitrophenyl phosphate (SIGMA, N3254) in 5% diethanolamine+0.5 mM $MgCl_2$, pH 9.8) was added to the plates. The substrate conversion was detected in a 12-channel Dynex Opsys MR microplate reader at a wavelength of 405 nm.

g) Selection of Stable Antibody Produced

The first screening was carried out 10 days after the fusion. Cells from positive IgG-producing wells were transferred into wells of plates with 24 wells and cultivated for 4 days. An ELISA for BSA-NtermR31 was carried out to determine cultures which produce the antibody of interest. This expansion process was repeated twice after 3 and after 5 days. Thus, inter alia, an anti-NtermR31 Ab with the internal name "Clone 37" was isolated.

h) Cryopreservation of the Hybridoma Cells

An aliquot of each of the hybridomas was resuspended in 1.0 ml of cryomedium (90% (v/v) FCS, 10% (v/v) dimethyl sulfoxide) and transferred into freezing tubes. The vessels were then immediately transferred into a cooling chamber (cooling rate 1° C. per minute). After a temperature below −60° C. was reached, the cells were transferred into liquid nitrogen for storage.

III. Exemplary Embodiments

Exemplary Embodiment 1

Figure 5:
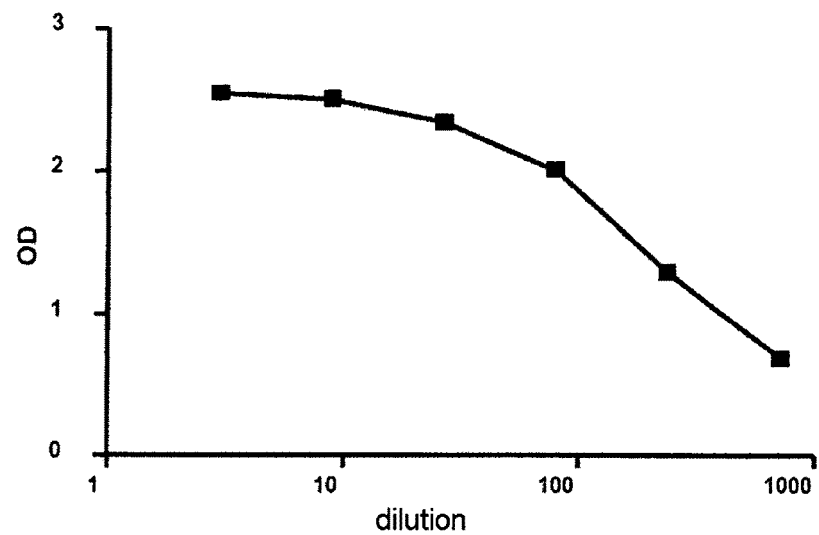
FIG. 5 shows the result of an ELISA with which serum of immunized rabbit antibodies against the N-terminal peptide NtermR31 were detected.
Figure 6:
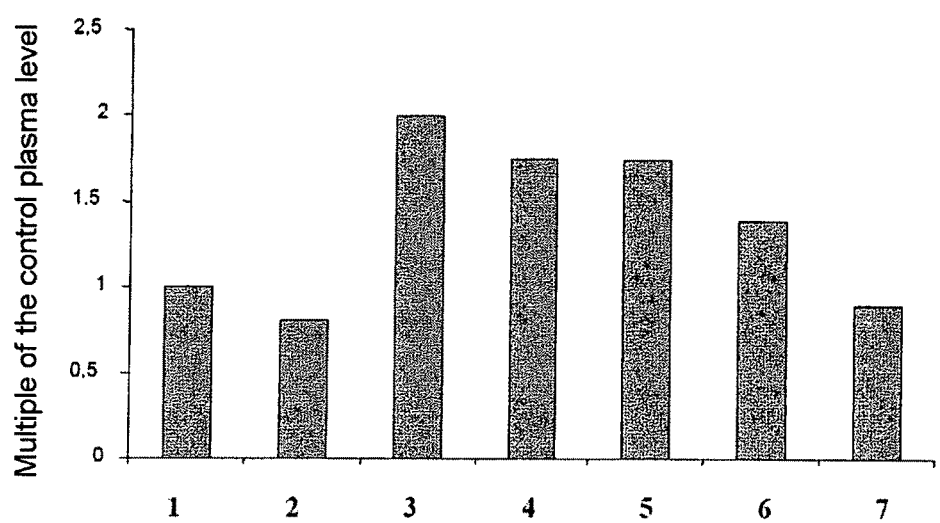
FIG. 6 shows the result of an ELISA with which the relative amount of antibodies against NtermR31 in various patients' plasmas was detected. 1: healthy control; 2: AP23, MCIF06.7, F; 3: LAP30, Alzheimer Dementia, F00.0, early onset, F; 4: LAP39, MCIF06.7, F; 5: LAP45, MCIF06.7, M; 6: LAP53, MCIF06.7, F; 7: LAP60, Alzheimer Dementia, late onset, M.

ELISA Measurement of Autoantibodies Against the N-terminal Peptide NtermR 31 of sRAGE in Human Plasma a) Materials:
  Microtiter plates: SigmaScreen; Streptavidin Coated Plate (Sigma, M-4058; 96-well (black));
  Nterm 31 (SEQ ID NO:6) (comprising 31 N-terminal amino acids of the mature RAGE without Leader-Peptid), biotinylated by Thermo Electron GmbH; Ulm; OR183539/2), dissolved, 3.9 mg/ml; further diluted for use to 1 µg/ml in TBS, 0.1% Tween20; 0.1% BSA
  Washing buffer: TBS 0.1% Tween20
  TBS, Tris buffered Saline,: 20 mM Tris pH 7.4; 0.9% NaCl
  Substrate: 4-nitrophenyl phosphate: from Roche; No. 726923; one tablet dissolved in 100 ml of 100 mM Tris/HCl of pH 9.8
  Antibodies:
    Goat anti-rabbit IgG (whole molecule), conjugated to alkaline phosphatase (AP conjugate); Sigma A-3812; dilution in the ELISA 1:5000 in TBS 0.1% Tween20; 0.1% BSA
    Goat anti-human IgG (Fc specific); conjugated to alkaline phosphatase (AP conjugate); Sigma A-9544, dilution in the ELISA 1:5000 in TBS 0.1% Tween20; 0.1% BSA
    Polyclonal antiserum from a rabbit which had been immunized several times with the peptide=anti-31mer-8508; (animal 6304), 20 ml of 8.6.2004; mixed with 0.02% thimerosal (rabbit polyclonal AB 1:500); the immunization and obtaining of the serum were carried out by BioTrend (Cologne, Germany). Plasmas from patients with Alzheimer's Dementia (AD) were obtained from Prof. Henn (Zentralinstitut für die seelische Gesundheit, Mannheim):
      Non AD control; female: control plasma;
      Plasmas from patients: AP23 MCIF06.7 female; LAP30 Alzheimer Dementia female 00.0 early onset; LAP39 MCI F06.7 female; LAP45 MCI F06.7 male; LAP53 MCI F06.7 female; LAP60 Alzheimer Dementia late onset male.
    The samples were further diluted in the ELISA in TBS 0.1% Tween20; 0.1% BSA b) Test Procedure:
  100 µl portions of the diluted NtermR31 peptide were pipetted into each well of the microtiter plate. This was followed by incubation at room temperature for 2 hours. The supernatant was discarded, and the plates were each washed three times with washing buffer. 100 µl portions of the rabbit serum (positive control) or of the various plasmas were incubated in each well in the plates in various dilutions at room temperature for 3 hours in each case. The supernatant was discarded, and the plates were each washed three times with washing buffer. Then 100 µl portions of the appropriate enzyme-labeled antibodies (anti-human for the human plasma samples; anti-rabbit for the rabbit antiserum) were pipetted in each case into each well and incubated at room temperature for 1 hour. Each was then again washed three times with washing buffer. Each well then comprised 100 µl of the substrate solution. After a development time of about 10 minutes, the enzyme reaction was stopped by adding 50 µl of 1 M NaOH per well. The liquid from the wells was transferred into a transparent microtiter plate (flexible plate; Falcon No. 353912). The absorption in the wells of the microtiter plate was measured in an appropriate photometer at 405 nm.

c) Results:
  Antibodies against the N-terminal peptide were detectable with the aid of this ELISA in the serum of the immunized rabbit (cf. FIG. 5). The ELISA is therefore suitable for detecting antibodies against the N-terminal peptide NtermR31 of human RAGE.
  The results obtained with various patients' sera are depicted in FIG. 6. The ratio of the absorptions at a 1:3 dilution of the plasmas is shown. The plasma of Alzheimer's patients with an early onset shows a doubling of the reaction. Accordingly, distinctly more antibodies against the N-terminal RAGE peptide NtermR31 are detectable in this plasma.

Exemplary Embodiment 2

Figure 7A:
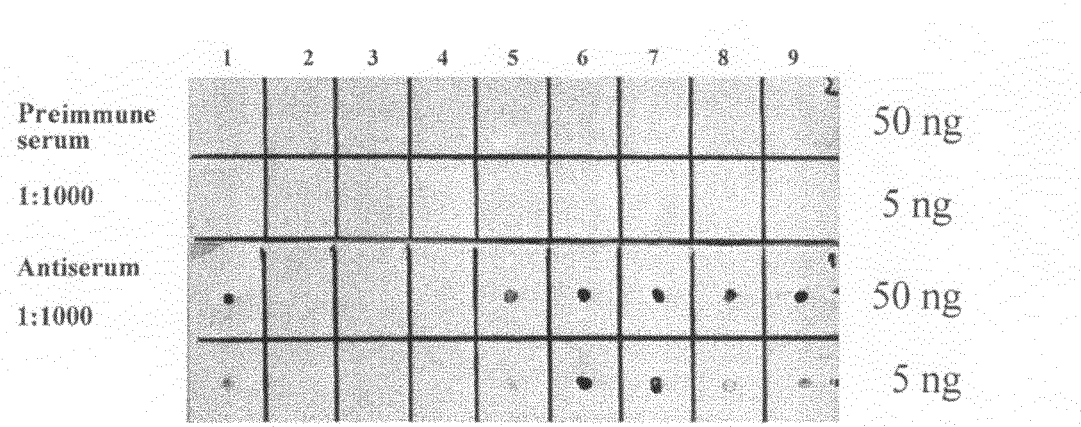
FIG. 7a shows the result of a dot-blot method to characterize the polyclonal anti-NtermR31 serum (lower half) with various peptides and sRAGE forms produced according to the invention. The upper half shows corresponding control mixtures with preimmune serum. Description of the mixtures: 1: NtermR31; 2: ScraNtermR31; 3: ScraNtermR13; 4: NtermR13; 5: sRAGE-6×HIS (AA23-352, NP-001127); 6: human sRAGE/Fc (R&D Systems; #1145-RG; AA 1-344); 7: human sRAGE/Fc (1-130AA); 8: mouse sRAGE (R&D Systems; # Custom03); 9: rat sRAGE/Fc (R&D Systems; #1616-

Characterization of the Polyclonal Anti-NtermR31 Serum and of a Monoclonal Anti-NtermR31 Antibody a) Materials
  Nitrocellulose membranes (0.45 µm pore size, # LC2001, from Invitrogen)
  Blocking reagent (Roche Applied Science; #1921673)
  NBT/BCIP solution (1 tablet in 10 ml of $H_2O$; Roche Applied Science, #1697 471)
  Protein/peptide samples
  NtermR31 (see above)
  ScraNtermR31 (see above)
  ScraNtermR13 (see above)NtermR13 (see above)sRAGE-6xHIS (AA 23-352,
  NP_001127)human sRAGE/Fc (R&D Systems; #1145—RG; AA 1-344)
  human sRAGE/Fc (AA 1-130)
  mouse sRAGE (R&D Systems; # Custom03)
  rat sRAGE/Fc (R&D Systems; #1616—RG; AA 1-342)
  Antibodies
  polyclonal anti-NtermR31 serum and preimmune serum purchased through Biotrend (Cologne, Germany) (cf. Exemplary embodiment 1),
  secondary antibody ShpxRb IgG AlkPhos (Chemikon, # AP304A)

b) Test Procedure for Polyclonal Serum:
  The characterization of the polyclonal anti-NtermR31 serum was carried out with the aid of a dot blot method. 5 or 50 ng of the protein or peptide samples listed above were loaded in a volume of 0.5 µl onto nitrocellulose membranes. The membrane was blocked in 1x blocking reagent at 4° C. overnight. The membranes were then incubated with preimmune serum and antiserum NtermR31 from rabbit 6304 in a dilution of 1:1000 in 0.5% blocking reagent for one hour. Three washing steps in 1xPBS at room temperature were followed by incubation with the secondary antibody ShpxRb IgG AlkPhos at room temperature in 0.5% blocking reagent for one hour. The membrane was again washed in PBS for 3x5 minutes before being stained with NBT/BCIP solution. The staining solution was aspirated off after the desired signal/background ratio was reached, and the membranes were rinsed with water.

c) Results for Polyclonal Serum:
  The test result is depicted in FIG. 7a). The polyclonal anti-NtermR31 antiserum recognizes, as was to be expected, the peptide NtermR31 in the dot blot which was carried out. The proteins sRAGE-6xHIS (AA 23-352, NP_001127), human sRAGE/Fc (R&D Systems; #1145—RG) and human sRAGE/Fc (1-130 AA) are also recognized with high sensitivity, as demonstrated by staining of 5 ng portions of protein. These proteins each comprise the complete partial sequence of NtermR31 at the N-terminal part, so that the result again corresponds to expectation. The highly conserved mouse and rate RAGE proteins were likewise distinctly recognized, so that a cross-reactivity with mouse and rat RAGE can be ascribed to this antiserum.

A surprising finding is the poor or absent detection of the peptide in NtermR13 that is a partial sequence (core sequence) of NtermR31 and shows substantial binding activity in the homogeneous binding assay (AlphaScreen; cf. below). A probable explanation of this result might be the preferred recognition of a conformational epitope in NtermR31 by the polyclonal antibody. Only if the peptide assumes this confirmation through intramolecular interaction is it clearly recognized by the antiserum. The shorter NtermR13 partial peptide cannot assume this spatial structure and is therefore not recognized. The complete sequence comprising 31 amino acids or peptides which comprise this sequence are therefore particularly suitable as immunogen.

A further possible explanation might be a clearly different immunogenicity of the peptide NtermR13 compared with the non-overlapping regions of NtermR31 (region 1-14; region 28-31). Analysis of the peptide sequence with the Abie Pro 3.0 software package (ChangBioscience.com) which is employed to select antigenic peptide sequences for antibody production is, however, contradictory to this explanation. Analysis of NtermR31 with Abie Pro 3.0 shows that four 13-mer peptides with good antigenic properties are predicted, with one peptide correspondingly exactly to the sequence NtermR13. The three other peptides are each N-terminally displaced by one amino acid, so that there is great overlap with NtermR13 in each of these cases. A markedly weaker immunogenicity of NtermR13 is therefore rather unlikely, and the hypothesis of the 3D conformation is to be regarded as the probable one. This conformation likewise cannot be assumed by the scrambled peptides, which explains their non-recognition in Western dot blot.

d) Test Procedure for Monoclonal Anti-NtermR31 Antibody

Figure 7B:
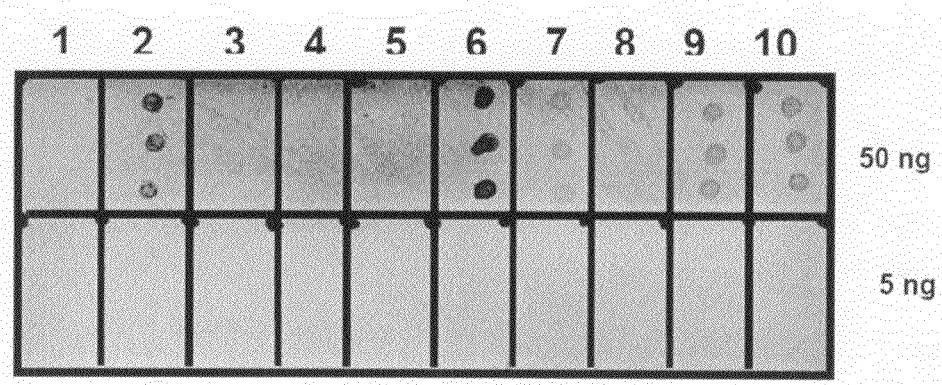
FIG. 7b shows the result of corresponding experiments with monoclonal anti-NtermR31 antibody "clone 37". Description of the mixtures: 1: NtermR13; 2: NtermR31; 3: ScraNtermR13; 4: ScraNtermR31; 5: N/C truncated(sRAGE-6×HIS) (AA 102-352, NP_001127); 6: human sRAGE/Fc (AA 1-130); 7: human sRAGE/Fc (R&D Systems; #1145-RG; AA 1-344); 8: human sRAGE-6×HIS (AA 23-352, NP_001127); 9: mouse sRAGE (R&D Systems; # Custom03); 10: rat sRAGE/Fc (R&D Systems; #1616-RG; AA 1-342)).

Characterization of the monoclonal anti NtermR31 antibody from the cell culture supernatant of clone 37 was carried out with the aid of a dot-blot method. 5 or 50 ng of the protein or peptide samples listed above were loaded in triplicate in a volume of 0.5 µl onto nitrocellulose membranes (0.45 µm pore size, # LC2001, from Invitrogen). The membrane was blocked in 1× blocking reagent (Roche Applied Science; #1921673) at 4° C. overnight. The membranes were then incubated with cell culture supernatant purchased through Biotrend (Cologne, Germany) in a dilution of 1:10 in 0.5% blocking reagent (Roche Applied Science; #1921673) for one hour. Three washing steps in 1×PBS at room temperature were followed by incubation with the secondary antibody Shp×Ms IgG F(ab')2 AP (Chemikon, # AQ330A) at room temperature in a 1:5000 dilution in 0.5% blocking reagent for one hour. The membrane was again washed in PBS for 3×5 minutes before being stained with NBT/BCIP solution (1 tablet in 10 ml of $H_2O$; Roche Applied Science, #1697 471). The staining solution was aspirated off after the desired signal/background ratio was reached, and the membranes were rinsed with water.

e) Results for Monoclonal Antibody:

The results are depicted in FIG. 7 *b*. This shows that the specificity of anti-NtermR31 mAb is comparable with polyclonal rabbit antiserum (recognition of NtermR31, no reaction to scrambled controls and NtermR13, and species cross-reaction between human, rat, mouse).

Exemplary Embodiment 3

AlphaScreen Measurement of the sRAGE Interaction with the Peptides NtermR31 and NtermR13 a) Materials

The binding of NtermR31 or NtermR13 to the RAGE receptor was measured by employing the AlphaScreen™ System (order number: 6760610M) from Perkin Elmer (Shelton, Conn., USA).
NtermR13 biotinylated (Thermo Electron, Ulm)
NtermR31 biotinylated (Thermo Electron, Ulm)

b) Test Procedure

The entire homogeneous assay was carried out in 25 mM HEPES, 100 mM NaCl of pH 7.4 and 0.1% BSA in a volume of 20 µl. The mixture comprised 2.5 ng/µl of the fusion protein sRAGE-6×HIS (amino acids 23-352, NP_001127), 20 ng/µl of anti-HIS acceptor beads, 20 ng/µl streptavidin donor beads and NtermR13 or NtermR31 peptides in the concentrations of 0, 1, 5, 10, 25, 50, 100, 150 and 300 nM.

The individual components were brought together in a defined time sequence. Initially sRAGE 6×HIS was incubated with the acceptor beads for 30 minutes. The various amounts of peptide were then added in order, after a further 30 minutes, to add the donor beads. After a further 60 minutes, the fluorescence was measured in the AlphaQuest instrument from Perkin-Elmer with a time lag of one second. Each measured point was determined as triplicate. The analysis and graphical workup of the results took place with the GraphPrism 4.0 software package.

c) Results

Figure 8:
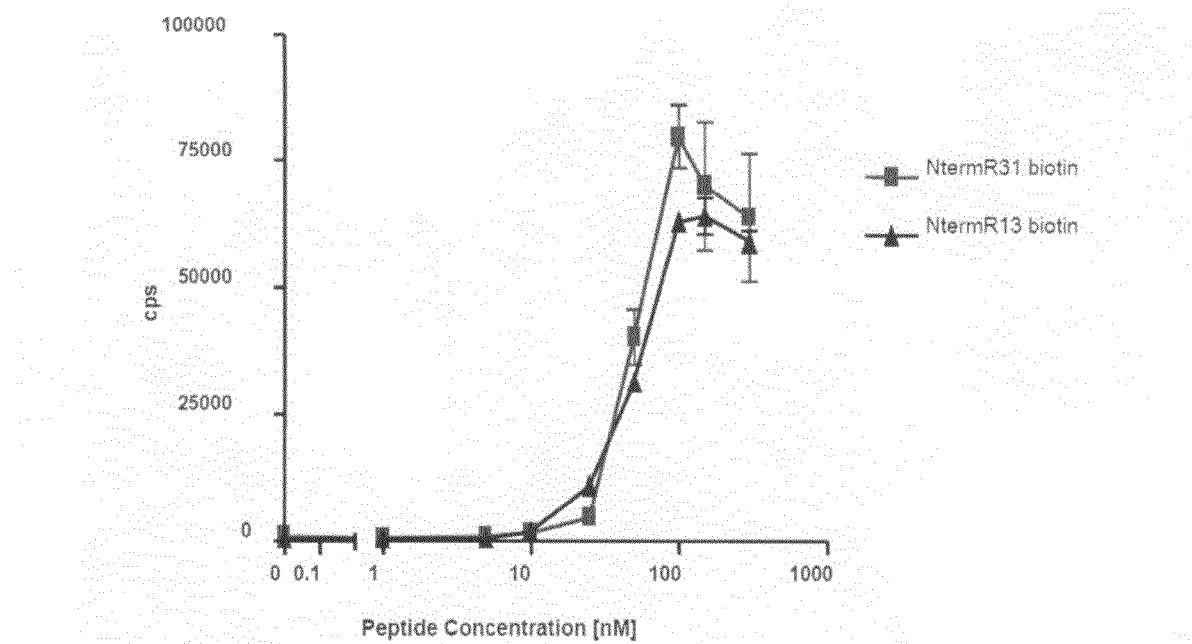
FIG. 8 shows the binding of NtermR31 and NtermR13 to sRAGE in the AlphaScreen assay as a function of the peptide concentration employed.

The results are depicted in FIG. 8. The peptides NtermR31 and NtermR13 bind with high affinity to sRAGE protein in the test described herein. The $EC_{50}$ values found in the AlphaScreen binding assay are respectively 62 and 66 nM.

Exemplary Embodiment 4

AlphaScreen Measurement of the sRAGE Interaction with Control Peptides a) Materials The binding to the RAGE receptor was measured by employing the AlphaScreen™ System (order number: 6760610M) from Perkin Elmer (Shelton, Conn., USA).

The following peptides were employed in biotinylated form:
Amyloid Aβ-1-42 oligomer (prepared as disclosed in WO 2004 067561)
Scrambled NtermR13: G K P R A P K C L K P E Q
NtermR13: C K G A P KK P P Q R L E
AlterCharge1: F S R I R A T H W R V D G
Non-polar: F P V I P A L F W I V L M
Plus7: R L KR G H A
Minus7: E T E D S D T
Underlined: positively charged amino acids
Italic: negatively charged amino acid b) Test procedure The assay was carried out by the manufacturer's protocol in 25 mM HEPES, 100 mM NaCl of pH 7.4 and 0.1% BSA in a volume of 20 µl. The mixture comprised 2.5 ng/µl of the fusion protein sRAGE-6×HIS (amino acids 23-352, NP_001127), 20 ng/µl anti-HIS acceptor beads, 20 ng/µl streptavidin donor beads and the biotinylated peptides in concentrations of 0, 10, 30, 100, and 300 nM. The peptides, with the exception of Aβ 1-42 oligomers, were heated at 50° C. for 10 minutes immediately before the test in order to loosen possible aggregations.

Figure 9:
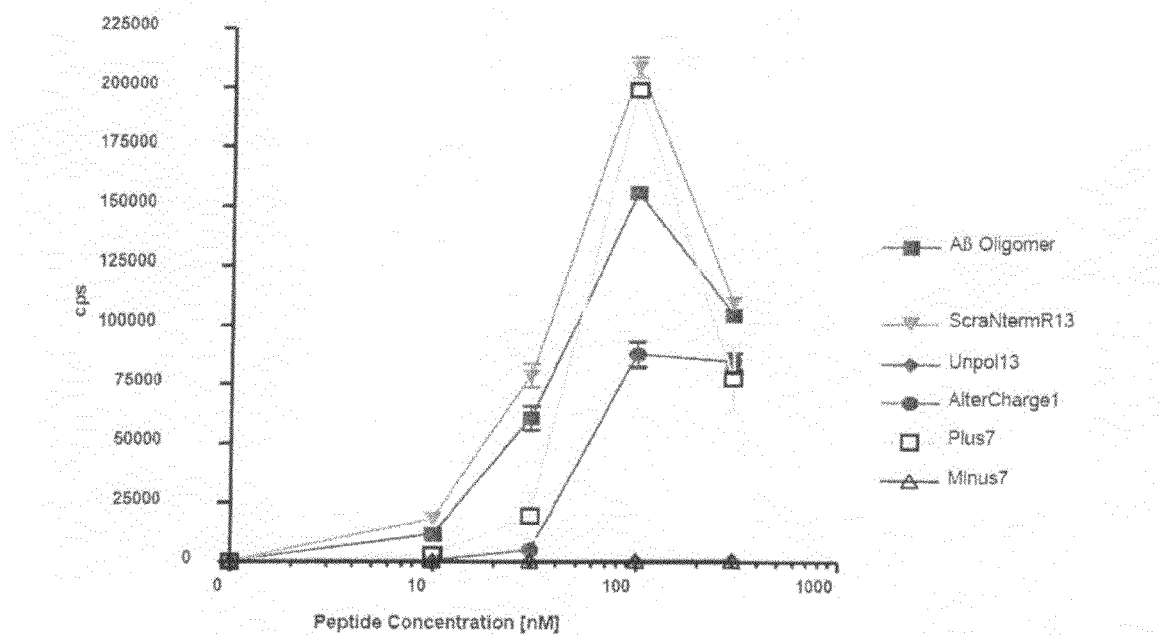
FIG. 9 shows the binding of various control peptides to sRAGE in the AlphaScreen assay as a function of the peptide concentration.

The individual components were brought together in a defined time sequence. Firstly, sRAGE 6×HIS was incubated with the acceptor beads for 30 minutes. The various amounts of peptide were then added in order, after a further 30 minutes, to add the donor beads. After a further 60 minutes, the fluorescence was measured in the AlphaQuest instrument from Perkin-Elmer with a time lag of one second. Each measured point was determined as triplicate. The evaluation and graphical workup of the results took place with the GraphPrism 4.0 software package.

c) Results:

The test results are depicted in FIG. 9. The control peptides employed in this test are intended to elucidate the nature of the binding of NtermR31 and NtermR13 to RAGE. The binding of Aβ oligomer to RAGE served as positive control.

Both the completely nonpolar and neutral peptide "Unpol13" and the negatively charged peptide "Minus7" show no bonding to the receptor in the experiment, as demonstrated by the low, scarcely visible curves for these peptides (running on the X axis). The hypothesis that positive charges are necessary for the binding is impressively confirmed by the peptides "ScraNtermR13", "AlterCharge1" and "Plus7". The highest charge density is possessed by the Heptamer Plus7, which, together with ScraNtermR13, reaches the highest maximum signal intensity in the test. ScraNtermR13 is composed of the same amino acids as NtermR13 but in arbitrary sequence. Since the control binds with the same or slightly higher affinity to sRAGE, the amino acid sequence is, according to the data currently available, of relevance only to the extent that positive charges must be present in a particular density. The fact that not even the specific combination of positive charge carriers is necessary for the binding is demonstrated by the peptide AlterCharge1, which as 13mer has four positive charges which, however, are derived from three arginines and one histidine, not from 3 lysines and one arginine as in the case of NtermR13.

In summary, it can be stated that ionic peptide/receptor interactions via positive charges in the peptide NtermR13 are evidently sufficient for binding to RAGE. Such positive charge aggregations are, however, particularly involved in the binding process only if they are presented in a relatively large polypeptide by means of a particular 3D folding on the surface of a polypeptide/protein, e.g. sRAGE.

Exemplary Embodiment 5

AP-Nogo66 Competition Assay a) Materials:
Microtiter plates (Maxisorb, Nunc)
AttoPhos substrate (Roche No. 1681982, Germany)
His-NogoR: expressed in CHO-K1 cells and after purification with a purity of >90% of the low-glycosylated Nogo receptor with a molecular weight of 80 kDa in SDS-PAGE
AP-Nogo66 (see above)
sRAGE (see above)
Nterm 31 (see above)
NtermR13 (see above)
scraNtermR13 (see above)
scraNtermR31 (see above)
b) Test Procedure:
Microtiter plates (Nunc Maxisorb) were coated with 0.1 ml of a solution of His-NogoR (5 µg/ml in sodium carbonate buffer, pH 9) at 4° C. overnight. This was followed by a blocking step for 1 hour with 2% strength bovine serum albumin (BSA) in Tris-HCl, pH 7.2, at room temperature. Solutions of His-NogoR, sRAGE and NtermR31 were adjusted to initial concentrations of 200 nM. These stock solutions were then diluted three-fold. AP-Nogo66 (3 µg/ml) was diluted to 0.2 nM with buffer (Tris-HCl, pH 7.2 and 0.1% BSA). 0.05 ml of AP-Nogo66 (0.2 nM) was added to the respective dilutions of the proteins (0.05 ml) and incubated at ambient temperature for 90 minutes. The respective final concentrations were: 0.1 nM for AP-Nogo66 and 100, 33.3, 11.1, 3.7, and 1.2 nM for His-NogoR, sRAGE and NtermR31.

After each incubation step, the plates were washed with washing buffer (10 mM Tris-HCl, pH 7.2 and 0.05% Tween20). The binding of AP-Nogo66 was detected using the substrate AttoPhos (Roche) for alkaline phosphatase, and the fluorescence units were measured using the Polarstar instrument (BMG Labtech, Germany). The results are depicted for the proteins in FIG. 10A and for the peptide Nterm 31 in FIG. 10B.

c) Results:

The binding of AP-Nogo66 to the NgR which was bound to the microtiter plate was blocked by the same soluble ligands with an $IC_{50}$ of 2 nM. Surprisingly, the sRAGE protein blocks the AP-Nogo66 binding in a similar concentration range with an $IC_{50}$ of 3.5 nM (FIG. 10A). Significant blocking of the binding of AP-Nogo66 was also found with the peptide NtermR31 ($IC_{50}$ of 50 nM) (FIG. 10B).

Exemplary Embodiment 6

Figure 11:
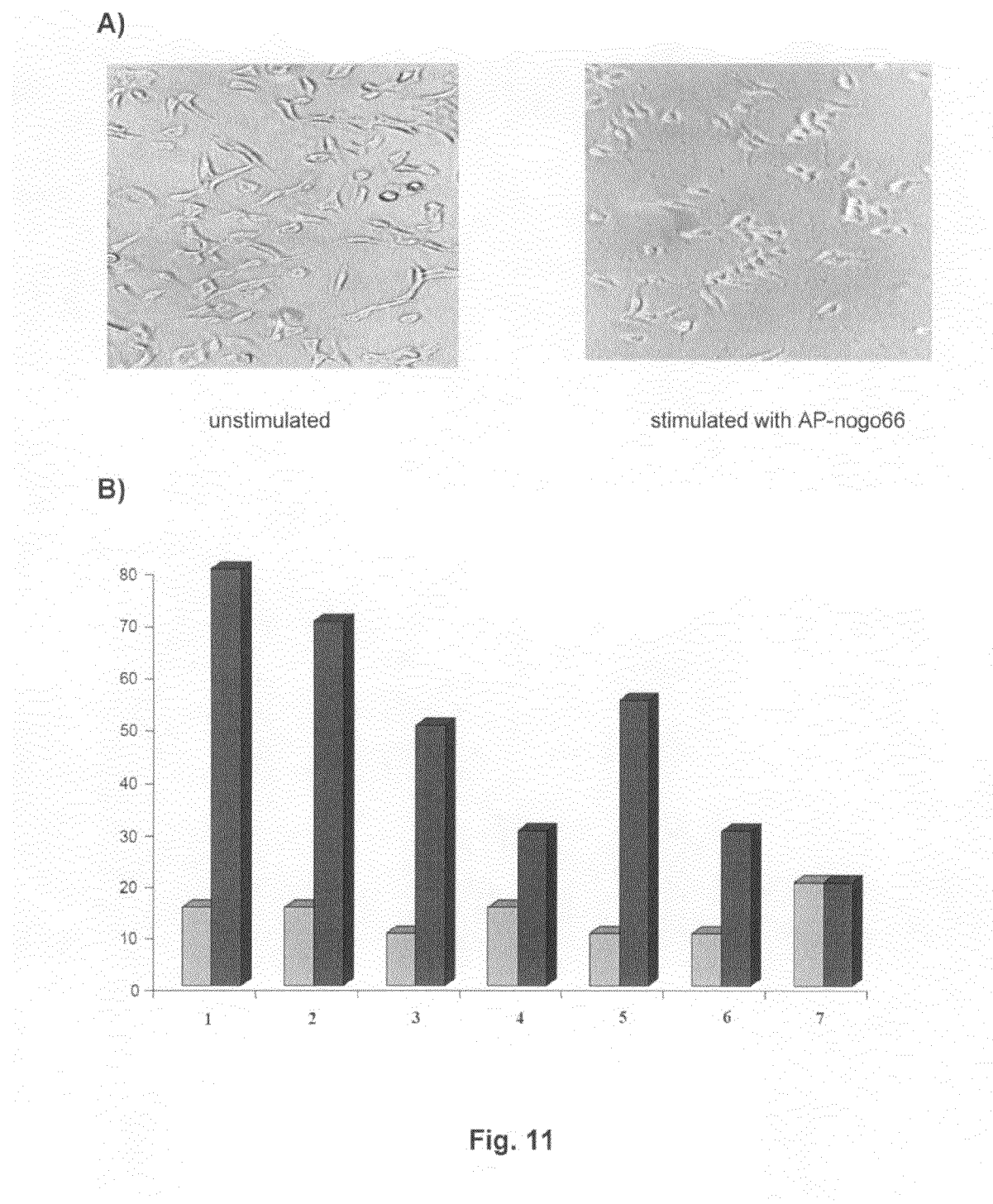
FIG. 11A shows micrographs of unstimulated and AP-Nogo66-stimulated HEK293 RhoA/NgR/p75 cells. Stimulation with AP-Nogo66 is observed to be followed by a marked change in the cell geometry through contraction.
FIG. 11B shows the concentration-dependent reduction in the percentage content of contracted HEK cells with various concentrations of NtermR31 and sRAGE. The paler, left-hand bar in each pair of bars shows the result of the experiment for the respectively assigned, unstimulated control mixture (without AP-Nogo66). Description of lines 1 to 7: 1: no treatment; 2: NtermR31 (0.2 µM); 3: NtermR31 (1 µM); 4:NtermR31 (5 µM); 5: sRAGE (0.2 µM); 6: sRAGE (1 µM); 7: sRAGE (5 µM).

Functional Cytoskeletal Rearrangement (ACR) Assay a) Materials:
Hek293 RhoA/NgR/p75 (see above)
NtermR13 (see above)
NtermR31 (see above)
sRAGE (see above)
AP-Nogo66 (see above)
Amphoterin scr; (Thermo Electron, Ulm, DE) ($NH_2$Cys(DY555)KSKKVEAVKKAKAGGKPKDRAAY-AKEYIDKLEKK-COOH)
MTP Biocoat microtiter plates with 96 wells
RPMI-Glutamax (Invitrogen)
Phalloidin Alexa 568 or 488 (Molecular Probes, Eugene, USA)
DAPI (Molecular Probes, Eugene, USA)
b) Test Procedure:

$1\times10^4$ Hek293 RhoA/NgR/p75 cells were transferred into MTP Biocoat microtiter plates with 96 wells two days before the actual start of the test. The cell lines obtained in this way were preincubated with the respective RAGE peptide (NtermR13, NtermR31, sRAGE) in various concentrations (0.2 µM, 1 µM, 5 µM) or with a control peptide (amphoterin scr; conc.=0.2, 1, 5 µM). The cells were stimulated with the NgR ligand AP-Nogo-66 (9.6 µg/ml) in culture medium comprising 5% FCS. An unstimulated control mixture (without AP-Nogo66) was prepared for each series of tests. After a stimulation period of 5 to 10 minutes, the activation was stopped with cold PBS. The cells were fixed with 3-4% strength paraformaldehyde solution, permeabilised with PBS comprising 0.2% Triton X-100, and incubated with Phalloidin Alexa 568 or 488 for 30-45 minutes. Incubation with DAPI for nuclear staining was additionally carried out for 5 minutes. The cells were visualized with the aid of an epifluorescence microscope (Axiovert 25). Fluorescence micrograms were recorded with a cooled CCD camera from Zeiss, and the percentage content of contracted cells, based on the total cell count, was found.

c) Results:

The test results for NtermR 31 and sRAGE are depicted in FIG. 11B. A concentration-dependent reduction in the percentage content of contracted HEK cells is observed for both peptides. This shows that NtermR 31 and sRAGE increasingly diminish the NgR-dependent stimulation of cell contraction of HEK cells with increasing concentration, i.e. block the binding of Nogo-66 to its receptor NgR. FIG. 11A shows micrographs of unstimulated and AP-Nogo66-stimulated HEK293 RhoA/NgR/p75 cells. The increased content of contracted HEK cells after stimulation with AP-Nogo-66 is distinctly evident.

Exemplary Embodiment 7

FIHC Analysis with Anti-RAGE in Transgenic APP Mouse Brain a) Materials
TBST washing solution (Tris-buffered saline solution with Tween 20, 10× concentrate; DakoCytomation; Glostrup, Denmark S3306) diluted 1:10 with distilled water.
Donkey serum (Serotec GmbH, Düsseldorf, DE) 5% in TBST
Primary Antibodies:
 Rabbit anti-RAGE (Abcam, Distributor: Acris GmbH, Hiddenhaus, DE,; ab3611) diluted 1:200 in TBST
 Rabbit anti-RAGE (Biotrend; Cologne, DE; anti-31-mer-8508), diluted 1:200 in TBST; anti-NtermR31 serum of the invention;
Secondary Antibodies:
 Donkey anti-rabbit Cy3 (Jackson Immuno, Distributor Dianova GmbH, Hamburg, DE), diluted 1:500 with TBST
Vectashield hardset mounting medium (Vector Laboratories; Burlingame, UK H-1400)
 Tg2576 mice (Taconic M&B A/S, Ry, Denmark) which harbor the gene for human amyloid precursor protein (APP)
b) Test Procedure:

Frozen sections with a thickness of 40 µm made from the gyrus dentatus of Tg2576 mice with an age of 10 weeks or 11 months were incubated with donkey serum for 20 minutes and with one of the primary antibodies overnight. After 3 washing steps in TBST buffer, the sections were incubated with donkey anti-rabbit Cy3 secondary antibody for 60 minutes and finally washed three times with TBST buffer. The sections were then put onto Superfrost Plus glass slides, air-dried and covered with a cover slip. Fluorescence images of the thin sections were analyzed in an Axioplan Imaging System (Mikroskop Axioplan Imaging 2; Carl Zeiss, Jena, Germany).

c) Results:

The test results are depicted in appended FIG. 12.

APP transgenic mice show an enormous stimulation of membrane-bound RAGE at a time when amyloid plaques have not yet formed. If there is pronounced formation of amyloid, and plaques are produced (from month 9-12 of life), membrane-bound RAGE disappears in favor of soluble RAGE, which can be measured in the plasma. Older animals therefore have particularly high sRAGE plasma levels.

Figure 12B:
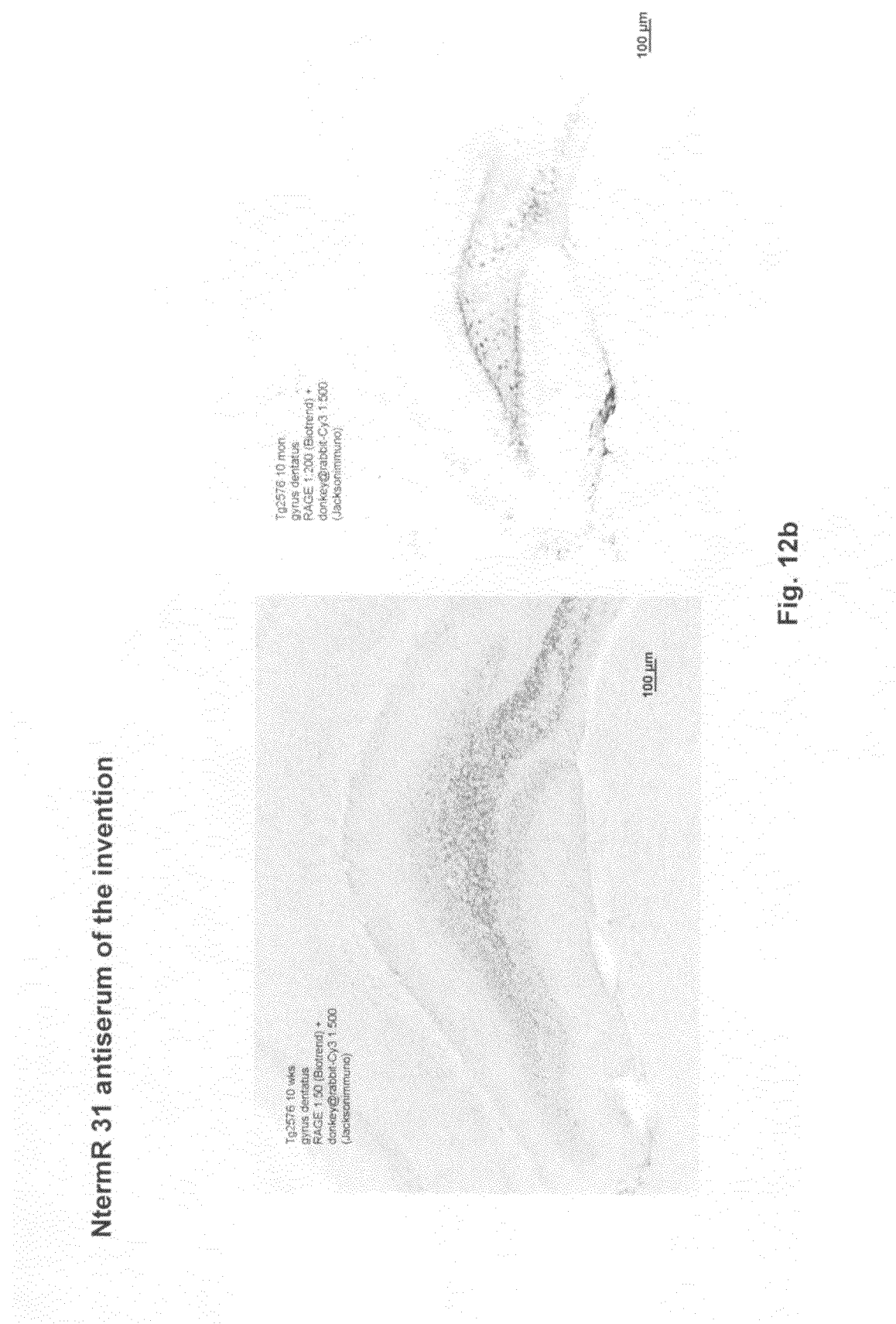
FIG. 12b shows by contrast that NtermR31 antiserum according to the invention ("Biotrend") does not stain in the young animal (10 weeks) (left-hand picture), but does with a similar pattern as commercial antiserum in the old animal (10 months) (right-hand picture).

Immunohistochemistry provides further evidence of the fact that anti-NtermR31 antiserum (FIG. 12b) is distinct from commercial anti-RAGE antisera such as the Abcam serum (FIG. 12a). The fact that the anti-NtermR31 antiserum does not stain on young Tg2576 animals in contrast to Abcam antiserum, but shows a comparable staining with the old animals, can be interpreted to mean that the epitope of AGER-RME is efficiently presented and accessible to antibodies only in the case of bound ligand (i.e. amyloid beta in the case of Tg2576). However, not much amyloid beta has yet been formed in young Tg2576. According to the literature (Ujiie M et al.: Microcirculation. 2003 December; 10(6):463-70) the animals start to form Alzheimer plaques only from 10 months onwards, indicating an increased amyloid formation only at later times and thus supporting the hypothesis of the invention concerning the immunogenicity of the AGER-RME.

Exemplary Embodiment 8

Detection of sRAGE in Mouse Plasma by ELISA a) Material
Microtiter plates (flexible plate, 96 well, flat bottom, Falcon)
Goat anti-mouse RAGE antibody; R&D Systems; AF1179
Transgenic mice (Tg2576)
Streptavidin-AP Conjugate (Roche, Mannheim, No. 1089161
AttoPhos Substrate Set (Roche, Mannheim, No. 1681982)
Recombinant soluble mouse RAGE (R&D Systems, Wiesbaden; Custom03)
b) Test Procedure:

Microtiter plates were coated with in each case 100 µl of antibody solution (goat anti-mouse RAGE; stock solution: 100 µg/ml; employed diluted in a concentration of 1 µg/ml in 50 mM $NaHCO_3$) at 4° C. overnight. The wells were then each washed three times with TBS/0.1% Tween 20. Adsorption effects were minimized by incubation with in each case 100 ml of a 1% BSA solution in TBS/0.1% Tween20 at room temperature for one hour. This was followed by washing as described above in each case three times with TBS/0.1% Tween 20.

Plasma from 10-week and 12-month old transgenic mice (Tg2576) and from mice of the non-transgenic strain C57Bl6 were employed as samples for soluble mouse RAGE. The plasma was employed in a dilution of 1:20 in TBS/01% Tween 20 in a volume of 100 µl in each case. Each was then washed three times as described above. As detection antibody, in each case 100 µl of a biotinylated goat anti-mouse RAGE antibody (stock solution: 50 µg/ml in TBS/0.1% BSA; employed diluted in a dilution of 1:200 in TBS/0.1% Tween20/0.1% BSA) was added to each well. Incubation at room temperature for 60 minutes was followed by renewed washing (as above). This was followed by incubation with in each case 100 µl of streptavidin-AP conjugate in a dilution of 1:2500 in TBS/0.1% BSA/0.1% Tween20 for 2 hours. Three washes were again carried out. The amount of enzyme was detected with the aid of 100 µl portions of the AttoPhos Substrate Set. After incubation for 90 minutes, the fluorescence was measured in a Polarstar instrument with excitation at 440 nm and emission at 540 nm.

Figure 13:
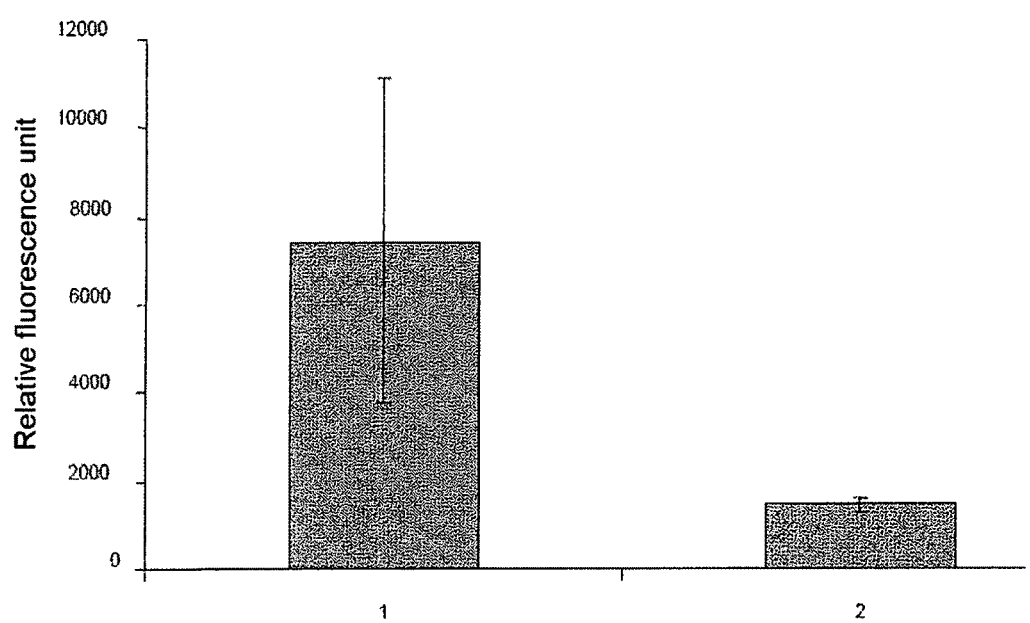
FIG. 13 shows the result of an ELISA with which sRAGE was detected in mouse plasma. It is clearly evident that the sRAGE plasma concentration to be found in 12-month old animals (bar 1) is distinctly higher than in 10-week young animals (bar 2).

A recombinant soluble mouse RAGE (from R&D Systems, Wiesbaden; Custom03) was employed as control for the ELISA.

c) Result:

FIG. 13 shows the result of the measurement of sRAGE in the plasma of 12-month old (1) and 10-week old (2) transgenic Tg2576 mice. It is evident that sRAGE is elevated in the plasma of old mice. This can be explained by the fact that, as the age of the animals increases, the expression of RAGE switches from the membrane-bound (in young animals) to the soluble form (in old animals), in particular as a function of the amyloid production. This result supports the finding of the invention that NtermR31 antiserum recognizes an "active receptor status" which is not defined by commercial antisera (cf. Exemplary embodiment 7, FIG. 12). The plasma of the non-transgenic strain C57B16 showed comparable sRAGE plasma concentrations as the young transgenic animals (data not shown).

Exemplary Embodiment 9

Competition of the sRAGE/Aβ Oligomer Interaction by Anti-NtermR31 and Anti-sRAGE Antibodies a) Materials and Test Procedure The tests on the displacement of sRAGE-amyloid beta oligomer (globulomer) binding by antibodies were carried out with the homogeneous time-resolved fluorescence (HTRF) technique from CIS Bio International (Bagnols, France). The HTRF donor and acceptor components, anti6HIS-europium cryptate (CIS Bio catalog number: 61HISKLA: 500 wells/13 µg) and streptavidin XL-665 (CIS Bio catalog number: 6HISAXLA, 500 wells/250 µg) were each dissolved in 250 µl of dd $H_2O$, Starting from these stock solutions, 1:50 working dilutions were prepared with a final concentration of 7.4 nM anti6His-cryptate and 121.2 nM streptavidin XL-665 in PBS, pH 7.4.

Rabbit IgG (order No.: 15006; Sigma, Taufkirchen, Germany) served as negative control in this test. The polyclonal anti RAGE antibody AF1145 (R&D Systems; Wiesbaden, Germany) was employed as positive control. The anti NtermR31 immunglobulins used were obtained, as already described elsewhere, through Biotrend (Cologne, Germany).

To carry out the tests, initially 4 µl of the recombinant sRAGE protein (preparation and purification as described, concentration 1 µM) were incubated in separate mixtures with in each case 4 µl of the antibody solutions to be tested or the IgG control in the concentrations of 7.14 µM, 3.57 µM, 1.78 µM, 0.892 µM, 0.446 µM, 0.223 µM, 0.112 µM, 0.056 µM and 0 µM at room temperature for one hour.

Then, 4 µl of a 4 µM stock solution of the Aβ 1/5 biotin globulomers were added to the mixture (final concentration 800 nM) and incubated at room temperature for a further hour. The A beta 1/5 biotin globulomer concentration indicated here is based on the Aβ 1-42 monomers which were used to prepare the globulomers (in accordance with WO 2004 067561). 2 µl portions of the 7.4 nM anti6His-cryptate solution described above and of the 121.2 nM streptavidin were added, and then this mixture was incubated, now at 4° C., for a further two hours. After addition of 4 µl of a 2M KF stock solution, the complete mixture was measured in a BMG Pherastar fluorescence measuring instrument (BMG Labtech GmbH, Offenburg, Germany) in HTRF mode. The calculated % DeltaF values were transferred into GraphPad Prism 4 (GraphPad Software, San Diego, USA) and evaluated. The concentrations indicated in the graph are based on the final concentration of the complete 20 µl mixture.

b) Result

Figure 14:
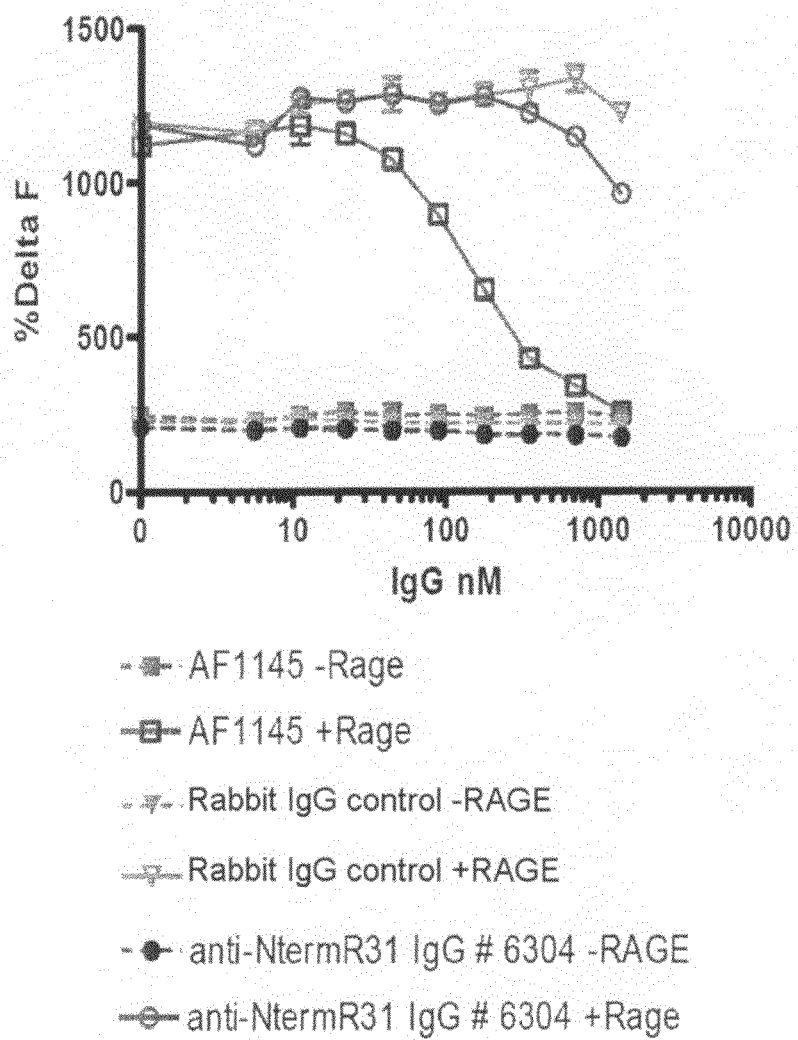
FIG. 14 shows the result of a competition experiment of the sRAGE/Aβ-oligomer interaction by anti-NtermR31 antibodies (circles) and anti-sRAGE antibodies (squares) (AF1145) as a function of the immunoglobulin concentration employed (nM) in an HTRF assay. A rabbit IgG non-immune serum (triangles) was additionally employed as control. The control mixtures without sRAGE (broken lines) show no change in the measured levels of fluorescence as the antibody concentration increases. In the presence of sRAGE, addition of rabbit control serum brings about no decrease in the fluorescence and thus no inhibition of the sRAGE-AF interaction. By contrast, a significant inhibition of the sRAGE-AB interaction is observed with increasing concentration of polyclonal anti-sRAGE antibodies and polyclonal anti-NtermR31 antibodies.

The result of the tests is shown in FIG. 14. As expected, no change in the measured fluorescence levels with increasing antibody concentration is observed in the control mixtures without sRAGE. In the presence of sRAGE, addition of rabbit control serum brings about no decline in the fluorescence and thus no inhibition of the sRAGE-AR interaction. By contrast, a significant inhibition of sRAGE-AR interaction is observed with increasing concentration of polyclonal anti-sRAGE antibodies (from about 50 nM upwards) and polyclonal anti-NtermR31 antibodies (from about 800 nM upwards).

Exemplary Embodiment 10

Effect of NtermR31 on Excitatory Synaptic Transmission and Long-term Potentiation a) Preliminary Remarks Long-term potentiation (LTP) is a cellular model of learning and memory. The induction method used herein (theta burst stimulation) induces a so-called "weak" LTP which returns to the initial levels after some hours. The LTP is attributable to a strengthening of the synapse which—in contrast to short-term potentiation—also comprises longer-lasting post-synaptic alterations (e.g. modification of the receptor composition of the post-synaptic membrane). LTP-like states have been measured during memory formation in animals and, conversely, LTP induction influences memory performance in animals. Owing to the better accessibility for substances, synaptic transmission and LTP were measured in brain sections. Recordings were made in the CA1 region of the hippocampus.

b) Material and Methods

400 µm-thick transverse hippocampal sections from 7-8-week-old male Wistar rats (Harlan Winkelmann, Bochum, Germany) were prepared using a tissue chopper and equilibrated for at least 1 hour at 33° C. in Carbogen-gassed artificial cerebrospinal fluid (aCSF) of the following composition: NaCl 124 mM; KCl 4.9 mM; $MgSO_4$ 1.3 mM; $CaCl_2$ 2.5 mM; $KH_2PO_4$ 1.2 mM; $NaHCO_3$ 25.6 mM; glucose 10 mM; pH 7.4. Recordings were made from the section immersed in Carbogen-gassed artificial cerebrospinal fluid (aCSF) of the same composition.

Stimulation of the Schaffer collaterals took place in the stratum radiatum using a monopolar stimulating electrode with biphasic pulse (voltage range 1-5 V). Excitatory post-synaptic potentials (EPSPs) were recorded in the stratum radiatum using aCSF-filled glass electrodes against a chlorinated silver reference electrode (bath). These reflect in particular the strength of the glutamatergic synaptic transmission.

The values were determined from the gradient of the field EPSPs recorded every 5 min for a period of 120 minutes before and 120 minutes after LTP induction. LTP was induced by so-called theta burst stimulation (4×2 pulses at an interval of 200 ms with a double-pulse interval of 10 ms). The substance was washed in 100 minutes before tetanization.

c) Results

Figure 15:
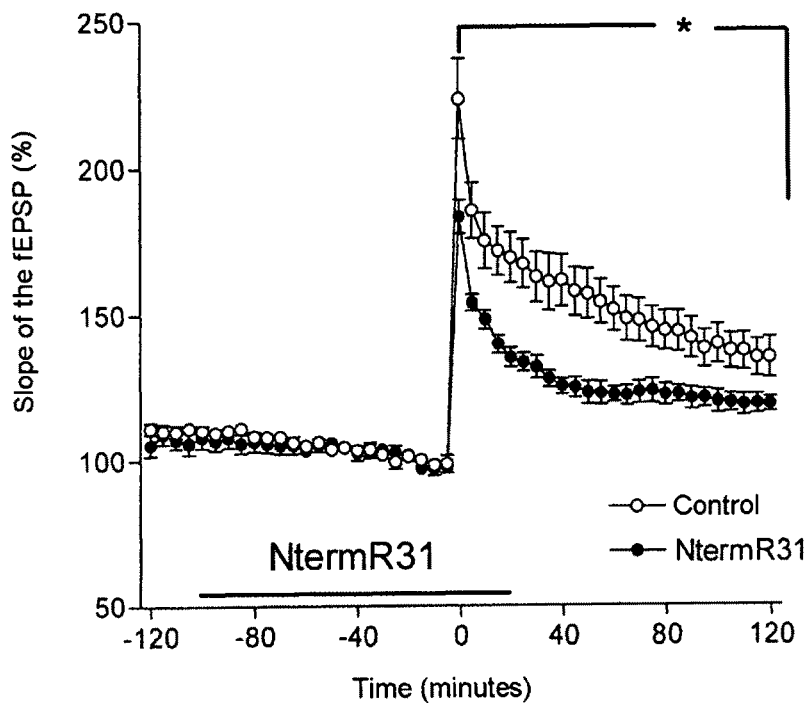
FIG. 15 shows the effect of 500 nM NtermR31 on the long-term potentiation (LTP) in hippocampal sections of male Wistar rats. Control sections n=11, 6 animals; Nterm-treated sections n=7, 4 animals. p=0.016, repeated measures ANOVA.
Figure 16:
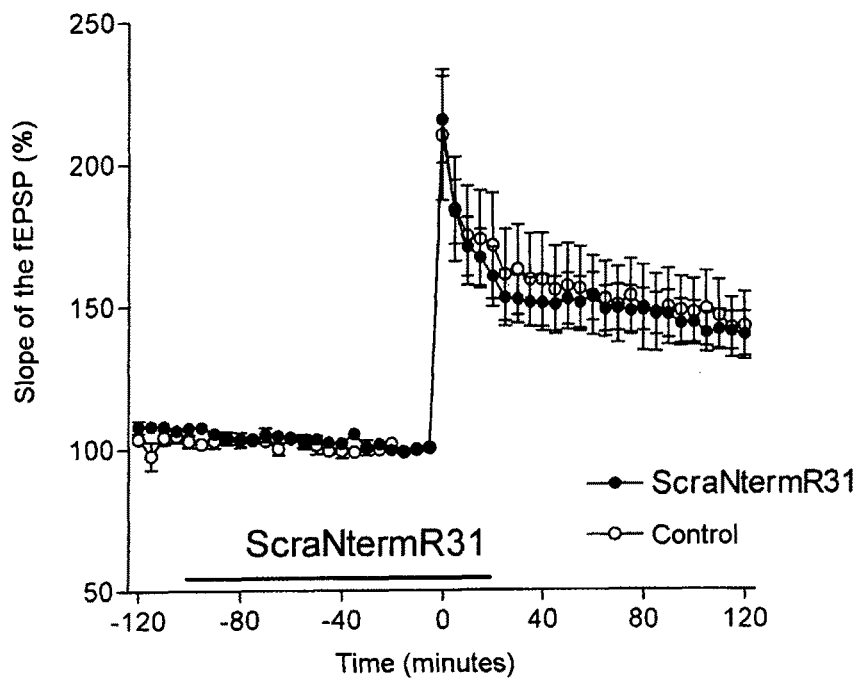
FIG. 16 shows the effect of 500 nM ScraNterm31 on LTP in hippocampal sections of male Wistar rats. Control sections n=7, 4 animals; ScraNterm-treated sections n=10, 5 animals. p=0.794, repeated measures ANOVA.

The effect of NtermR31 on synaptic the transmission and the LTP was investigated. Application of 500 nM NtermR31 distinctly suppresses both short-term and long-term potentiation. The reduction in the potentiated signal is significant (p=0.016; repeated measures ANOVA) over the entire post-tetanic measurement period (cf. FIG. 15). Washing in the control peptide (scraNtermR31, same amino acid composition but different sequence) has no effect on short-term and long-term potentiation (p=0.794; repeated measures ANOVA) (cf. FIG. 16). Accordingly, the effect of the NtermR31 peptide is specific for the amino acid sequence. The short-term potentiation can be derived from the LTP curve and corresponds to the first minutes of potentiation.

Figure 17:
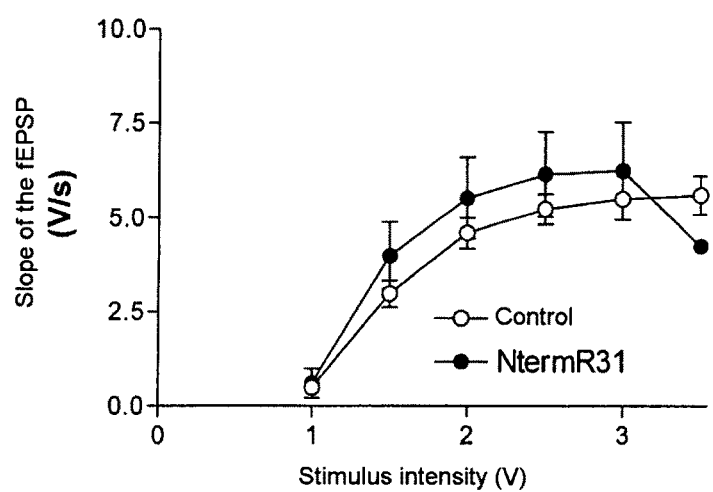
FIG. 17 shows the effect of 500 nM Nterm31 on the I/O ratio in LTP investigations on male Wistar rats.

NtermR31 administration has no effect on basal synaptic transmission. Application of NtermR31 for a period of 90 minutes does not change the size of the EPSPs, and thus leaves normal glutamatergic neurotransmission unaffected (cf. FIG. 15). The input/output ratio is also unaffected by NtermR31 (cf. FIG. 17), likewise indicating normal synaptic transmission on exposure to this peptide. There was no evidence of multiple population events in the traces, and thus no impairment of regular GABAergic transmission is assumed. Overall, therefore, it can be assumed that NtermR31 acts specifically on LTP. The consequence of this is that NtermR31 intervenes specifically in plastic synaptic processes thought possibly to be associated with learning and memory.

Exemplary Embodiment 11

Competition of the sRAGE/Aβ Globulomer Interaction by AGER-CDP a) Material and Methods:

Aβ 1-42 globulomer, prepared as disclosed in WO 2004 067561, biotinylated

The following synthetic AGER-CDPs were used:

```
                                              (SEQ ID NO: 32)
      TLQSELMVTPARGGDPRPTFSCSFSPGLPR  (peptide 6)

(SEQ ID NO: 33)
      LPRHRALRTAPIQPRVWEPVPLEEVQLVVE  (peptide 7)
```

The experiments on the displacement of sRAGE-Aβ globulomer binding by RAGE peptides were carried out by homogeneous time-resolved fluorescence (HTRF) technology from CIS Bio International (Bagnols, France). The HTRF donor and acceptor components, Anti6HIS europium cryptate (CIS Bio catalogue number: 61HISKLA; 500 wells/13 µg) and streptavidin XL-665 (CIS Bio catalogue number: 61HISAXLA, 500 wells/250 µg) were each dissolved in 250 µl of dd H₂O, Starting from these stock solutions, 1:50 working dilutions were prepared with a final concentration of 7.4 nM Anti6His cryptates and 121.2 nM streptavidin XL-665 in PBS, 0.1% BSA, pH 7.4.

Working solutions of peptides 6 and 7 were prepared with concentrations of 200 µM, 100 µM, 50 µM, 25 µM, 12.5 µM, 6.25 µM, 3.125 µM, 1.56 µM and 0.78 µM.

To carry out the tests, initially 4 µl of the working solutions of each of peptides 6 and 7, and of a buffer control, were mixed with 4 µl of a 4 µM stock solution of the Aβ 1/5 biotin globulomer (final assay concentration 800 nM) and incubated at room temperature for one hour. The A beta 1/5 biotin globulomer concentration indicated here is based on the Aβ 1-42 monomers which were used to prepare the globulomers. 4 µl of the recombinant sRAGE protein (prepared and purified as in preparation example 3a; concentration 1 µM) were then added to the assay, and the mixture was again incubated at RT for 1 h.

Figure 18:
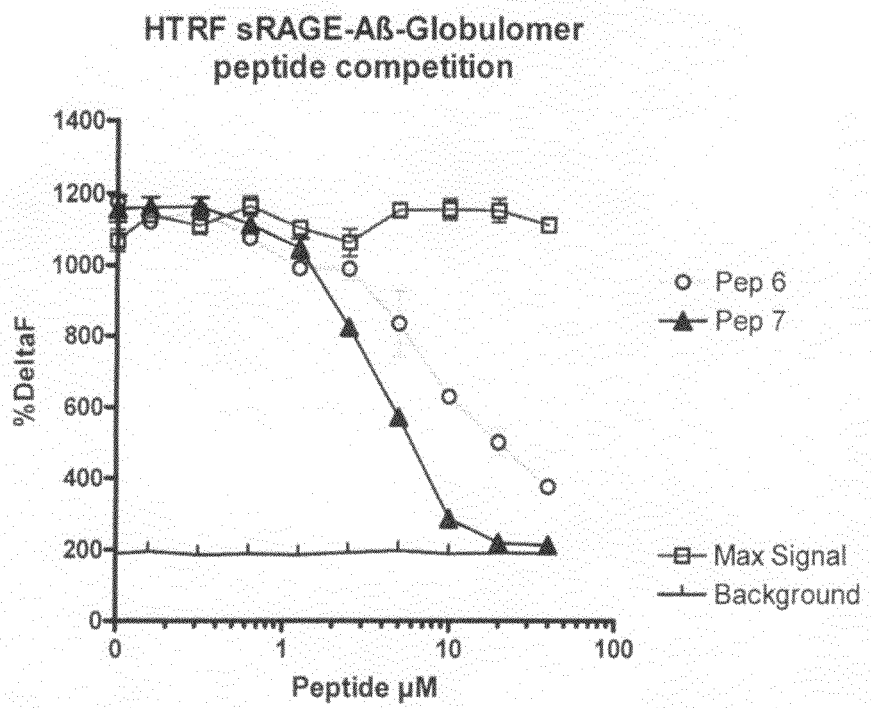
FIG. 18 shows the competitive inhibition of the sRAGE-Aβ oligomer interaction by the AGER-CDP peptides 6 and 7 of the invention.

2 µl portions of the 7.4 nM Anti6His cryptates and of the 121.2 nM streptavidin solution described above were added in order then to incubate this mixture, now at 4° C., for a further two hours. After addition of 4 µl of a 2M KF stock solution, the complete mixture was measured in a BMG Pherastar fluorescence measuring instrument (BMG Labtech GmbH, Offenburg, Germany) in HTRF mode. Separate measurements without peptide were carried out for the max-signal curve. For the background curve, measurements were used with in each case only the AntiGHIS cryptates and strepavidin XL solutions. The calculated % DeltaF values were transferred into GraphPad Prism 4 (GraphPad Software, San Diego, USA) and evaluated. The concentrations indicated in the graphs are based on the final concentration of the complete 20 µl mixture.

b) Test Results:

The results are depicted in FIG. 18 which is appended. Inhibition of Aβ oligomer binding to sRAGE is observed with increasing concentrations of peptides 6 and 7 which are derived from the Ig-like C2 domain of human sRAGE. The inhibitory activity is more pronounced for peptide 7.

Exemplary Embodiment 12

Binding of N-terminally Truncated sRAGE Fragments to Aβ Oligomer a) Material and Methods:

The following sRAGE peptides were employed:
sRAGE 1-331 (comprising the complete RAGE ectodomain) (cf. preparation example 3a)
sRAGE 102-331 (comprising the N-terminally truncated RAGE ectodomain) (cf. preparation example 3b)

The direct binding of sRAGE 1-331 and sRAGE 102-331 to Aβ globulomer was carried out with the homogeneous time-resolved fluorescence (HTRF) technique from CIS Bio International (Bagnols, France). The HTRF donor and acceptor components, Anti6HIS europium cryptate (CIS Bio catalogue number: 61HISKLA; 500 wells/13 µg) and streptavidin XL-665 (CIS Bio catalogue number: 611SAXLA, 500 wells/250 µg) were each dissolved in 250 µl of dd H₂O, Starting from these stock solutions, 1:100 working dilutions were prepared with a final concentration of 3.7 nM Anti6H is cryptates and 60.6 nM streptavidin XL-665 in PBS, 0.1% BSA, pH 7.4.

Working solutions of the A beta 1/5 biotin globulomers were prepared with concentrations of 10 µM, 5 µM, 2.5 µM, 1.25 µM, 0.625 µM, 312.5 nM, 156.25 nM.

4 µl of each of these working solutions and 4 µl of a buffer control were in each case mixed with 4 µl of a 1 µM RAGE 1-331 or 102-331 RAGE stock solution and incubated at room temperature for one hour. The A beta 1/5 biotin globulomer concentration indicated here is based on the Aβ 1-42 monomers which were used to prepare the globulomers.

Figure 19:
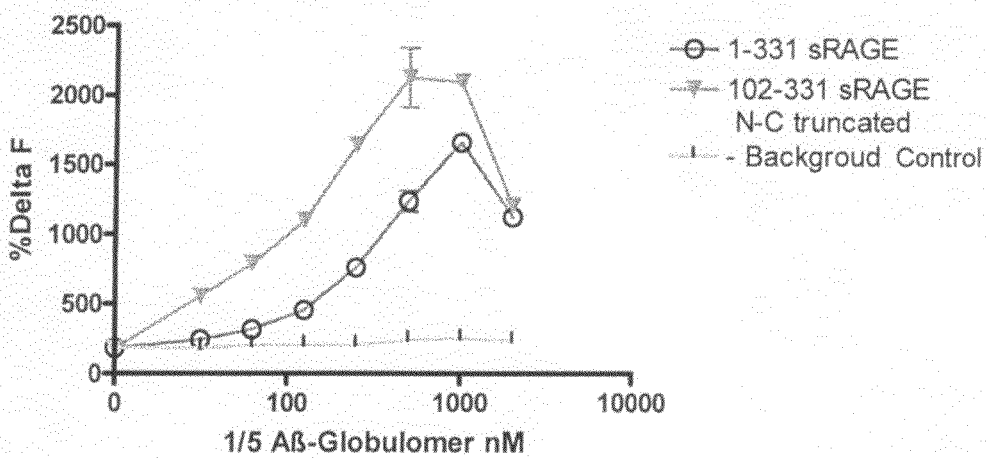
FIG. 19 shows the Aβ oligomer binding by sRAGE (1-331) and the N-terminally truncated sRAGE (102-331), which no longer has a functional V domain.

4 µl of each of the 3.7 nM Anti6H is cryptates described above and of the 60.6 nM streptavidin solutions were added in order then to incubate this mixture, now at 4° C., for a further two hours. After addition of 4 µl of a 2M KF stock solution, the complete mixture was measured in the BMG Pherastar fluorescence measuring instrument (BMG Labtech GmbH, Offenburg, Germany) in HTRF mode. For the background curve, measurements were used with in each case only the Anti6HIS cryptates and streptavidin XL solutions. The calculated % DeltaF values were transferred into GraphPad Prism 4 (GraphPad Software, San Diego, USA) and evaluated. The concentrations indicated in the graph are based on the final concentration of the complete 20 µl mixture.

b) Test Results:

The results are depicted in FIG. 19 which is appended. It is observed in this case that not only is the Ig-like, N-terminal V domain of sRAGE involved in the binding of Aβ oligomers, but the Ig-like C2 domain of sRAGE also has binding affinity for the Aβ oligomer. The two binding affinities are of comparable strength.

Exemplary Embodiment 13

Preparation and Characterization of Monoclonal anti-RAGE Antibodies a) Antibody Preparation
1. Immunization of Mice:

Balb/c and NJ mice (6-8 weeks old) were immunized subcutaneously with 30 μg of sRAGE-HIS antigen in complete Freud's adjuvant. The animals were then injected again, three times at intervals of three weeks in each case, with 30 μg of sRAGE antigen which was present in Immuneasy™ (from: Qiagen) for these immunizations.

Four days before the fusion, the mice were finally inoculated intravenously once again with 10 μg of sRAGE.

2. Cell Fusion and Screening of Hybridomas:

Spleen cells from immunized animals were fused to SP2/0-Ag14 myeloma cells in a ratio of 5:1 by standard methods. PEG 3000 was used for the fusion, and the selection was carried out in a medium comprising azaserine and hypoxantine. Seven to ten days after the fusion, when macroscopically visible colonies appeared, the cell culture supernatants were tested both in an ELISA for antibodies against sRAGE-HIS and in an FACS using stably transfected sRAGE-expressing HEK-293 cells. Positive cells from the ELISA/FACS analysis were propagated further and cloned by serial dilutions.

3. ELISA Protocol:

ELISA plates were coated with sRAGE protein (1 μg/ml) in PBS overnight at 4° C. After the plates had been blocked with milk, the mouse sera and the hybridoma supernatants were diluted in 1×PBS, 0.1% BSA (Sigma). The dilutions were carried out serially starting with a ratio of 1:500. 1:5 dilutions were used for screening. 50 μl of serum or cell culture supernatant were pipetted into each well and incubated at room temperature for one hour. After three washing steps in 1×PBS, 0.1% BSA, in each case 50 μl of anti-mouse IgG Fc-HRP (Pierce) in a 1:5000 dilution in PBS were added and incubated at room temperature for a further hour. After three washing steps, 50 μl of ABTS substrate (Sigma) were added. After five minutes at room temperature, the reaction was stopped by adding 50 μl of $2NH_2SO_4$ solution, and the plates were read at 450 nm.

4. FACS Protocol:

RAGE-expressing 293 HEK cells or untransfected control cells were harvested from cell culture plates and washed once in 1×PBS, 0.1% BSA solution. The cells were incubated with the hybridoma supernatants on ice for one hour. Renewed washing of the cells twice was followed by incubation with goat anti-mouse Ig-PG on ice for one hour. The cells were washed again, resuspended and the binding was detected in a Becton Dickenson FACScan apparatus.

5. Production and Purification of Monoclonal Antibodies:

The hybridoma cell lines were expanded in medium with 5% fetal bovine serum (low IgG content, Invitrogen). The supernatants were harvested and concentrated. The monoclonal anti-RAGE antibodies were purified by protein A chromatography and subsequent dialysis in PBS.

In this way for example antibodies designated ML37-11H8 and ML37-6A6 were obtained and characterized further.

b) Characterization in dot-blot Method

For characterization of the monoclonal anti-RAGE antibodies generated in this way, dot-blots were prepared with the complete sRAGE protein (1-131 sRAGE HIS) and with an N-terminally truncated version (102-331-sRAGE-HIS). The following amounts of protein were loaded onto Hybond ECL nitrocellulose membranes (Amersham, RPN68D), in each case in a volume of 1 μl of 1×PBS in duplicate: 30 ng, 10 ng, 3 ng, 1 ng, 0.3 ng, 0.1 ng, 0.03 ng and 0.01 ng. The dried membranes were then shaken in Western blocking reagent (Roche, No. 1921673) at a constant speed for 1 hour in order then to be incubated for a further hour under the same conditions with the monoclonal antibodies ML37-6A6 and ML37-11H8 in a concentration of 7.14 nM. After four washing steps for five minutes each in 1×PBS, the filters were shaken in Western blotting reagent (Roche, No. 192173) which comprised the secondary goat anti-mouse IgG AP antibody (Sigma No. A-7434) in a 1:2000-fold dilution for one hour. After a further four washing steps for five minutes each in 1×PBS, the filters were incubated in an NBT/BCIP substrate solution (Roche, No. 1697471) made up as stated by the manufacturer. The color reaction was stopped with distilled water after 10 minutes.

Figure 20:
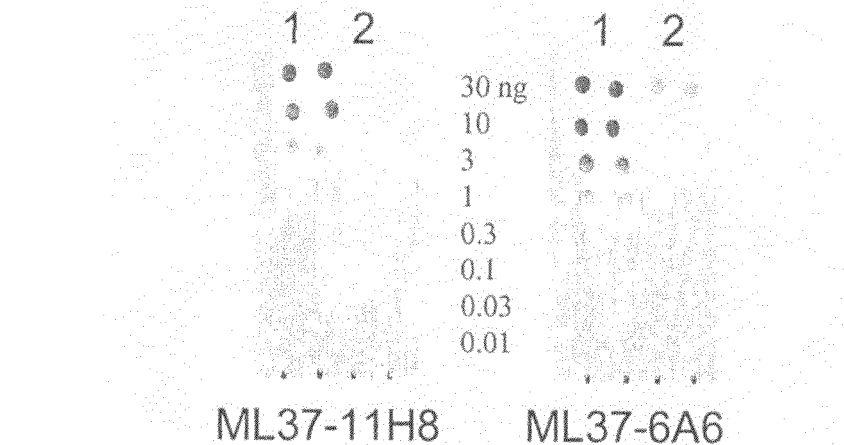
FIG. 20 shows the result of characterization of two monoclonal anti-RAGE antibodies of the invention (ML37-11H8 and ML37-6A6) in dot blots with the complete sRAGE protein (1-331 sRAGE-HIS) (vertical row 1 in each case) and of an N-terminally truncated version (102-331-sRAGE-HIS) (vertical row 2 in each case).

The results show (cf. FIG. 20) that both antibodies recognize the complete 1-331 sRAGE-HIS protein (row (1)). Differences in the antibodies are evident in relation to the detection of the N-terminally truncated 102-221 sRAGE-HIS protein (row (2)). The ML37-6A6 antibody also binds the N-terminally truncated version, which is not the case for the ML37-11H8 antibody.

c) Characterization by sRAGE-Aβ Globulomer Binding Competition

Experiments on displacement of the sRAGE-Aβ globulomer binding by monoclonal anti-RAGE antibodies were carried out using the homogeneous time-resolved fluorescence (HTRF) technology of CIS Bio International (Bagnols, France). The HTRF donor and acceptor components, anti6HIS-europium cryptate (CIS Bio catalogue number: 61HISKLA; 500 wells/13 μg) and streptavidin XL-665 (CIS Bio catalogue number: 61HISAXLA, 500 wells/250 μg), were each dissolved in 250 μl of double-distilled water. Starting from these stock solutions, 1:40 working dilutions were prepared with a final concentration of 10.25 nM anti6His-cryptate and 151.5 nM streptavidin XL-665 in PBS, pH 7.4. The negative controls in this test were mouse IgG1 and mouse IgG2a (order no.: M-5284 and M-5409 respectively; Sigma, Taufkirchen, Germany).

To carry out the test, firstly 4 μl of the recombinant sRAGE protein (preparation and purification as described, concentration 1 μM) were incubated in separate mixtures with in each case 4 μl of the antibody solutions to be tested or of the IgG controls in the concentrations 2 μM, 1 μM, 0.5 μM, 0.25 μM, 0.125 μM, 62.5 nM, 31.25 nM, 15.62 nM, 7.81 nM, 3.9 nM at room temperature for one hour. The background control contains no sRAGE protein and no antibodies, and the max signal control contains sRAGE and no antibodies. Volume losses were compensated by appropriate amounts of binding buffer (1×PBS pH 7.4; 0.1% BSA).

Thereafter, 4 μl of a 4 μM stock solution of the Aβ 1/5 biotin globulomer were added to the mixture (final concentration 800 nM) and incubated at room temperature for a further hour. The A beta 1/5 biotin globulomer concentration indicated here relates to the Aβ 1-42 monomers which were used to prepare the globulomers. In each case 2 μl of the 10.25 nM Anti6His-cryptate solution and of the 151.5 nM streptavidin-XL described above were added in order then to incubate this mixture for a further hour. After addition of 4 μl of a 2M KF stock solution, the complete mixture was measured in a BMG Pherastar fluorimeter (BMG Labtech GmbH, Offenburg, Germany) in the HTRF mode. The calculated % DeltaF values were plotted and analyzed in a GraphPad Prism 4 (GraphPad Software, San Diego, USA). The concentrations indicated in the graphs relate to the final concentration of the complete 20 μl mixture.

Figure 21:
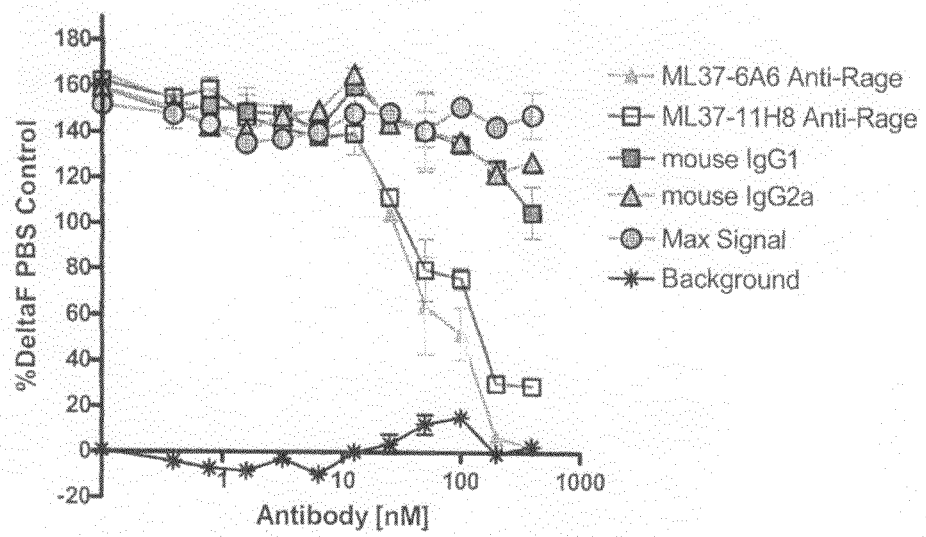

It is seen (cf. FIG. 21) that both the ML37-11H8 antibody and the ML37-6A6 antibody are able to compete efficiently with the Aβ globulomer-sRAGE binding. As shown in the dot-blot analysis, the antibodies recognize different parts of the sRAGE protein, unambiguously demonstrating that both C-terminal and N-terminal regions of sRAGE can serve as point of attach by antagonistic therapeutic reagents.

We claim:

1. A hybrid protein comprising a) a peptide fragment of the C domain of the receptor for advanced glycation endproducts (AGER-CDP), which is a length of about 30 to about 50 amino acid residues, wherein said AGER-CDP comprises a sequence selected from the group consisting of

| | |
|---|---|
| DGKPLVPNEKGVSVKEQTRRHPETGLFTLQ, | (SEQ ID NO: 31) |
| TLQSELMVTPARGGDPRPTFSCSFSPGLPR, and | (SEQ ID NO: 32) |
| LPRHRALRTAPIQPRVWEPVPLEEVQLVVE; | (SEQ ID NO: 33) | and b) a heterologous protein or protein fragment.

2. The hybrid protein according to claim 1, additionally comprising a functional part of a protein selected from immunglobulins and fragments thereof.

3. The hybrid protein according to claim 1, comprising an Ig Fc fragment functionally linked to the AGER-CDP.

4. An AGER-CDP derivative comprising the hybrid protein according to claim 1 in PEGylated form or coupled to a marker.

5. The hybrid protein according to claim 1, wherein the AGER-CDP is in the form of a cyclic peptide.

6. A pharmaceutical composition comprising in a pharmaceutically acceptable carrier at least one active ingredient selected from the hybrid protein according to claim 1 and a nucleic acid sequence coding for said hybrid protein.

7. The pharmaceutical composition according to claim 6, additionally comprising as active ingredient an active substance selected from:
   a) neurotrophic factors, inosine, neuroimmunophilins, chondroitin sulfate proteoglycan-degrading enzymes;
   b) antibodies against neurite growth inhibitors, Nogo-A, MAG, Omgp, and/or their receptors,
   c) soluble NgR fragment, Nogo-A peptide fragments,
   d) inhibitors of the p75-mediated signal cascade, and
   e) cAMP and functional analogs, protein kinase A, arginase I, polyamines, ciliary neurotrophis factor.

8. The pharmaceutical composition according to claim 6, for intrathecal, intravenous, subcutaneous, oral, parenteral, nasal or inhalational administration.

9. An immunogen comprising hybrid protein according to claim 1, in a pharmaceutically acceptable carrier and optionally with an adjuvant for active immunization.

* * * * *